US007481817B2

(12) United States Patent  (10) Patent No.: US 7,481,817 B2
Sauer  (45) Date of Patent: Jan. 27, 2009

(54) INSTRUMENT FOR SURGICALLY CUTTING TISSUE AND METHOD OF USE

(75) Inventor: Jude S. Sauer, Pittsford, NY (US)

(73) Assignee: LSI Soultions, Inc., Victor, NY (US)

( * ) Notice: Subject to any disclaimer, the term of this patent is extended or adjusted under 35 U.S.C. 154(b) by 0 days.

(21) Appl. No.: 10/365,809

(22) Filed: Feb. 13, 2003

(65) Prior Publication Data

US 2004/0162572 A1    Aug. 19, 2004

(51) Int. Cl.
*A61B 17/32* (2006.01)
(52) U.S. Cl. .................. 606/170; 600/564; 600/565
(58) Field of Classification Search ............. 606/170, 606/171, 180, 159, 83; 604/22; 600/564, 600/565
See application file for complete search history.

(56) References Cited

U.S. PATENT DOCUMENTS 4,631,052 A    12/1986   Kensey
4,867,157 A    9/1989    McGurk-Burleson et al.

(Continued)

FOREIGN PATENT DOCUMENTS

DE    G 89 00 059.5    1/1989

(Continued)

OTHER PUBLICATIONS

Brochure entitled "Sew-Right SR 5, The Single Squeeze Suturing Device", LSI Solutions, Copyright 2000.

(Continued)

*Primary Examiner*—Kevin T Truong
*Assistant Examiner*—Victor X Nguyen
(74) *Attorney, Agent, or Firm*—Kenneth J. Lukacher

(57) ABSTRACT

An instrument for precisely cutting tissue to controlled dimensions (length, width, depth, and shape) is provided for the removal of tissue specimens from remote sites in the body of a patient, such as from the gastrointestinal tract, urinary tract, or vascular structures, or any tissue surface or soft tissue of the body. The instrument has a housing and a substantially flexible shaft extending from the housing to a distal end. The distal end of the instrument has an open cavity into which tissue is receivable. Suction can be communicated along the shaft to the distal end for distribution across the cavity utilizing a manifold having a grated tissue engaging surface with opening(s) for applying the suction, thereby pulling tissue adjacent to the distal end into the cavity against the tissue engaging surface of the manifold. One or more hollow needles are extendable from the housing through the shaft into the cavity to enable infusion of fluid, such as saline or a hemostatic agent, into the tissue. A blade in the distal end is extendable through the cavity over the manifold and across the opening to cut the tissue held by suction and stabilized by the needles in the cavity. The shape and depth of the tissue removed by the cuts is in accordance with the contour of the tissue engaging surface and the size and shape of the cavity at the distal end. The tissue so removed by the instrument may be for therapeutic intervention and/or represent a tissue specimen for biopsy suitable of diagnostic evaluation. The tissue edges in the patient's body left after cutting with this instrument readily avail themselves to apposition for enhanced healing.

49 Claims, 44 Drawing Sheets

U.S. PATENT DOCUMENTS

| | | | |
|---|---|---|---|
| 4,936,313 A | | 6/1990 | Burkhardt et al. |
| 4,979,951 A | * | 12/1990 | Simpson .................... 606/159 |
| 5,074,841 A | * | 12/1991 | Ademovic et al. ............ 604/22 |
| 5,084,010 A | | 1/1992 | Plaia et al. |
| 5,403,334 A | * | 4/1995 | Evans et al. ................. 606/159 |
| 5,419,774 A | | 5/1995 | Willard et al. |
| 5,429,136 A | | 7/1995 | Milo et al. |
| 5,431,666 A | * | 7/1995 | Sauer et al. ................. 606/139 |
| 5,496,341 A | | 3/1996 | Sauer et al. |
| 5,520,702 A | | 5/1996 | Sauer et al. |
| 5,562,686 A | | 10/1996 | Sauer et al. |
| 5,562,694 A | | 10/1996 | Sauer et al. |
| 5,624,457 A | | 4/1997 | Farley et al. |
| 5,626,588 A | | 5/1997 | Sauer et al. |
| 5,632,754 A | | 5/1997 | Farley et al. |
| 5,643,289 A | | 7/1997 | Sauer et al. |
| 5,643,296 A | * | 7/1997 | Hundertmark et al. ...... 606/159 |
| 5,665,100 A | * | 9/1997 | Yoon .......................... 606/170 |
| 5,690,664 A | | 11/1997 | Sauer et al. |
| 5,766,183 A | | 6/1998 | Sauer |
| 5,839,639 A | | 11/1998 | Sauer et al. |
| 5,908,429 A | | 6/1999 | Yoon |
| 5,910,105 A | | 6/1999 | Swain et al. |
| 5,954,731 A | | 9/1999 | Yoon |
| 6,004,269 A | * | 12/1999 | Crowley et al. ............. 600/439 |
| 6,010,476 A | * | 1/2000 | Saadat ......................... 604/22 |
| 6,071,233 A | | 6/2000 | Ishikawa et al. |
| 6,641,592 B1 | | 11/2003 | Sauer et al. |
| 6,669,643 B1 | * | 12/2003 | Dubinsky ................... 600/459 |
| 2001/0049509 A1 | | 12/2001 | Sekine et al. |
| 2002/0016624 A1 | | 2/2002 | Patterson et al. |
| 2003/0176874 A1 | | 9/2003 | Sauer |
| 2003/0176883 A1 | | 9/2003 | Sauer et al. |

FOREIGN PATENT DOCUMENTS

| | | |
|---|---|---|
| EP | 0 147 192 A2 | 7/1985 |
| WO | WO 02/062200 A2 | 8/2002 |

OTHER PUBLICATIONS

Brochure entitled "Ti-Knot TK 5, The Device to Instantly Secure and Trim Suture", LSI Solutions, Copyright 2000.

Hunter, John G. et al., Symposium, "Treatment and Follow-Up of Barrett's Esophagus", Contemporary Surgery, vol. 58, No. 10, pp. 495-502 (2002).

* cited by examiner

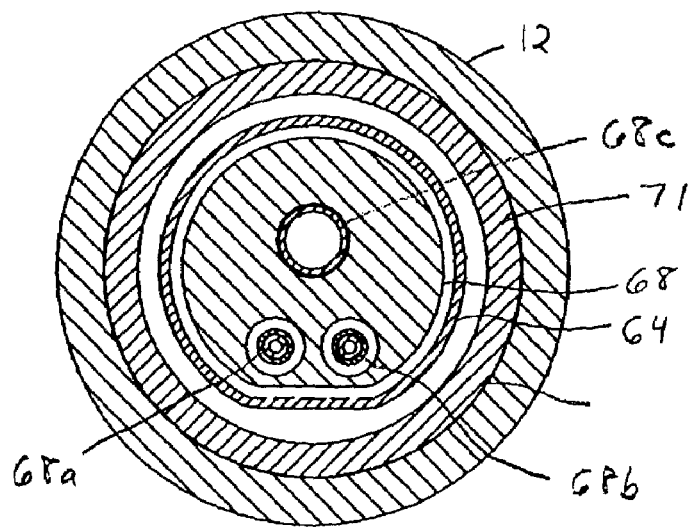
FIG. 6
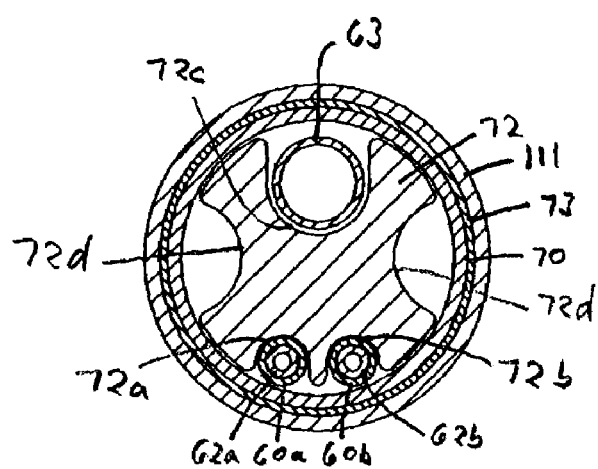 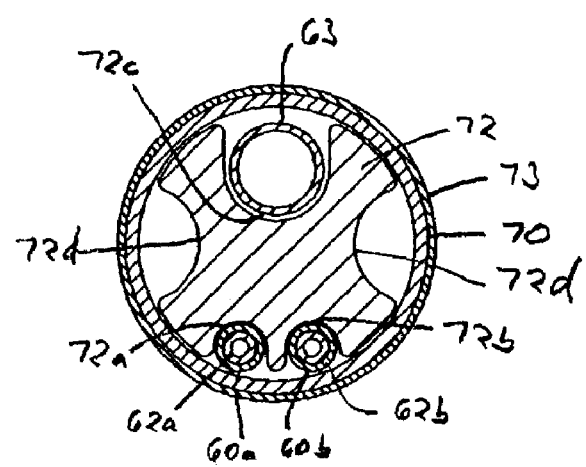
FIG. 7    FIG. 8

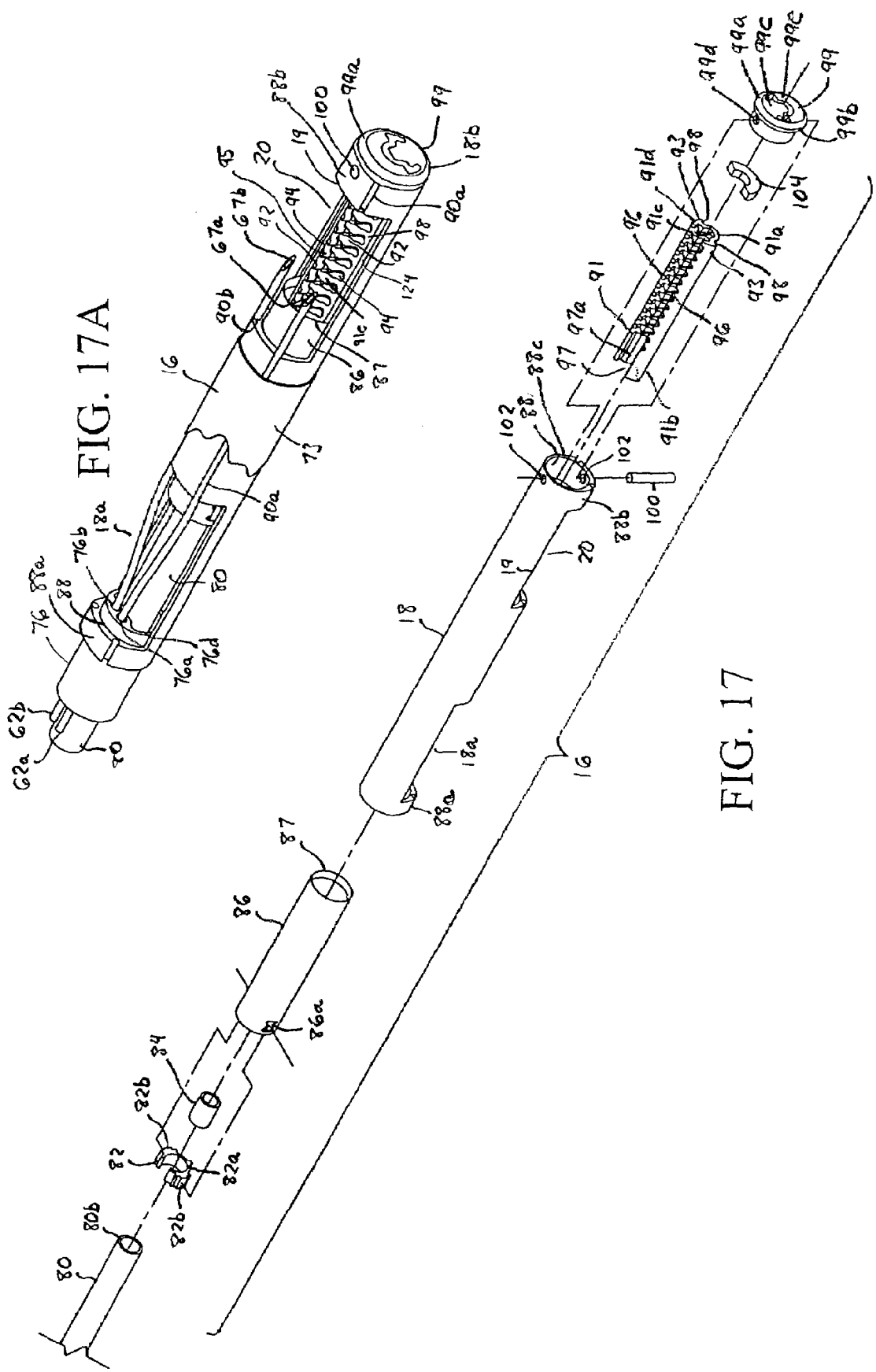

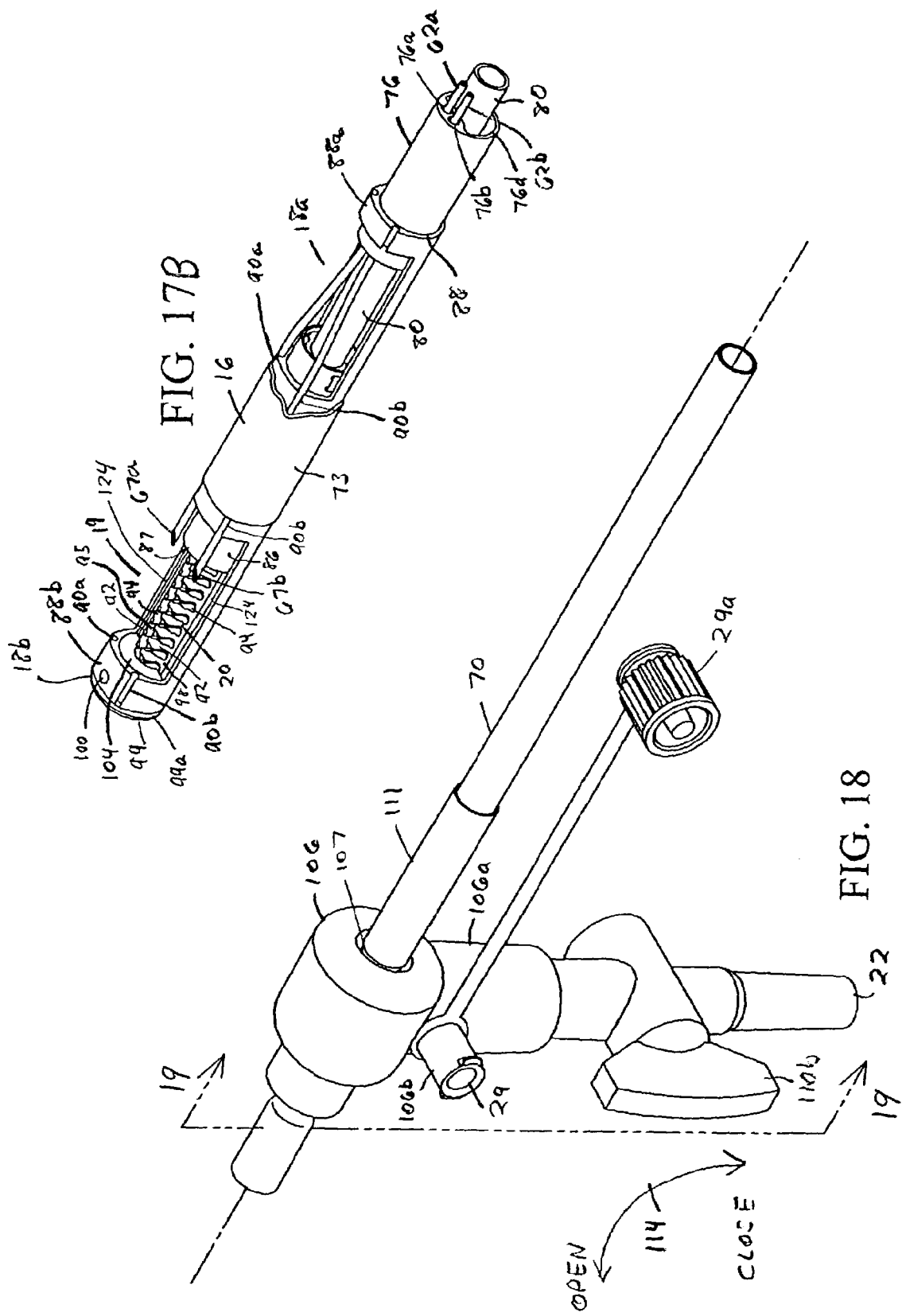

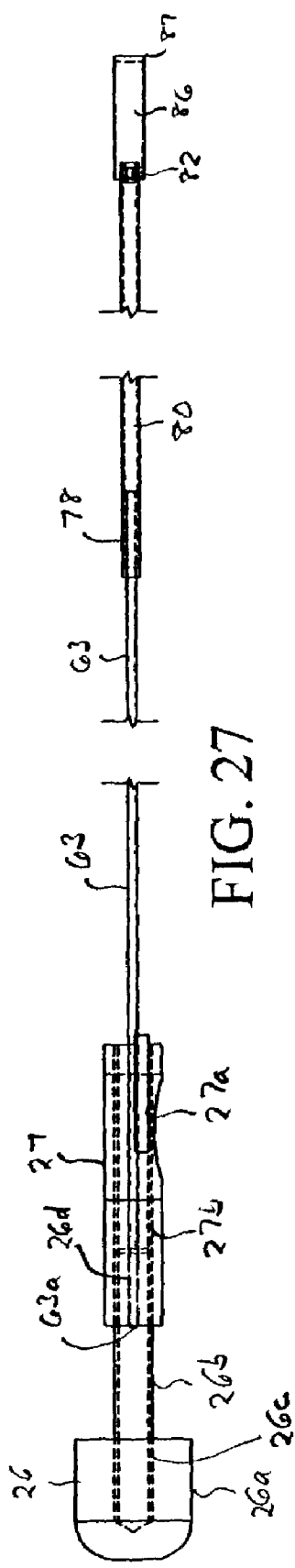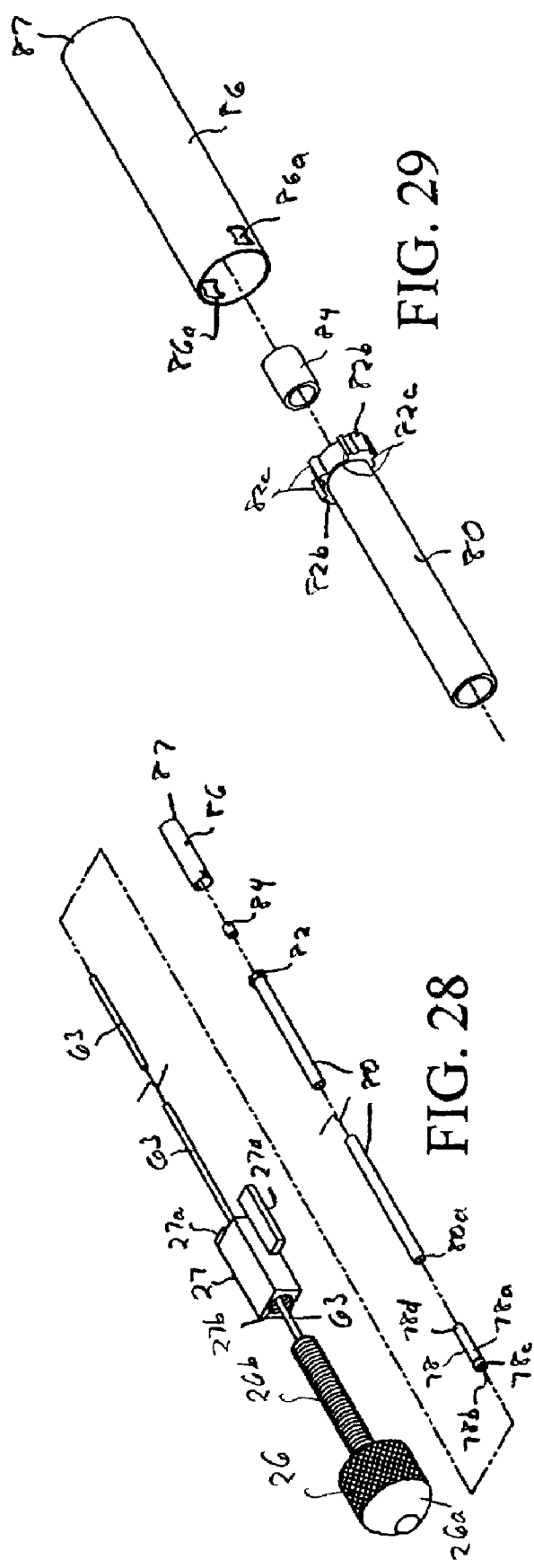

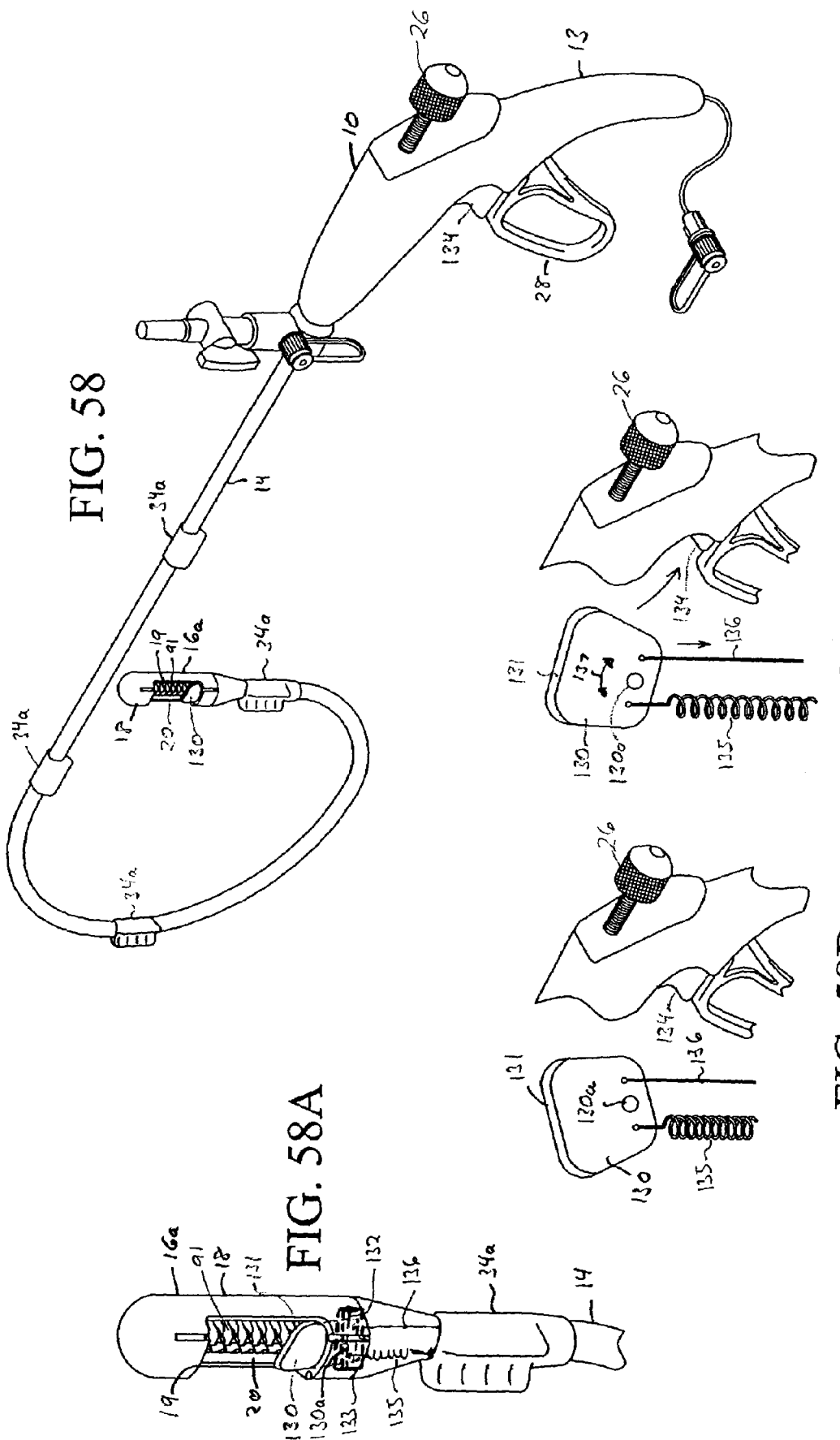

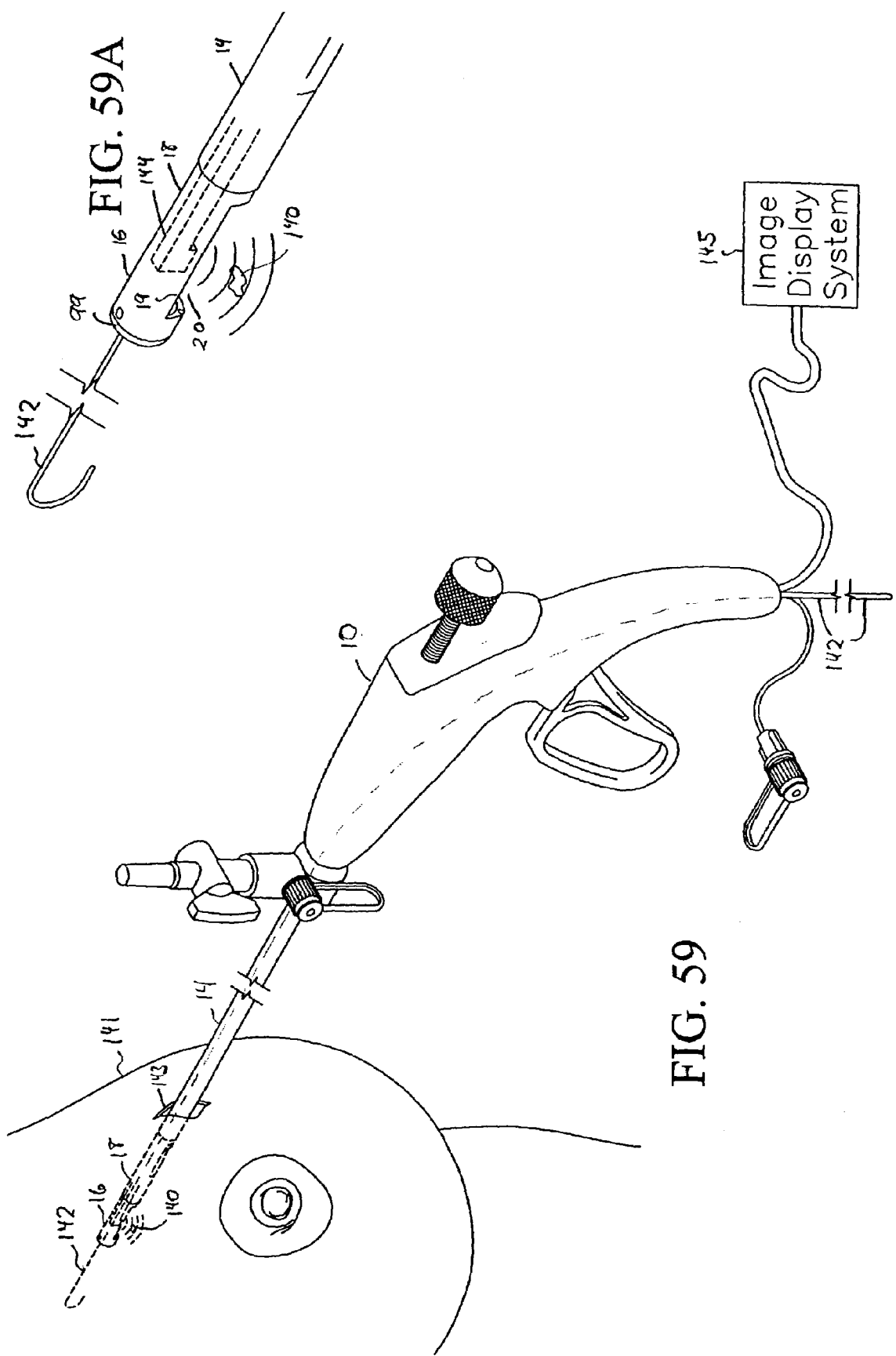

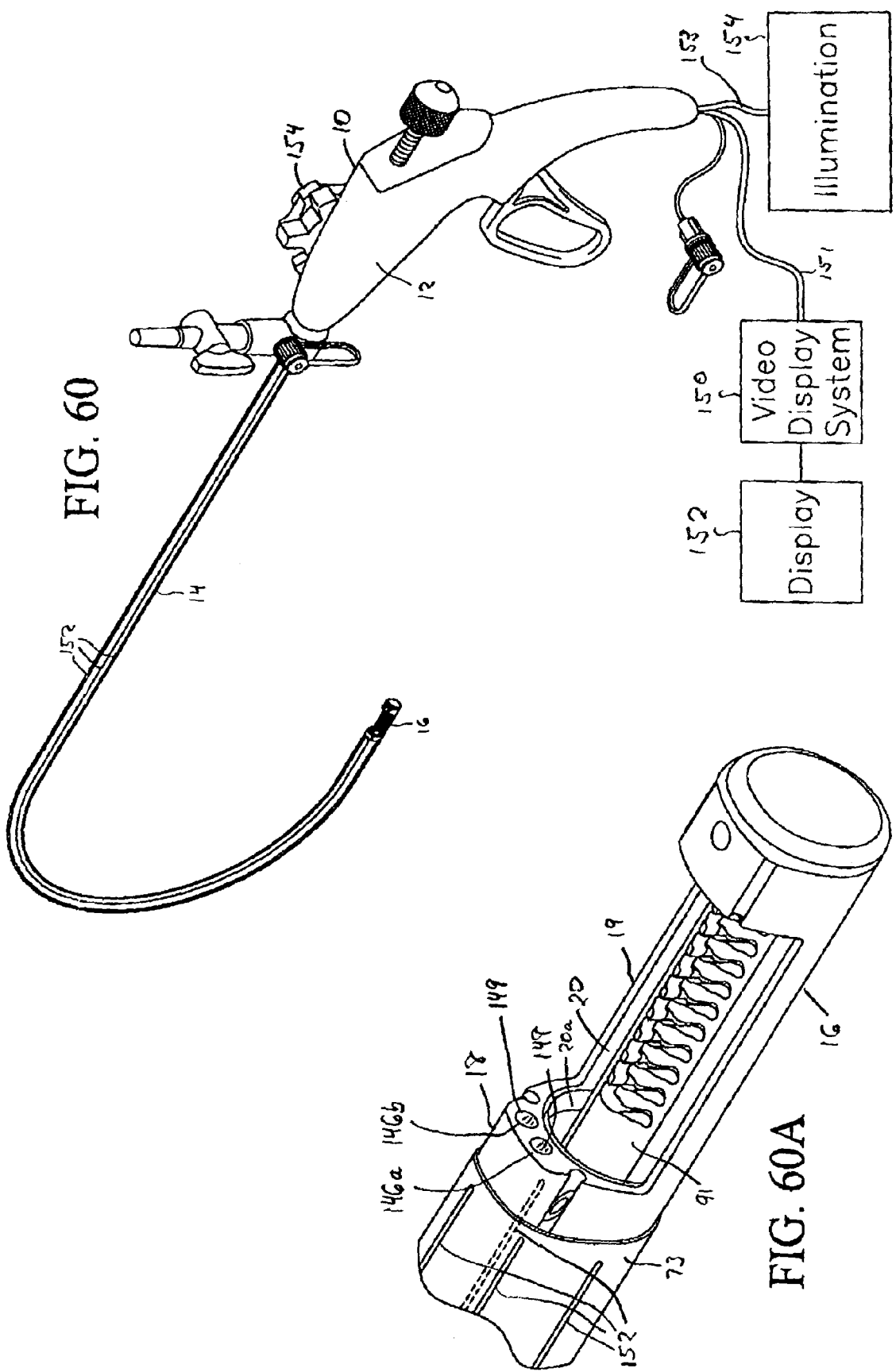

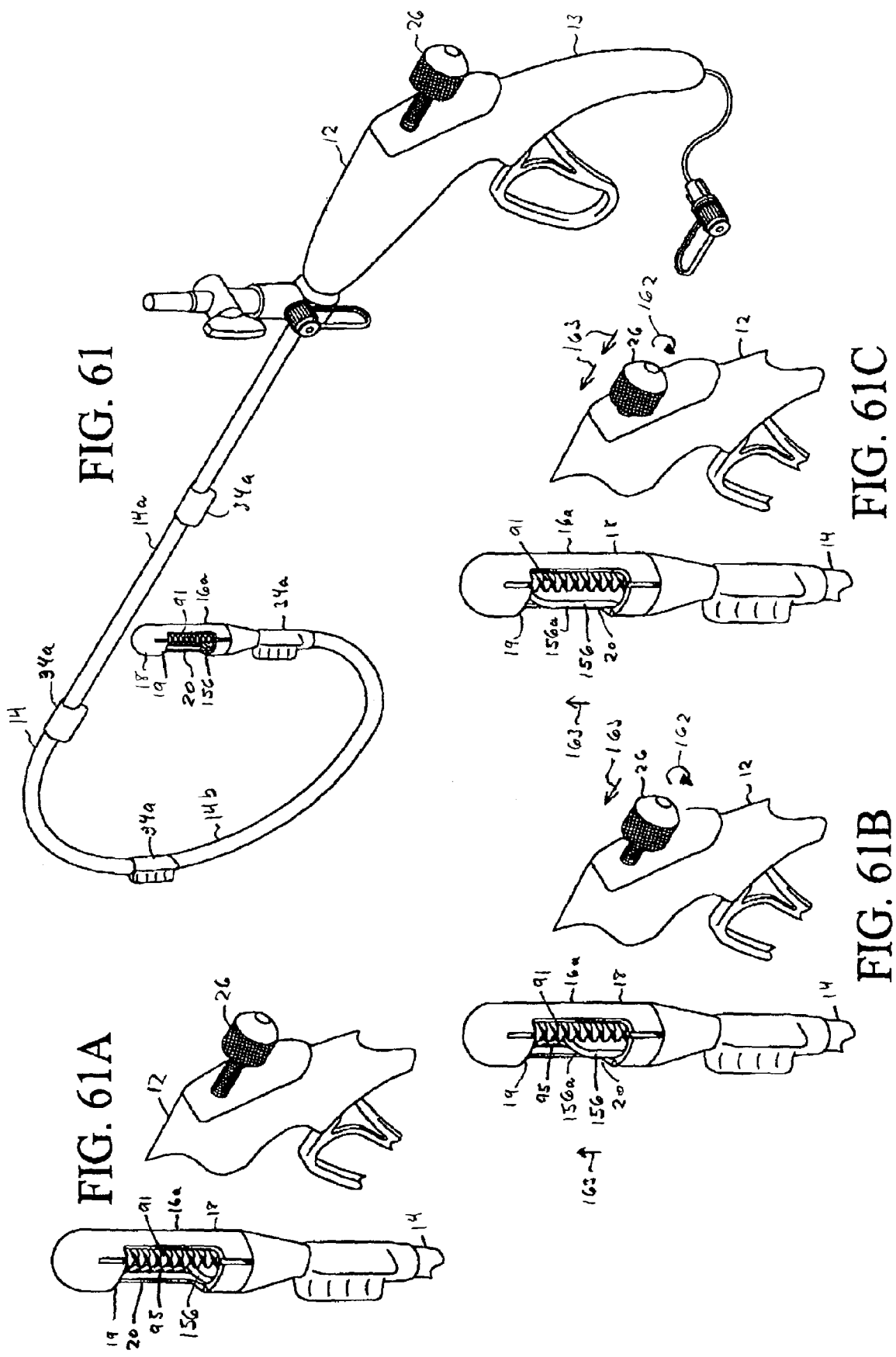

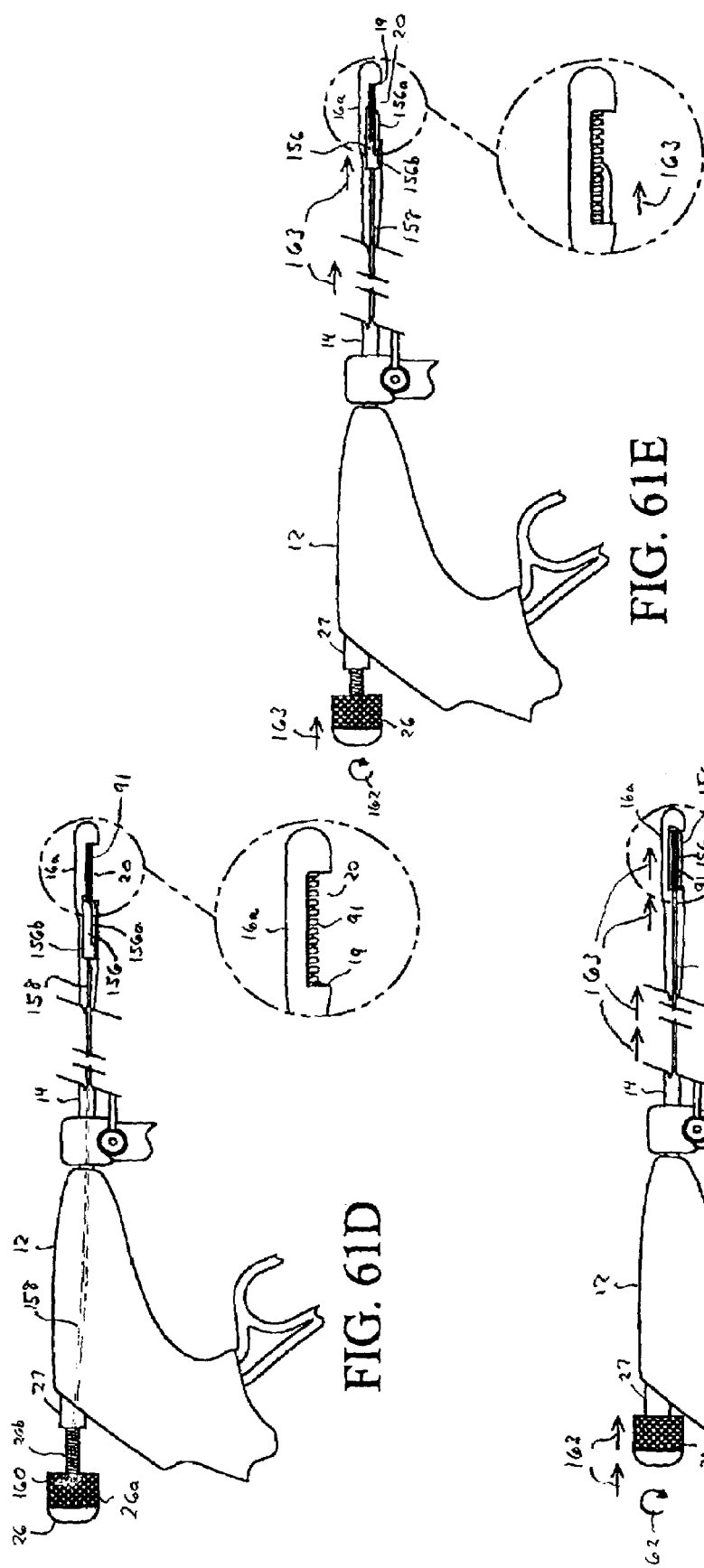

INSTRUMENT FOR SURGICALLY CUTTING TISSUE AND METHOD OF USE

FIELD OF THE INVENTION

The present invention relates to an instrument (and method) for surgical cutting of tissue in the body of a patient, and in particular, to remote surgical cutting of tissue in the body of a patient to a precise length, width, and depth, and overall shape. The invention is useful for surgical removal of tissue from a site in the body of a patient, including, the lining of tubular structures, such as the gastrointestinal tract (e.g., the esophagus or stomach), urinary tract, or vascular structures, but may also be used to remove tissue from any tissue surface (e.g., surface of the liver, lining of the peritoneal cavity), or within soft tissue structures (e.g., from within breast or brain tissue).

BACKGROUND OF THE INVENTION

A need exists for an improved surgical instrument to enable safe and efficacious removal of living tissue during diagnostic and therapeutic medical interventions. While instruments have been designed with simple blades and rotors for cutting or chopping tissue, they do not provide precision removal of a tissue specimen of a predetermined length, width and depth. It is also difficult for such instruments to harvest tissue from a patient under realistic clinical conditions and to safely access remote locations in the patient. Further, such instruments lack the capability to effect separation of tissue planes at a site prior to tissue removal, or to deliver therapeutic agents to tissue. For example, devices for removal of arterial blockage, often called artherectomy catheters, have distal ends with cutting blades of various types, such as longitudinal, helical, or circular cup-shaped blades. Often such blades are presented through opening(s) at the distal end of the devices. Examples of artherectomy catheters may be found in U.S. Pat. Nos. 4,979,951, 5,074,841, or 5,643,296. Other surgical cutting device, such as useful in endoscopic bone surgery, have helical shaped rotatory cutters extending in through a tube having multiple openings to receive tissue, such as described in U.S. Pat. No. 4,867,157. Although such devices may be useful for their particular limited applications, they do not generally control for precise tissue sample size or cutting depth, mechanical tissue engagement, preservation of biopsy specimen for subsequent examination, or injectable fluid delivery.

One application for removal of tissue relates to the esophagus, and in particular Barrett's esophagus, a disease associated with GERD or gastroesophageal reflux disease representing a precancerous condition of the mucosal lining the esophagus. It is important that in diagnosing Barrett's esophagus, cancer, or other abnormality in the esophageal lining, that a biopsy be taken for examination. Currently, a flexible endoscope or gastroscope is used to locate the suspected tissue in the esophagus. Through a narrow (1 to 3 mm) channel in the endoscope, long, thin biopsy forceps (typically two sharp edged hemispheres that close onto each other) are passed and used to engage and collect few small bites of the tissue at different esophageal locations. Accurate forceps placement remains problematic as does frequent bleeding at the biopsy site, further obscuring accurate tissue harvest. As such imprecise biopsy forceps sampling may miss diseased tissue, it would be desirable to obtain a larger, well controlled specimen of tissue from the esophagus, thereby reducing the risk of misdiagnosis.

The physical location of such tissue in the esophagus makes alternative non-invasive medical intervention along the gastrointestinal tract difficult. One approach is to inject saline submucosally using a flexible endoscope, and then a snare to capture an area of tissue. However, this approach may be limited to capturing nodular areas, rather than a long segment of the esophageal lining. A further approach described in U.S. Published Patent Application No. 2001/0049509, filed Dec. 6, 2001, provides an endoscopic treatment system for treating and removal of mucosal lining from the esophagus by tools extending through endoscopic channels, such as a syringe needle for localized injections of the mucous membrane, forceps for gripping mucous membrane, and knives(s) for peeling or cutting off the mucous membrane.

Like other surgical cutting instruments described earlier, it is difficult using these approaches to remove tissue to precisely control the cutting depth into the esophageal lining, which can result in inadequate removal of mucous membrane or inadvertent removal of sub-mucosal layers leading to possible esophageal wall perforation. Further in the case of U.S. Published Patent Application No. 2001/0049509, the use of forceps and knifes represents a manual time consuming process prone to human error. A further problem of these approaches is that if the wound in the esophageal lining is to be closed, such as by suturing (i.e., stitches) or other closure devices, there may not be proper tissue edges on either side of the wound to appose, resulting in failure of stitches or tearing of stitches through the tissue, and may lead to failure of primary healing. Thus, it would further be desirable to remove tissue from the lining of the esophagus with a single instrument enabling remote location in the esophagus with precise control of the cutting shape and depth, and moreover can provide tissue edges on either side of the resulting wound that can be well apposed for primary closure of the wound site. Such proper apposition of tissue edges is necessary when a wound is closed to induce primary healing, and thereby rapidly provide a strong more durable wound closure than where accurate wound edge apposition is not present. Such wound closure in tubular structures having mucosal lining is especially difficult due to the slippery nature of such tissue, thus, it would still further be desirable to stabilize the tissue prior to being cut.

SUMMARY OF THE INVENTION

Accordingly, it is a principal object of the present invention to provide an instrument for surgically cutting tissue enabling control removal of a specific dimensions and volume (i.e., length, width, depth, and shape) of tissue in the body of a patient.

It is another object of the present invention to provide an instrument for surgically cutting tissue at remote sites in tubular structures, such as the esophagus, stomach, urinary tract, or vascular structures, or from any tissue surface or soft tissue in a patient's body which is naturally or surgically accessible.

It is another object of the present invention to provide an instrument for surgically cutting tissue which enables large tissue biopsies to be taken at a certain depth to facilitate diagnosis of possible abnormal tissue.

A further object of the present invention is to provide an instrument for surgically cutting tissue in which the shape of the cut in the tissue facilitates accurate apposition of the edges of the tissue for wound closure which promotes primary healing.

It is another object of the present invention to provide an instrument for surgically cutting tissue which mechanically holds the tissue to be cut by suction and needles upon a tissue engaging surface at the instrument's distal end.

A yet further object of the present invention is to provide an instrument for surgically cutting tissue and enabling the infusion of a fluid which promotes separation of the tissue layers.

A still further object of the present invention is to provide an instrument for surgically cutting tissue and enabling the infusion of a fluid which provides therapeutic or pharmaceutical agents (e.g., epinephrine for hemostasis and/or lidocaine for local analgesic).

Another further object of the present invention is to provide an instrument for surgically cutting tissue of the body having a substantially flexible shaft with a distal end locatable at remote sites of the body (e.g., within the gastro-intestinal tract, peritoneal cavity, breast or brain) in which instrument is remotely controlled.

Briefly described, the present invention embodies an instrument for the precise surgical cutting of tissue to remove a predetermined length, width, depth, and shape of tissue at a site in a patient's body. The instrument has a housing at its proximal end and a substantially flexible shaft extending from the housing to a distal end. The distal end has an opening to a cavity into which tissue is receivable. Suction can be communicated from a port along the shaft to the distal end for distribution in the cavity utilizing a manifold member having a tissue engaging surface with sufficient openings distributing the suction across the cavity, thereby pulling tissue adjacent the distal end into the cavity against the tissue engaging surface of the manifold member. One or more hollow needles are extendable from the housing through the shaft into the cavity to assist in stabilization of tissue and the delivery or infusion of fluid, such as saline and/or therapeutic or pharmacological agents, to tissue located therein. A blade in the distal end is extendable over the manifold member, through the cavity, and across the opening thereto, to cut the tissue located in the cavity held by suction and stabilized by needles against the tissue engaging surface. The depth of the tissue cut is in accordance with the contour of the tissue engaging surface in the cavity and size of the cavity. Dimensions of length, width, and overall shape of the tissue cut are in accordance with the size and shape of the cavity at the distal end and contour of the tissue engaging surface.

The tissue so removed by the instrument may represent a tissue specimen for biopsy for subsequent diagnostic evaluation (e.g., histologic review). If the entire pathologic element of the tissue sample is completely removed by one or repeated use of the instrument, the process may be considered therapeutic and no further patient interaction may be required. When appropriate, resulting wound edges at the site of the removed tissue can be apposed to further augment healing of the wound closure.

The blade may represent a rotatable tubular blade or an oscillating blade member translatable in the distal end sufficient to cut the tissue extending therein across the opening to the cavity. The application (or removal) of suction, translation (forward or backward) of the blade, extension (or retraction) of needles, and delivery of fluid via such needles, are each independently and remotely controlled at the proximal end of the instrument.

The invention also provides a method for cutting for removal of tissue from a patient's body. The method includes: locating the distal end of the instrument in a patient's body adjacent the tissue to be cut (or removed); providing suction to pull tissue via the opening at the distal end into the cavity of the distal end against a tissue engaging surface having slots for distribution of the suction; partially extending one or more hollow needles through the cavity in the tissue therein; delivering pressurized fluid through the needles into such tissue sufficient for tissue plane separations; fully extending the needles through the cavity; and then cutting the tissue in the cavity adjacent the opening. The cut tissue represents a tissue specimen that may be removed from the distal end by retracting the blade and needles, and removal of suction, to release the tissue. Removal of tissue may occur while the distal end is in the patient body, or after removal of the instrument from the patient's body. The method may be repeated to remove multiple tissue samples with the same instrument.

The instrument may be located into the patient's body, such as in a tubular structure, via an accessory tube coupled to an endoscope, a channel of an endoscope, or may be coupled along its shaft by guide members to the shaft of an endoscope. The instrument may be used without an endoscope, and may optionally include a system for optical or ultrasonic imaging, or other imaging modalities, to obtain images at its distal end for use in locating tissue to be removed by the instrument and observing instrument operation. Further, an optional mechanism for steering the distal end from the housing of the instrument may be provided.

Thus, the instrument of the present invention provides precision removal of tissue of a predetermined depth and volume (length, width, and height). A mechanical means securely gain purchase on targeted tissue and appropriately hold it throughout the removal process, such as is provided herein with the vacuum (suction), needle and blade combination, enables effective tissue capture and retrieval at more remote locations within the body and without requiring direct manual manipulation by a health care provider, such as a surgeon. The use of needles for the remote injection of mixtures of sterile fluids, not only provides for a convenient and reliable way of delivering soluble pharmaceutical agents (such as epinephrine, a hemostatic agent, to control blood loss, and lidocaine, a local anesthetic, to minimize related discomfort), it also provides for accurate bulk fluid delivery (e.g., a normal saline carrier) to enable mechanical tissue plane separations using pressurized fluid volume injections. Further, the instrument is useful for removing tissue from specified locations in tubular structures, such as in the gastrointestinal or urinary tract, or vascular structures of a patient, or in any other tissue surface or soft tissue in a patient's body which is naturally or surgically accessible. Also, the instrument enables large specimen harvest and more complete removal of intact tissue specimens which can provide therapeutic relief. The instrument and method addresses a persistent problem by enabling precision tissue removal with minimizing patient morbidity while maximizing the health care provider's effectiveness.

The instrument may also be used for incising tissue to a controlled length and depth by replacing the tubular or oscillating blade with a linear blade translatable across cavity in the distal end of the instrument. The linear blade provides a longitudinal cut in tissue engaged against the manifold member.

BRIEF DESCRIPTION OF THE DRAWINGS

The foregoing objects, features and advantages of the invention will become more apparent from a reading of the following description in connection with the accompanying drawings, in which:

FIG. 6 is a cross-sectional view along lines 6-6 of the instrument of FIG. 3;

FIG. 7 is a cross-sectional view along lines 7-7 of the instrument of FIG. 3;

FIG. 8 is a cross-sectional view along lines 8-8 of the instrument of FIG. 3;

FIG. 17 is an exploded view of the distal end of the instrument of FIG. 1;

FIG. 17A is a broken view of the assembled distal end of the instrument of FIG. 1;

FIG. 17B is a broken view of the assembled distal end of the instrument of FIG. 1 from a different perspective than of FIG. 17A;

FIG. 18 is a partial detailed view of the vacuum assembly mounted on the shaft of the instrument of FIG. 1;

FIG. 27 is a side view of components of the instrument of FIG. 1 for driving and retracting a cutting blade at the distal end of the instrument;

FIG. 28 is an exploded view of components of the instrument of FIG. 1 for driving and retracting a cutting blade at the distal end of the instrument;

FIG. 29 is a more detailed exploded view of the tube blade coupling of FIG. 28;

FIG. 58 is a perspective view of the instrument of FIG. 1 with an optional larger distal end to cut a larger tissue sample, optional guide members along the shaft of the instrument for coupling the instrument to an endoscope, and another cutting mechanism having an oscillating blade;

FIG. 58A is an enlarged partial view of the distal end of the instrument of FIG. 58;

FIGS. 58B and 58C illustrate the operation of the oscillating blade of the cutting mechanism in the instrument of FIG. 58 under control of a trigger at the handle of the instrument;

FIG. 59 is another embodiment of the instrument of the present invention for use in breast biopsy having an imaging transducer at the instrument's distal end in which the instrument is passed over a guide wire located in the breast of a patient;

FIG. 59A is a partial view of the distal end of the instrument of FIG. 59;

FIG. 60 illustrates the instrument of FIG. 1 with optional integrated steering mechanism and imaging system;

FIG. 60A is an enlarged partial view of the distal end of the instrument of FIG. 60;

FIG. 61 is a perspective view of the instrument of FIG. 1 with another cutting mechanism having a linear blade for incising tissue to a controlled length and depth;

FIGS. 61A, 61B, and 61C are enlarged partial views of the distal end and the control knob at the proximal end of the instrument of FIG. 61 to illustrate the controlled advancement of the linear blade at the distal end of the instrument;

FIG. 61D is a side schematic view of the instrument of FIG. 61 with the linear blade shown at a retracted position at the distal end of the instrument; and FIGS. 61E and 61F are side schematic views of the instrument of FIG. 61 with the shaft partially broken showing the advancement of the linear blade at the distal end of the instrument by rotation of the control knob.

DETAILED DESCRIPTION OF THE INVENTION

Figure 1:
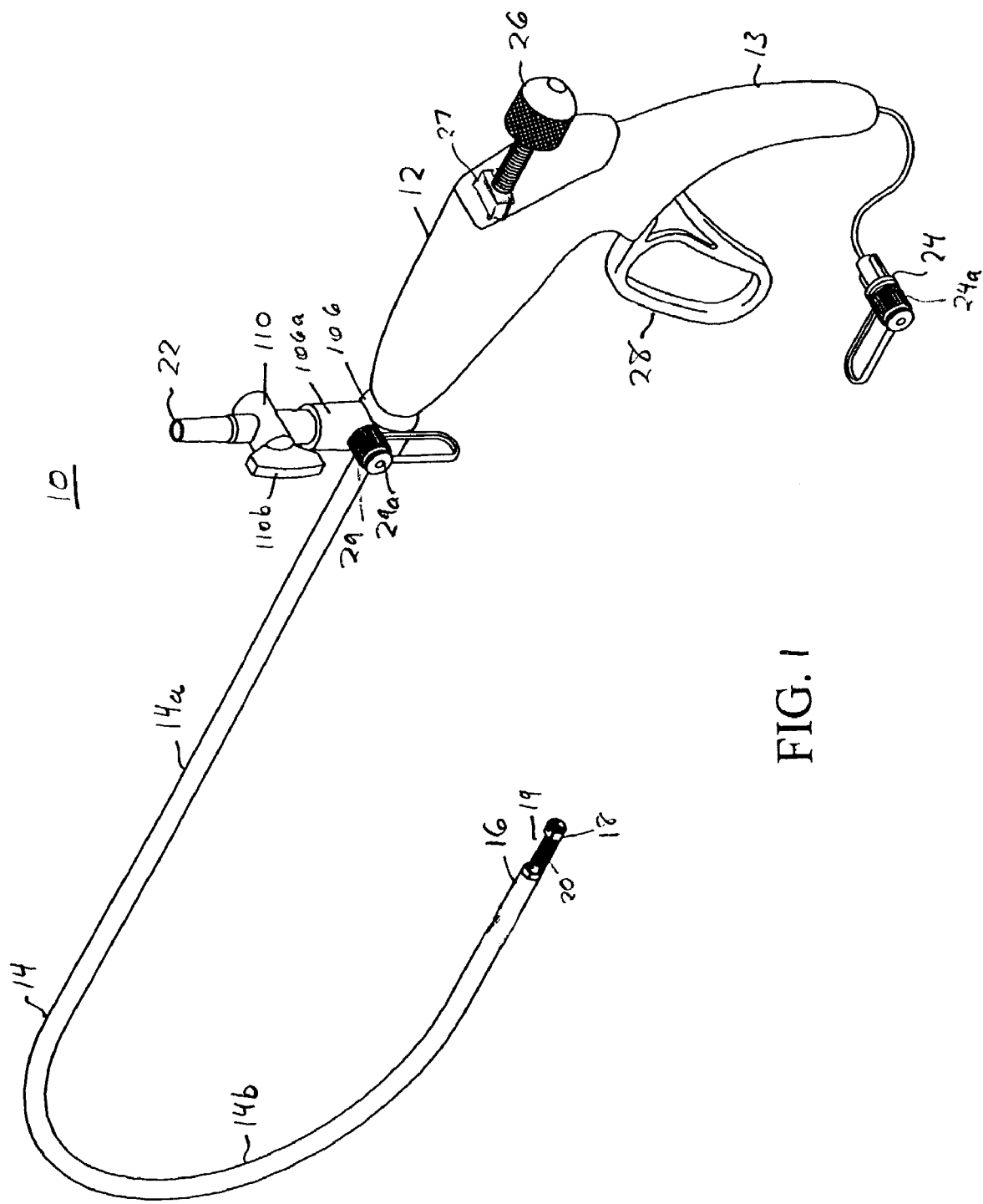
FIG. 1 is a perspective view of the instrument of the present invention.

Referring to FIG. 1, the instrument 10 of the present invention is shown having a housing 12 and a shaft 14 extending from the housing 12 to a distal end 16. The shaft 14 has a first rigid section 14a and then a second flexible section 14b to facilitate location of the distal end 16 along the curvature of a tubular structure, such as along the gastrointestinal tract, urinary tract, or vascular structures of a patient's body. The shaft 14 is of a cylindrical cross-sectional shape with an outer diameter enabling the shaft to be inserted in a tubular structure to locate the distal end 16 in such tubular structure of a patient. The housing 12 has a body shaped like a pistol having a handle portion 13, and may be made of a two-piece construction of molded plastic. At the distal end 16 of the shaft 14 is a distal housing 18 with an opening 19 to a cavity 20. The instrument 10 has a vacuum port 22 along shaft 14 for applying suction to the distal end 16, a turn screw 26 for controlling a cutting blade at the distal end 16, and a pivotable lever 28 to extend and retract two hollow needles at the distal end 16 capable of infusing fluid in tissue provided via a fluid insertion port 24. Another port 29 provides for insertion or removal of fluid through the same passages which communicate suction along shaft 14 to distal end 16. Ports 24 and 29 are shown closed in FIG. 1 by luer caps 24a and 29a, respectively.

Figures 2, 2A:
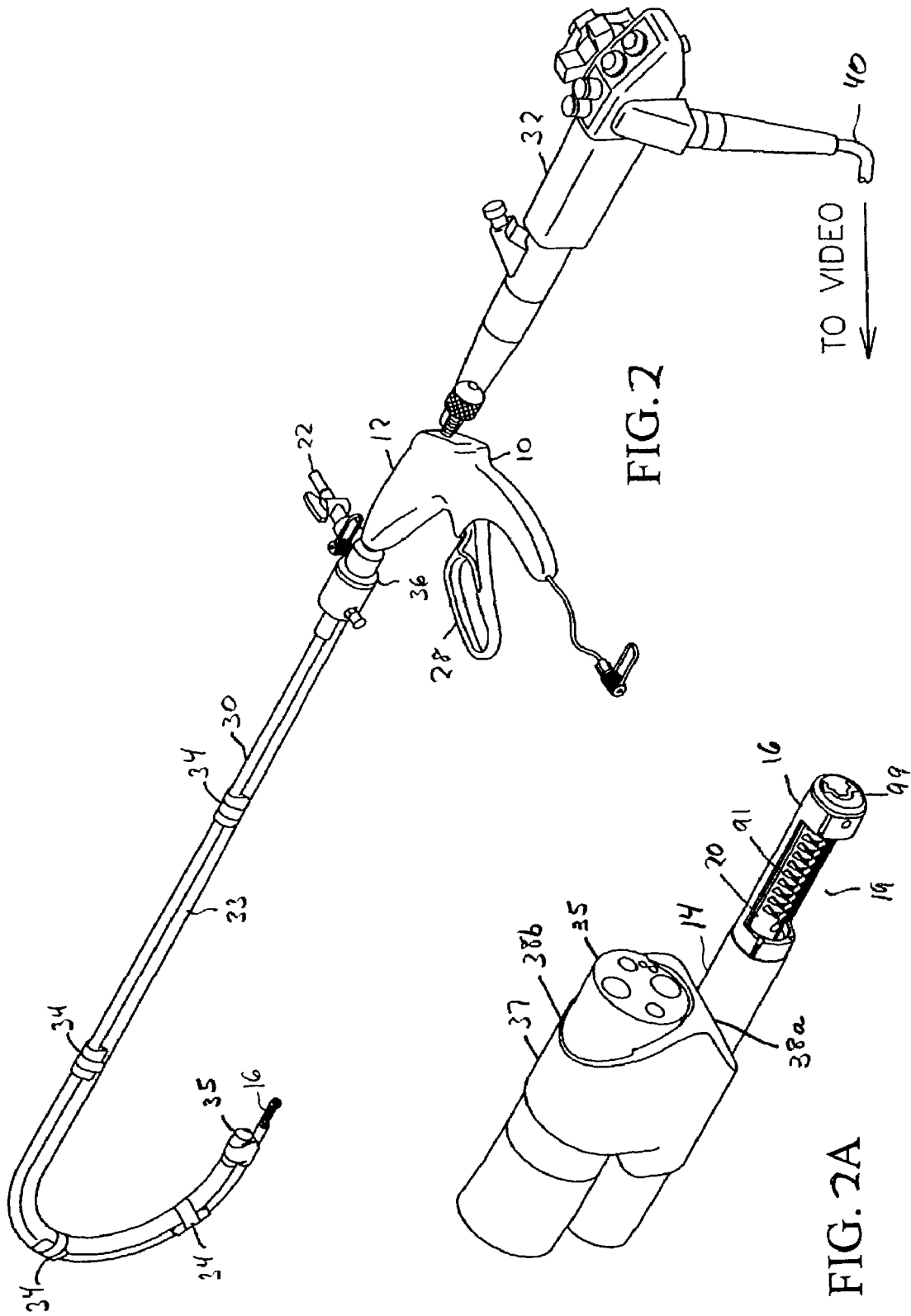
FIG. 2 is a perspective view of the instrument of FIG. 1 when inserted in an accessory tube coupled to the shaft of a flexible endoscope.
FIG. 2A is a partial view of distal end of shaft of the endoscope of FIG. 2 showing the attachment of a tube guide to the endoscope and the distal end of the instrument of FIG. 1.

As shown in FIGS. 2 and 2A, the instrument 10 may be used in conjunction with an accessory tube 30 coupled to an endoscope 32, such as a gastroscope, or any other type of flexible endoscope having a shaft 33. The accessory tube 30 is described in more detail in International Application No. PCT/US02/02791, filed Feb. 1, 2002, published under WO 02/062200 A2, and having priority to U.S. patent application Ser. No. 09/776,431, filed Feb. 2, 2001, and both applications are herein incorporated by reference. The instrument 10 may be inserted in the accessory tube 30 as shown in FIG. 2, and is removable from the accessory tube 12. The accessory tube 30 is useful, as it can be placed with the endoscope 32 in a tubular structure, such through the mouth of a patient into the gastrointestinal track, to facilitate location of the distal end of the instrument 10 to sites therein. In brief, the accessory tube 30 is coupled to the endoscope shaft 33 by tube guides 34, and has a cannula 36 with an opening through which shaft 14 of instrument 10 may pass into the accessory tube. At the distal end of accessory tube 30 is an attachment tip 37 having two openings 38a and 38b. One opening 38a receives the accessory tube 30, and the other opening 38b receives the distal end 35 of endoscope shaft 33. Attachment tip 37 is shown in more detail in FIG. 2A. Endoscope 32 may be a typical endoscope having a video display system coupled to its upper end, via a cable 40, to allow viewing of tissue from optics at its distal end 35, and in particular to assist an operator in locating and observing the instrument's distal end 16. Other viewing means may also be used for locating and observing the instrument's distal end 16, such as ultrasound, x-ray, or other imaging techniques. Although use of the instrument 10 is preferably used with the accessory tube 32, the instrument may be used without the accessory tube by placement of the shaft in a tubular structure of the body of a patient, or in an overtube as often used in endoscopic gastrointestinal procedures.

Referring to FIGS. 3-34, the assembly of the shaft and housing of the instrument is shown. In housing 12, lever 28 has two pins 42 extending into holes 43 in the sides of housing 12 upon which the lever 28 is pivotally mounted in the housing. Lever 28 has a portion which extends through an opening 44 in housing 12 to enable pivotal movement about pins 42. An extension spring 45 is provided which hooks at one end in a notch 46 of lever 28 and is wound at the other end around a pin 48 located in holes 49 in the sides of housing 12, such that the lever 28 is spring biased to retain the lever normally in a forward position, as shown for example in FIG. 1. The body of housing 12 has a front portion 12a providing a stop that limits the forward pivotal movement of lever 28.

Figure 23:
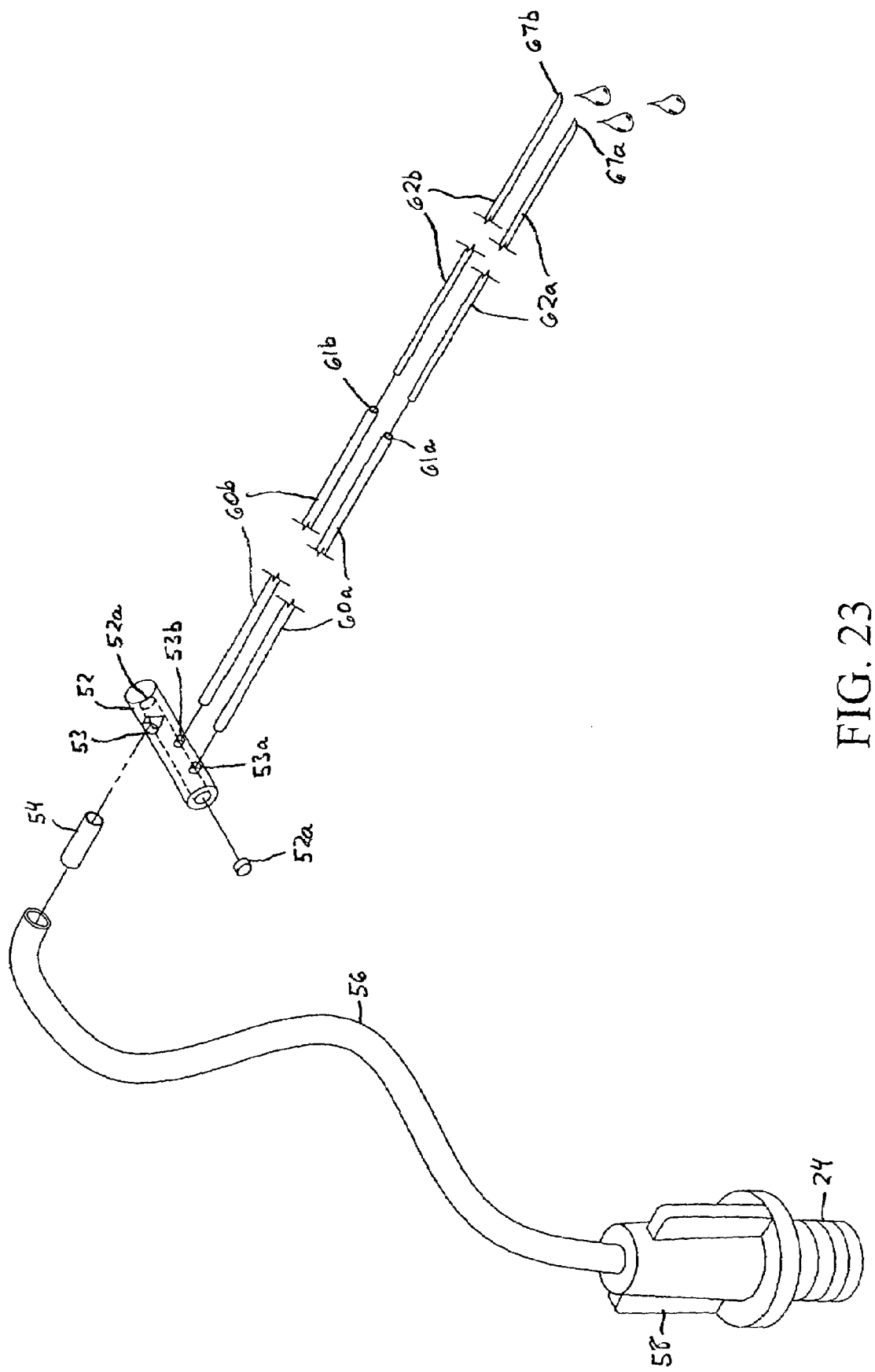
FIG. 23 is an exploded view of components of the instrument of FIG. 1 showing the path of fluid through needles to the distal end of the instrument.

A needle coupler 52 is received and mounted for rotation in a curved slot 50 at the top of the lever 28. As best shown in FIG. 23, the needle coupler 52 is a cylindrical tube having closed ends 52a, and has an opening 53 representing an inlet port, and two openings 53a and 53b representing outlet ports. One end of an inlet tube 54 is attached to the needle coupler 52, and other end of the inlet tube 54 is coupled into a fill tube 56. The fill tube 56 may be plastic tubing which extends from inlet tube 54 through an opening 12b of housing 12 into a hole 58a extending through a connector or fitting 58. Notches 12c (FIG. 4) along the interior of the left side of housing 12 may be provided for fill tube 56 as it extends through the housing.

Two needle tubes 60a and 60b are attached to needle coupler 52 at openings 53a and 53b, respectively, and two hollow needles 62a and 62b extend through the needle tubes 60a and 60b, respectively. These needles 62a and 62b extend from the needle coupler openings 53a and 53b through the assembly of the shaft 14 to their needle tips 67a and 67b, respectively, located at the distal end, as will be described below. Two parallel grooves of slots 51a and 51b are also at the top of the lever 28 and extend to slot 50. Needles 62a and 62b in their respective needle tubes 60a and 60b, respectively, extend from needle coupler 52 through slots 51a and 51b. Openings 53a and 53b are of the same diameter, but are smaller than the diameter of opening 52a, such that the needle coupler 52 under fluid pressure equally distributes the fluid to the needles. The outer diameter of the needles 62a and 62b are slightly less than the interior diameter of needle tubes 60a and 60b, and are fixed in the needle tubes 60a and 60b by attachment, such as welding or brazing, at the ends 61a and 61b of the needle tubes 60a and 60b, respectively. The needles may also, or instead, be attached to the needle tubes 60a and 60b at the site where each tube is attached to needle coupler 52. The inlet tube 54, needle coupler 52, and needle tubes 60a and 60b may be of stainless steel tubing, and may be attached, as described above, by welding or brazing.

Figure 3:
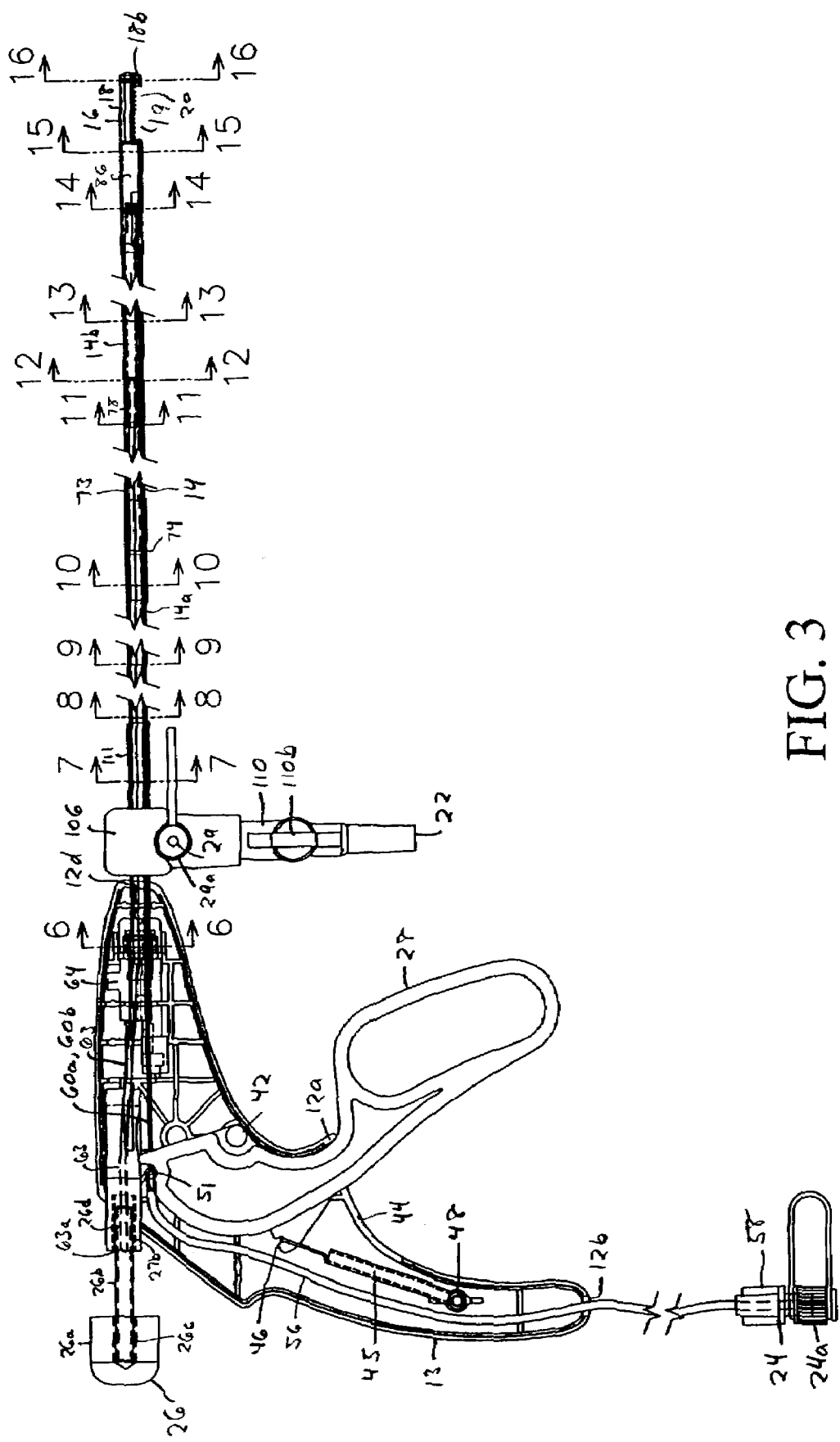
FIG. 3 is a side view of the instrument of FIG. 1.

Turn screw 26 represents a rotatable control knob having a textured rotatable cap 26a attached to a threaded rod or shaft 26b, which is inserted into a threaded hole 26c of the cap, as best shown in FIGS. 3, 27 and 28. One end 63a of drive tube 63 is inserted and attached, such as welded or brazed, into a hole 26d which at least partially extends into shaft 26b. A nut 27 is fixably mounted by two flanges 27a in the sides of housing 12, and has a threaded hole 27b extending there through for receiving shaft 26b. By rotating cap 26a, shaft 26b of the turn screw rotates in threaded hole 27b to rotate and move the drive tube 63 forward, or backward, depending on the direction of rotation.

In the housing 12, the needles 62a and 62b in their respective needle tubes 60a and 60b, pass from needle coupler 52 through an adapter 64. Adapter 64 is mounted in housing 12 by two flanges 64a. The adapter 64 has a bore 65 extending there through into which a needle spreader 66 is located. Needle spreader 66 has two channels 66a and 66b into which needles 62a and 62b in their needle tubes 60a and 60b are respectively located to increase the distance between the needles as they extend toward needle coupler 52, such that the needles in their needle tubes are properly aligned to slots 51a and 51b and needle coupler openings 53a and 53b. The drive tube 63, which extends from the turn screw 26, passes through the needle spreader 66 and adapter 64 along channel 66c of the needle spreader 66.

Next, a gasket member 68 has two holes 68a and 68b through which extends needles 62a and 62b, respectively, in their respective needle tubes 60a and 60b, and a hole 68c through which the drive tube 63 extends. The gasket member 68 may be made of medical grade rubber, such as Santoprene.

After gasket member 68, a longitudinal guide member 72 is provided with multiple tracks along its length, including two needle tracks 72a and 72b for needles 62a and 62b, in their respective tubes 60a and 60b. A track 72c in the guide member 72 is provided for the drive tube 63. The guide member 53 may be made of extruded flexible material, such as Tecoflex®, or other flexible plastic. Needle tubes 60a and 60b are movable in channels 66a and 66b of the needle spreader 66, holes 68a and 68b of gasket member 68, and tracks 72a and 72b of the needle guide 72 when needles are extended or retracted in the instrument. The drive tube 63 is also movable in channel 66c of the needle spreader, hole 68c of gasket member 68, and tracks 72c of the needle guide 72.

Figure 5:
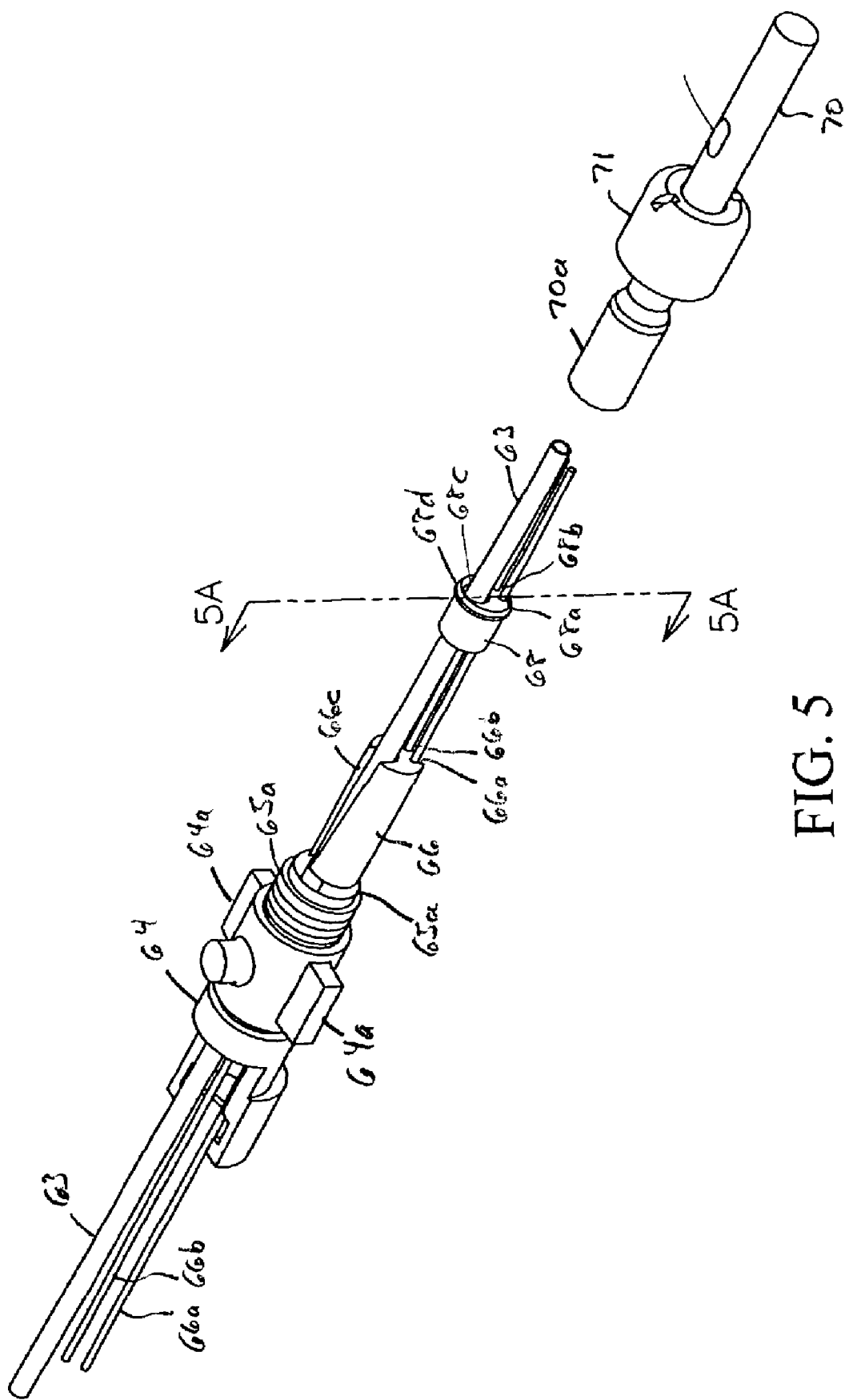
FIG. 5 is a detailed perspective view of the part of the instrument showing the adapter, needle spreader, and gasket member of the instrument of FIG. 1.

A rigid tube 70 is then provided into which the gasket member 68 is first loaded and then guide member 72. The D-shaped end 70a of tube 70 is registered into a corresponding shaped opening 65a to bore 65 in adapter 64, and a nut 71 with a threaded opening 71a screws onto the threaded end 64b of the adapter 64 to secure tube 70 to housing 12. The rigid tube 70 extends through opening 12d of housing 12. Tracks 72a, 72b, and 72c of the needle guide 72 each form a channel with the interior surface of rigid tube 70. Rigid tube 70 may be made of stainless steel, or other rigid material. FIG. 5 shows the gasket member 68 prior to being positioned in abutment to needle spreader 66 and in end 70a of rigid tube 70. Inside rigid tube 70, gasket member 68 has a ring 68d which frictionally engages the interior surface of tube 70 to form a seal therein.

Figure 5B:
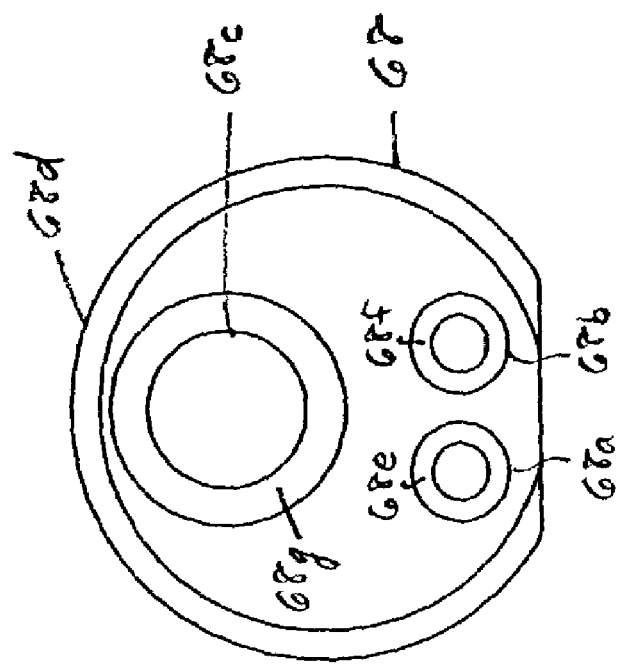
FIG. 5B is an end view of the gasket member of FIG. 5 without drive tube or needle tubes.
Figure 5A:
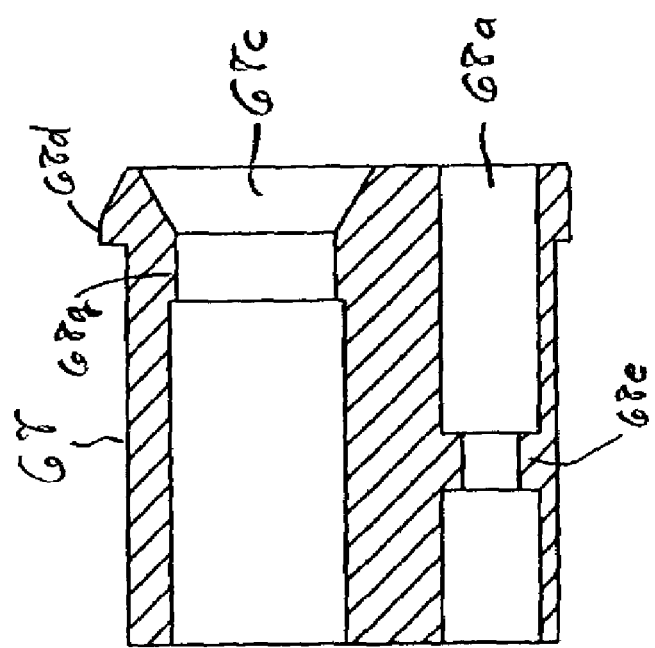
FIG. 5A is a cross-sectional view through lines 5A-5A of FIG. 5 showing the gasket member of the instrument of FIG. 1 without drive tube or needle tubes.
Figure 9:
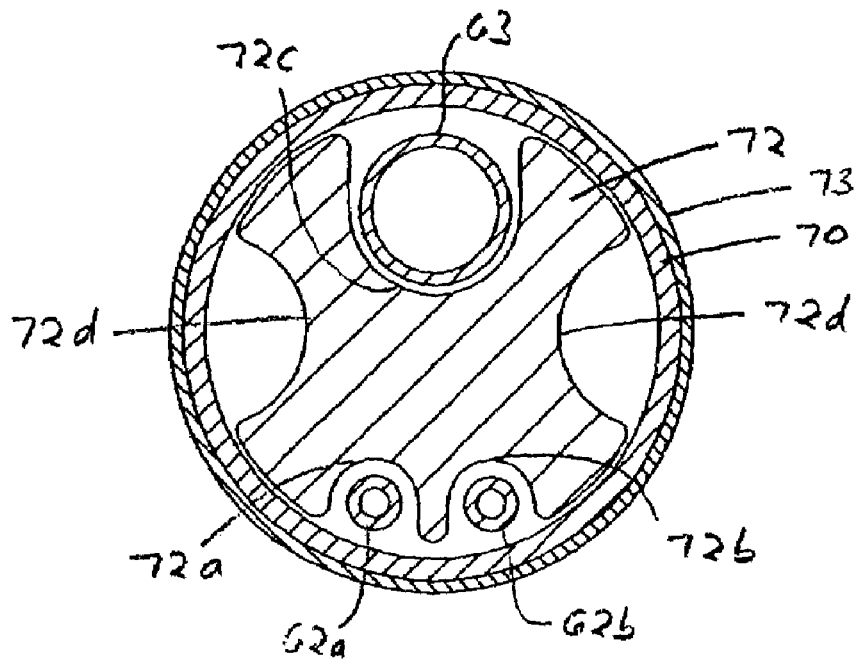
FIG. 9 is a cross-sectional view along lines 9-9 of the instrument of FIG. 3.

FIGS. 5A and 5B show gasket member 68 in more detail. Holes 68a and 68b are of a larger diameter than the needle tubes 60a and 60b, respectively, except for a small section of holes 68a and 68b where the diameter reduces to form annular flaps 68e and 68f, respectively, of gasket material which seal around needles 62a and 62b, respectively. This enables movement of the needles in their respective needle tubes 60a and 60b back and forth while maintaining a seal about each needle tube. Similarly, hole 68c of the gasket member 68 has an annular flap 68g to enable movement of the drive tube 63 as it is rotated back and forth which maintaining a seal around drive tube 63. One feature of the gasket member 68 is that it enables sealing the shaft 14, such that negative pressure, i.e., suction, may be selectively applied down the shaft, as described later below. A cross-section through gasket member 68 and adapter 64 is shown in FIG. 6, while FIG. 8 is a cross-section of shaft 14 with guide member 72.

Figure 11:
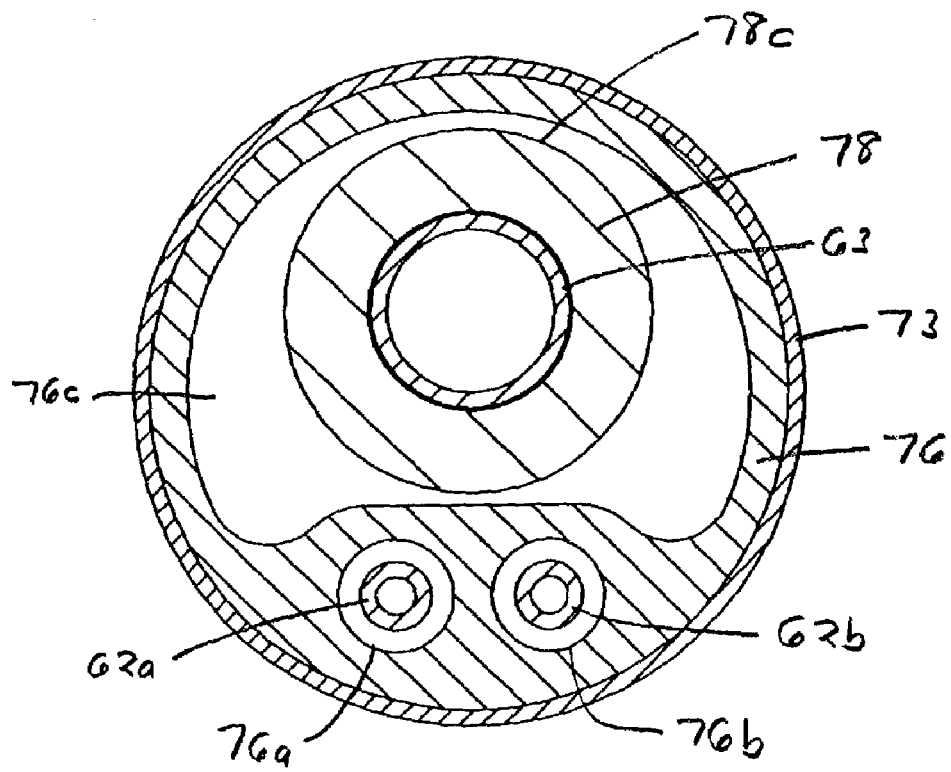
FIG. 11 is a cross-sectional view along lines 11-11 of the instrument of FIG. 3.
Figure 12:
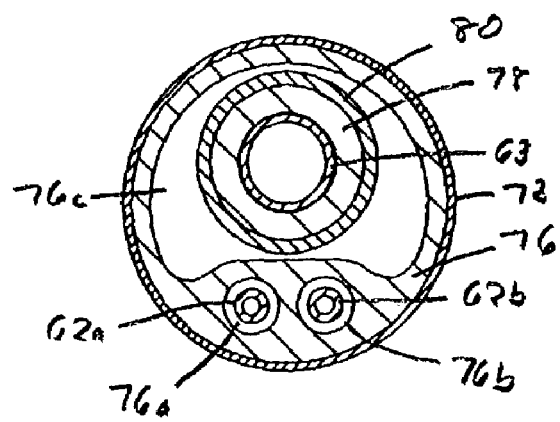
FIG. 12 is a cross-sectional view along lines 12-12 of the instrument of FIG. 3.
Figure 13:
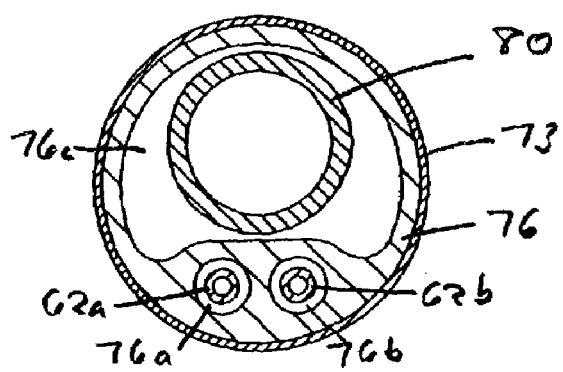
FIG. 13 is a cross-sectional view along lines 13-13 of the instrument of FIG. 3.

Next, a longitudinal flexible body 76 has an end 76d abutting end 70b of rigid tube 70. Flexible body 76 represents a three lumen tube having three longitudinal channels 76a, 76b, and 76c. Flexible body 76 may be formed of extruded flexible material, such as Tecoflex®, or other flexible plastic. As needle guide 72 ends at end 70b of the rigid tube 70, needles 62a and 62b exit and continue through channels 76a and 76b of the flexible body 76, respectively. Needle tubes 60a and 60b extend from needle coupler 52 and end along the needle guide 72 prior to end 70b of rigid tube 70, where the needles 62a and 62b exit their tubes 60a and 60b and continue down shaft 14, as illustrated in the cross-section of FIG. 9. Also, the drive tube 63 exits end 70b of the rigid tube 70, and is coupled to flexible tube 80, via coupler member 78, after entry into channel 76c of the flexible body 76. The flexible tube 80 represents a flexible tube, such as of polyurethane or other plastic, having a mesh or weave of metal. The coupler member 78 represents a cylindrical metal tube 78a having a circular opening 78b extending there through, and an annular flange 78c at one end. The drive tube 63 extends into opening 78b of tube 78a, and attached thereto, such as by welding or brazing. The end 80a of flexible tube 80 is received onto other end 78d of the coupler member 78 until annular flange 78d, and held thereupon by frictionally engagement provided by the expansion of the flexible tube's mesh, which prevents forward movement of the flexible tube 80 with respect to coupler member 78, while flange 78d of the coupler member 78 provides a stop limiting backward movement of flexible tube 80 upon the coupler member. A cross-section of the shaft through the flexible body 76 at flange 78c is shown in FIG. 11, and then at end 78c in FIG. 12. The flexible tube 80 continues through flexible body channel 76c to the distal end 16, as illustrated in the cross-section of the shaft in FIG. 13. The needles 62a and 62b are movable, and flexible tube 80 is rotatable forward and backward along their respective channels 76a, 76b, and 76c in the flexible body 76.

Figure 10:
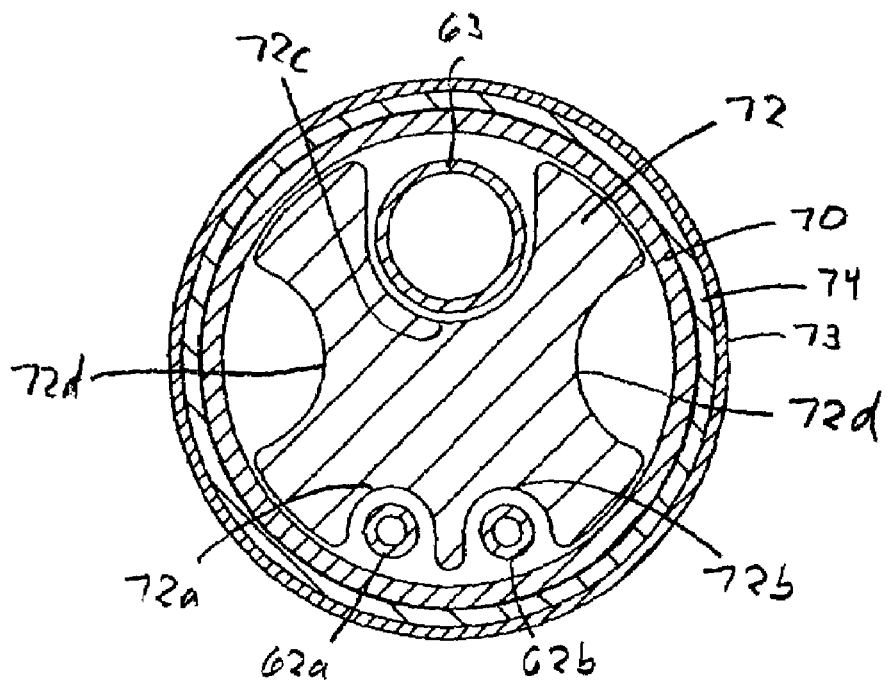
FIG. 10 is a cross-sectional view along lines 10-10 of the instrument of FIG. 3.

A splice tube 74 couples the flexible body 76 to the rigid tube 70, in which the splice tube 74 is slid over the abutting ends of the flexible body and rigid tube, and partial extends over both flexible body and rigid tube. As the outer diameter of the flexible body 76 is substantially the same as the outer diameter of the rigid tube 70 at end 70b where they abut each other, their ends substantially align with each other. The splice tube 74 may be composed of heat shrinkable material, such that it is secured in place by application of heat. Optionally, adhesive material may also be used which can be wicked under the splice tube 74. A cross-section of the shaft 14 at the splice tube 74 over rigid tube 70 is shown in FIG. 10.

The end 76e of flexible body 76 is coupled to the distal housing 18 at the distal end 16, as best shown in FIGS. 17, 17A, 17B and 34. Distal housing 18 is approximately cylindrical in shape and has a circular opening 88 extending there through between its ends 88a and 88b, and two side openings 18a and 19 to opening 88, where opening 19 is to cavity 20 of distal end 16. The flexible body 76 extends into circular opening 88 at end 88a of the distal housing 18, and is attached thereto, such as by adhesive or staking. The needles 62a and 62b then exit the flexible body 76 and increase in separation as they enter parallel longitudinal channels or tracks 90a and 90b, respectively, which extend along the exterior surface of distal housing 88, but are discontinuous at opening 19.

Figure 14:
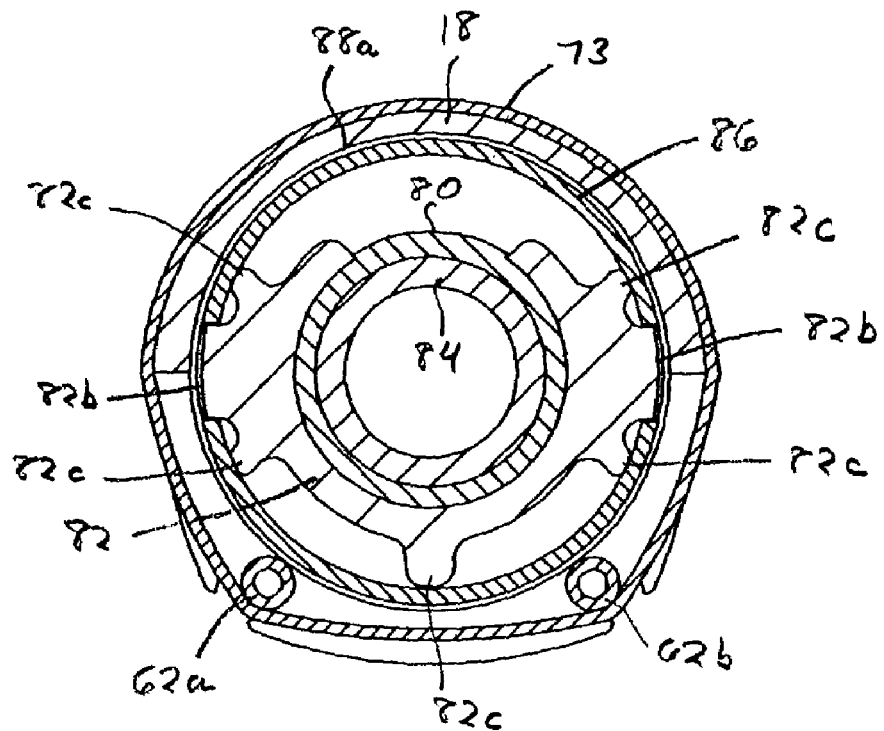
FIG. 14 is a cross-sectional view along lines 14-14 of the instrument of FIG. 3.
Figure 15:
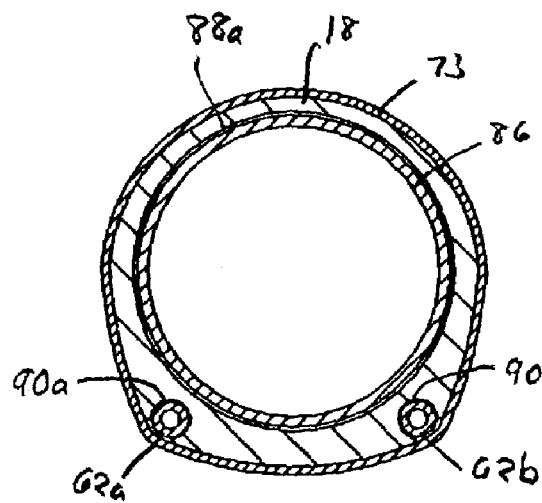
FIG. 15 is a cross-sectional view along lines 15-15 of the instrument of FIG. 3.

The flexible tube 80 also exits the flexible body 76 in the distal housing opening 88, where it is then is coupled to a tube blade 86 by a coupler member 82 and an expander tube 84. As best shown in FIGS. 27-29, such coupling is provided by end 80b of flexible tube 80 being located in the opening 82a of coupler member 82. Opening 82a has a diameter slightly less that the outer diameter of the flexible tube 80. An expander tube 84 is then located in flexible tube 80. The expander tube 84 has an outer diameter about the same as the interior diameter of the flexible tube 80, thereby expanding the flexible tube to force it against the interior surface of opening 82a of coupler member 82, thereby mechanically connecting the coupler member 82 to the flexible tube 80. The coupler member 82 has outwardly extending protruding ribs or ridges. Two of these ridges form rectangular keys 82b which are received into corresponding openings 86a of the tube blade 86 to attach and lock the tube blade 86 to coupler member 82. The remaining ridges 82c of the coupler member 82 lie against the interior surface of the tube blade 86 to assist in maintaining the cylindrical shape of the tube blade. FIG. 14 is a cross-section of the coupling of the flexible tube 80 to the tube blade 86, while FIG. 15 shows a cross-section of the distal end of the tube blade 86 after such coupling. The tube blade 86 may represent a thin stainless steel tube having a sharp edge 87 capable of cutting tissue. As opening 88 has a diameter slightly larger than that of the outer diameter of tube blade 86, the tube blade is rotatable and translatable forward and backward in the distal housing 18.

Figure 30:
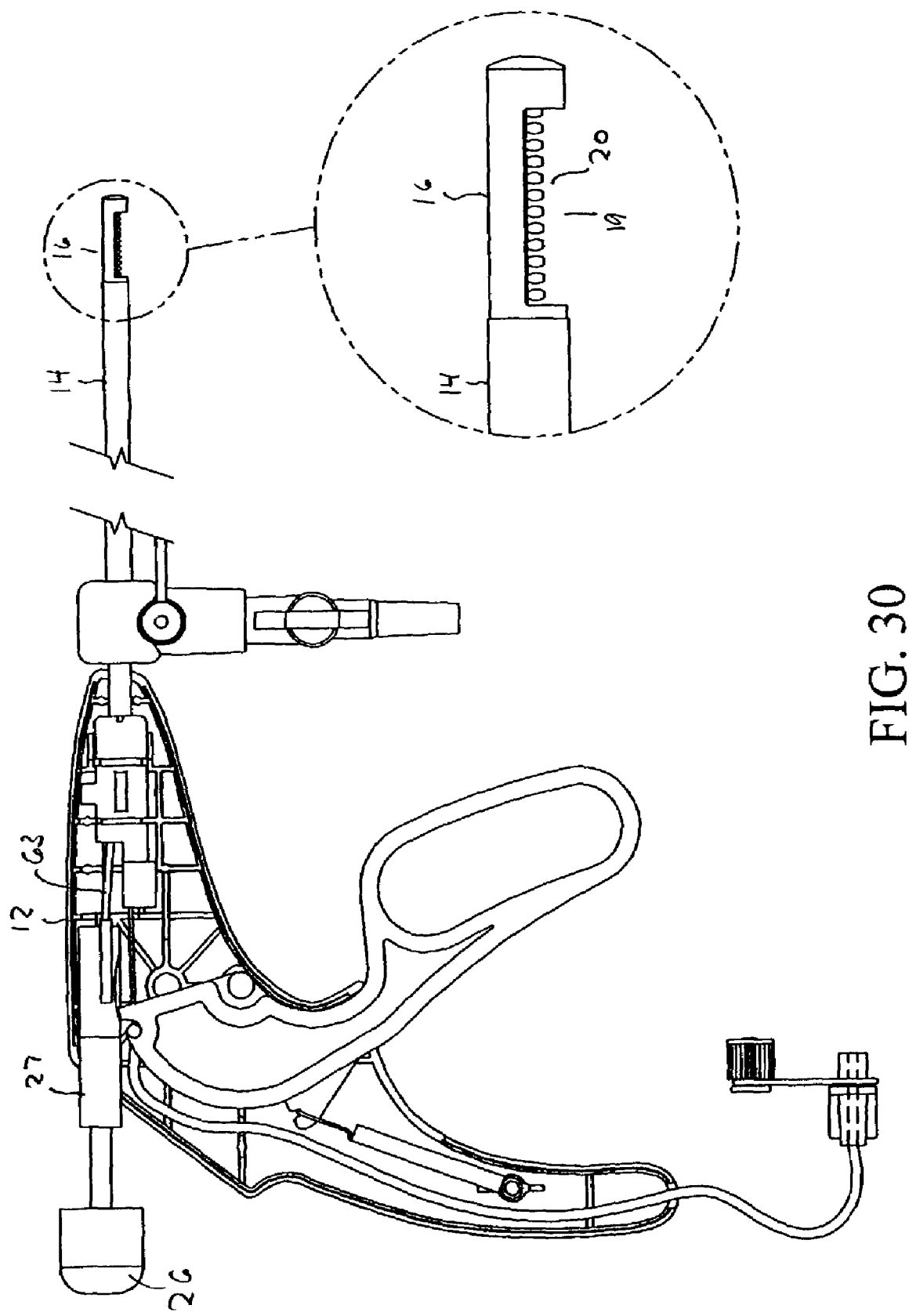
FIGS. 30, 31, 32, and 33 are side views of the instrument of FIG. 1 illustrating the operation of the instrument for driving and retracting a cutting blade at the distal end of the instrument.
Figure 31:
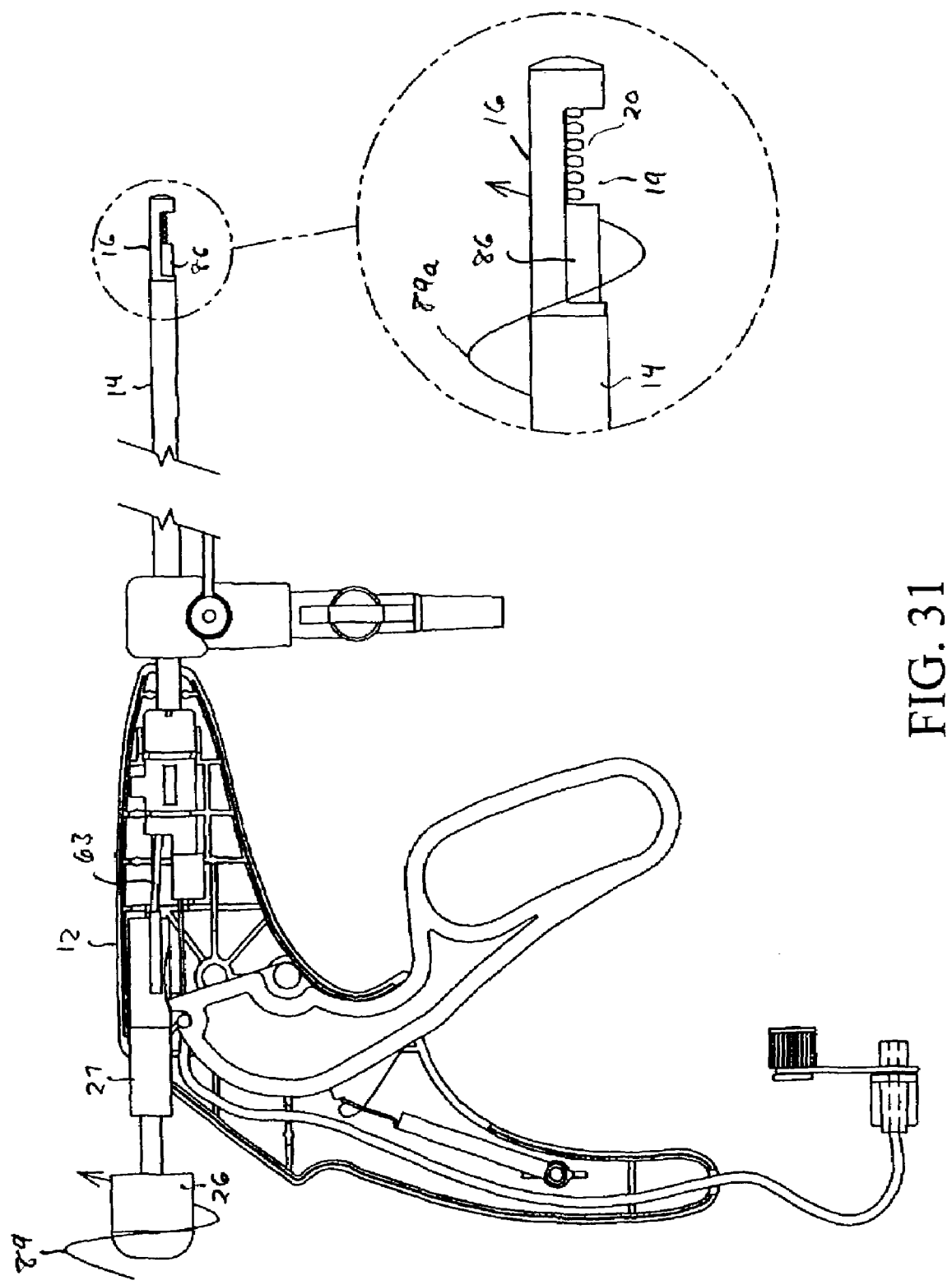
Figure 32:
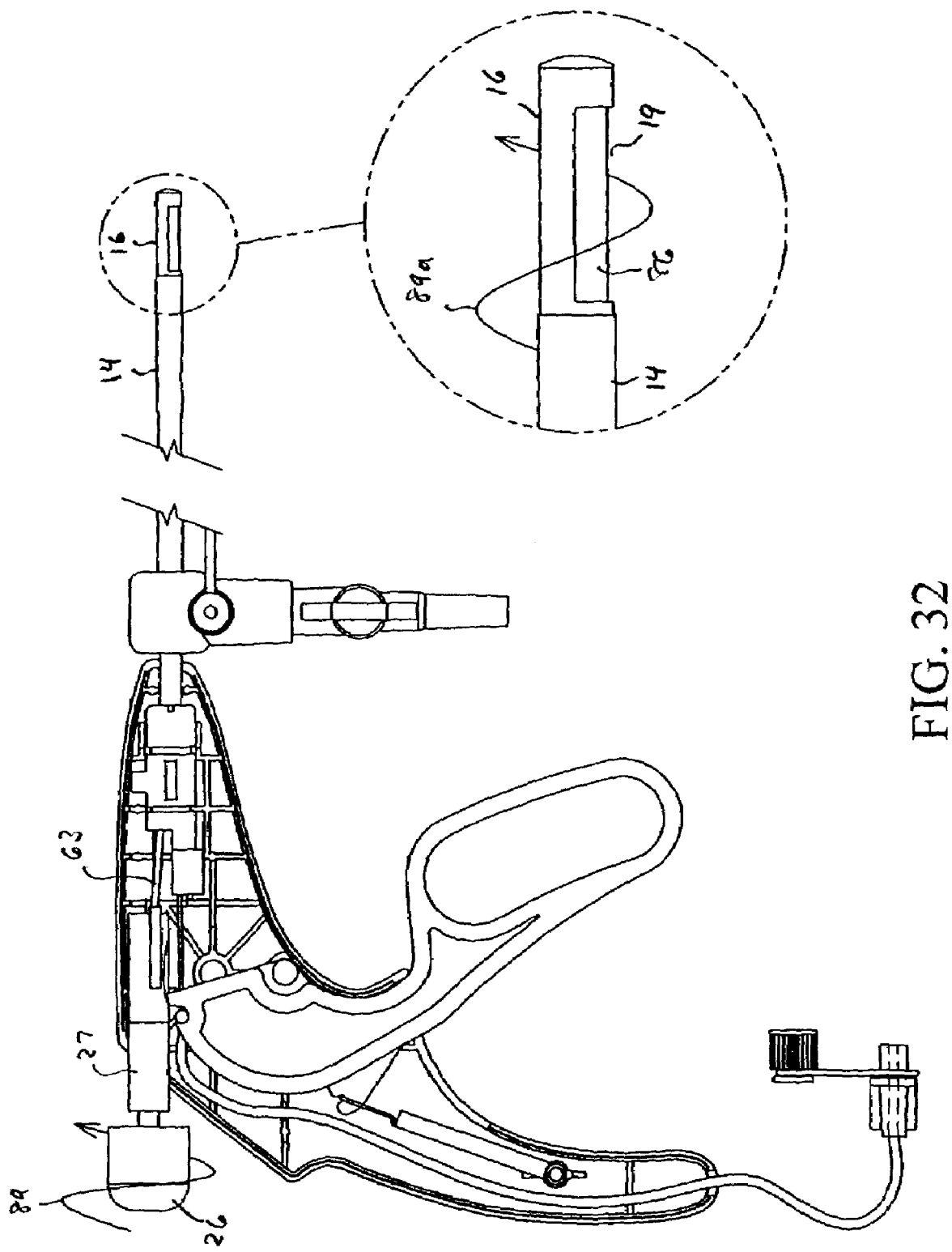
Figure 33:
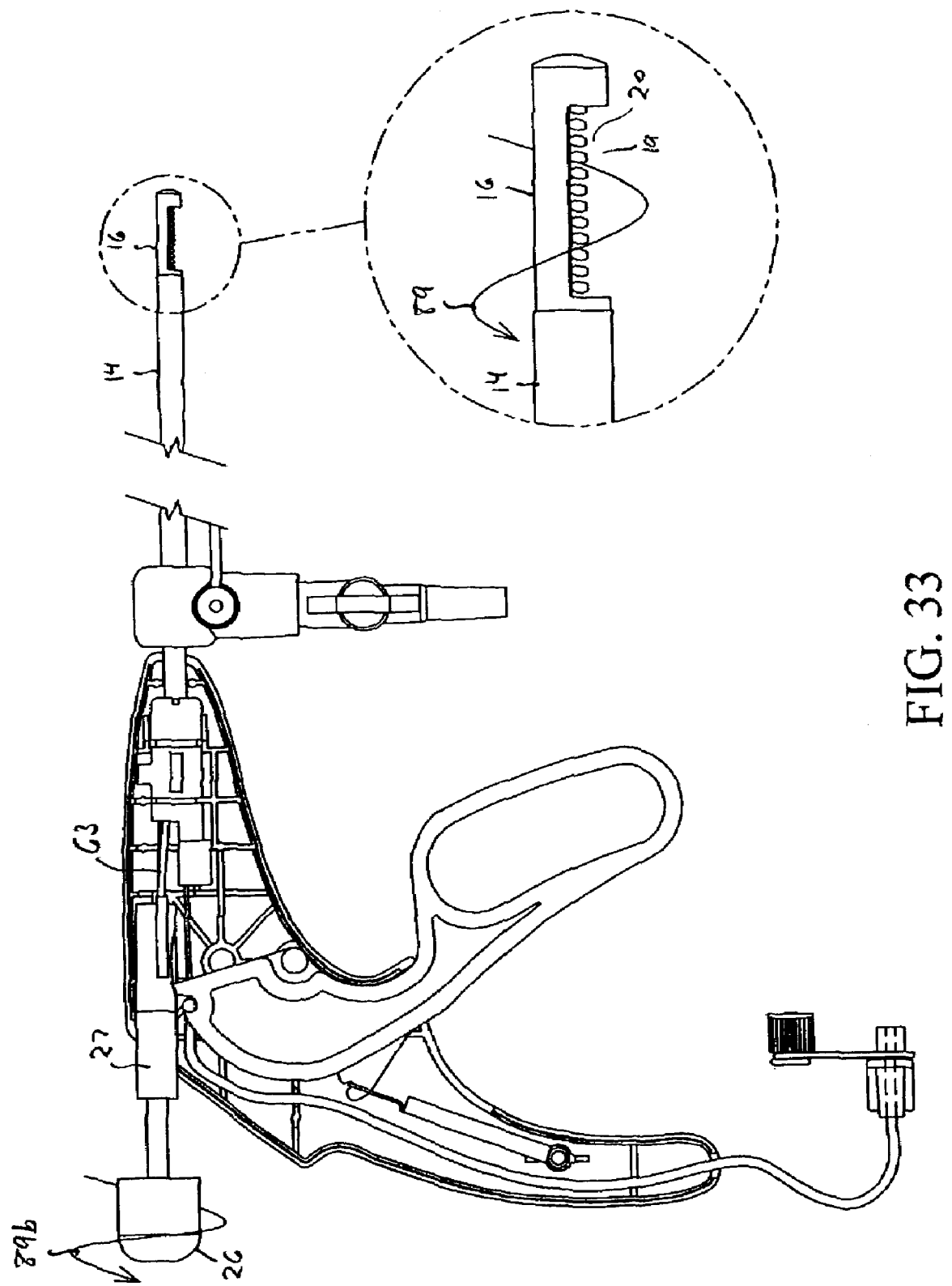
Figure 34:
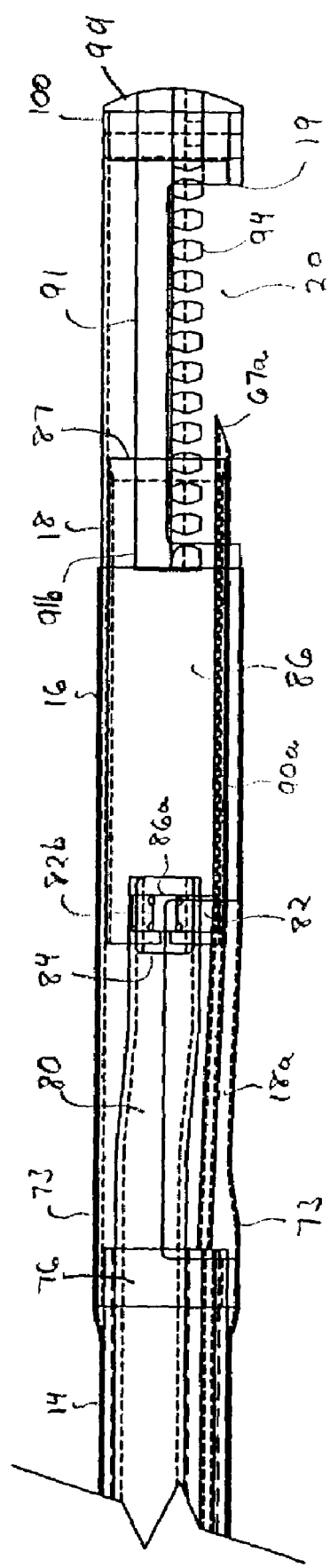
FIG. 34 is a cross-sectional side view of the distal end of the instrument of FIG. 1 with the needles partially extended.
Figure 35:
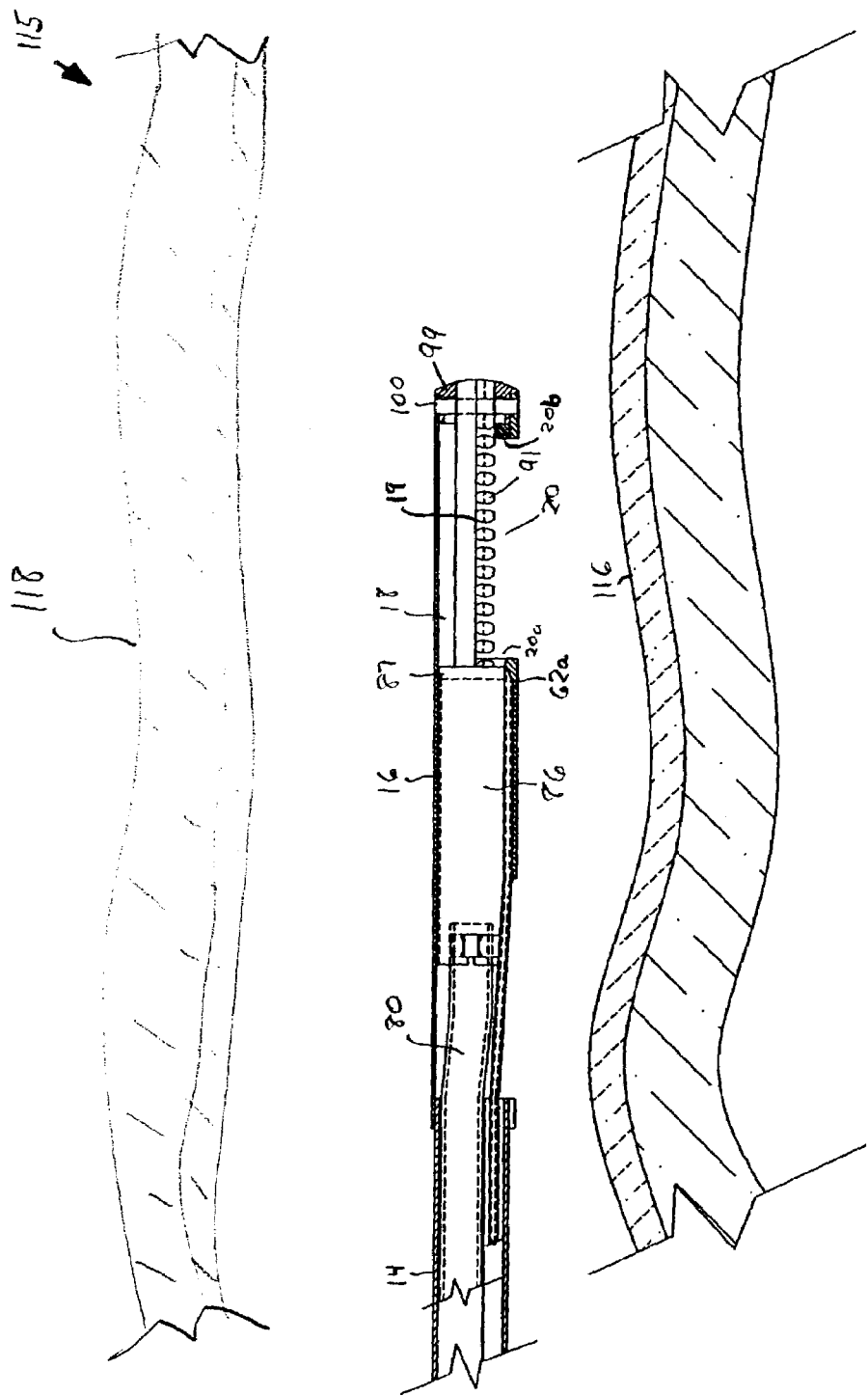
FIGS. 35, 36, 37, 38, 39, 40, 41, 42, 43, and 44 are side views illustrating the operation of the instrument of FIG. 1 at the distal end thereof.

Referring to FIGS. 30-33, the tube blade 86 when in a retracted position in the distal end provides an open cavity 20 (FIG. 30). Rotating turn screw 26, as indicated by arrow 89, to first translate rotation to the drive tube 63, which then translates the rotation to the flexible tube 80, via coupler member 78, and finally to the tube blade 86, via coupler member 82, to provide rotation of the tube blade with forward translation in opening 88 of the distal housing 18, as indicated by arrow 89a (FIG. 31), until in a fully extended position to close cavity 20 (FIG. 32). When the turn screw 26 is then rotated in the opposite direction, as indicated by arrow 89b, rotation is similarly translation to the turn blade 86 in the opposite direction, as indicated by arrow 89c to its retracted position in the distal end (FIG. 33).

Distal housing 18 further has a grated manifold member 91 which extends from end 88a through cavity 20 partially though the distal housing. Manifold member 91 has a surface 91e facing opening 19 with one or more openings representing a grate. As best shown in FIGS. 17, 17A, 17B, and 45, manifold member 91 has two sets of projections 92, each set extending upwards from opposing ledges 98 in two side walls 93, and then curve towards each other along a circular arc generally in a direction of opening 19. The gaps formed between adjacent projections 92 provide openings (or slots) 94 along the same side wall, and the gap formed between the two sets of projections 92 provides a central opening (or slots) 95. The openings 94 are distributed along surface 91 e in the manifold member, and preferably equally distributed. End 91b of the manifold member 91 is located before cavity 20, and the other end 91a of the manifold member 91 is located at distal tip 18 of distal housing 18. The side walls 93 curve as they extend in a direction opposite that of extending projections 92, generally parallel to the interior circumferential surface of the distal housing 18, and form ribs 96 about a central opening 97. Also, the projections 92 extending from each of walls 93 meet and are continuous at each of the ends 91a and 91b of manifold member 91, and having at such ends a continuous circular arc profile without central opening 95, such that a channel 97a to central opening 97 is provided at end 91b. Openings 94 and 95 in surface 91e can provide inlets through which suction can be communicated sufficient to engage tissue when located adjacent the instrument's distal end 16, as described below, whereby surface 91e of the manifold represents a tissue engaging surface. Other manifolds or suction transfer means could also be used with different oriented openings towards opening 19 sufficient for distributing suction in cavity 20.

Figure 16:
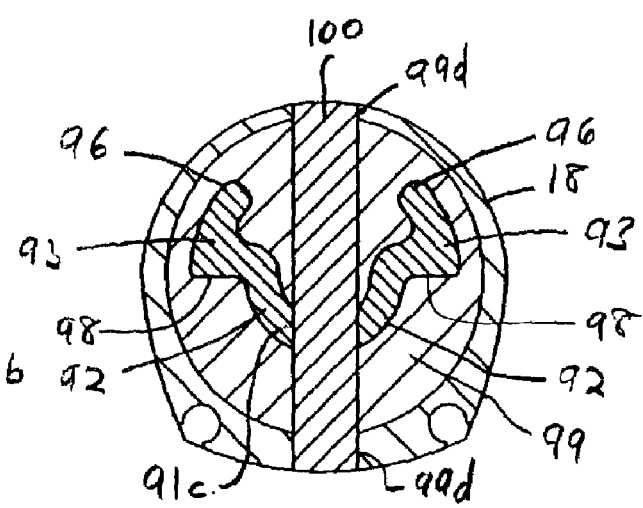
FIG. 16 is a cross-sectional view along lines 16-16 of the instrument of FIG. 3.
Figure 20:
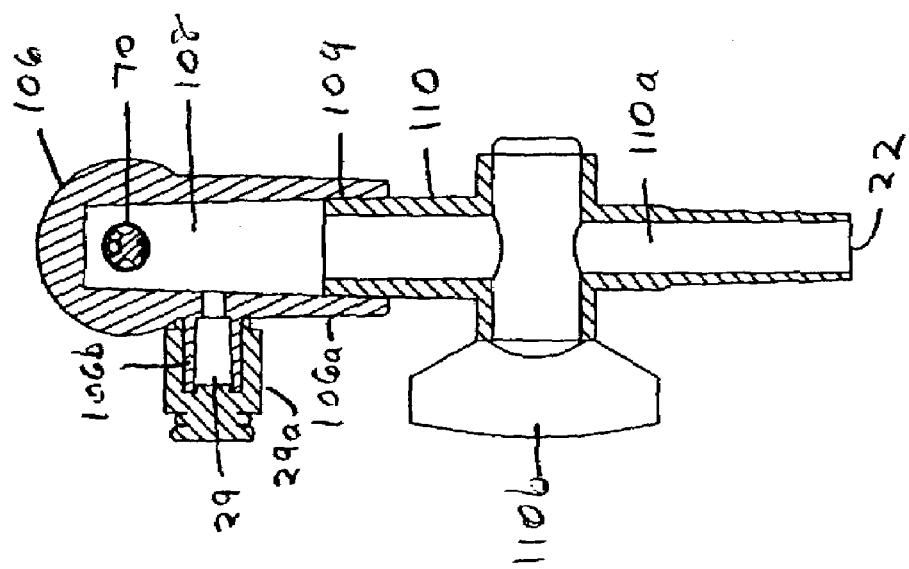
FIG. 20 is a cross-sectional view along lines 20-20 of FIG. 19.
Figure 19:
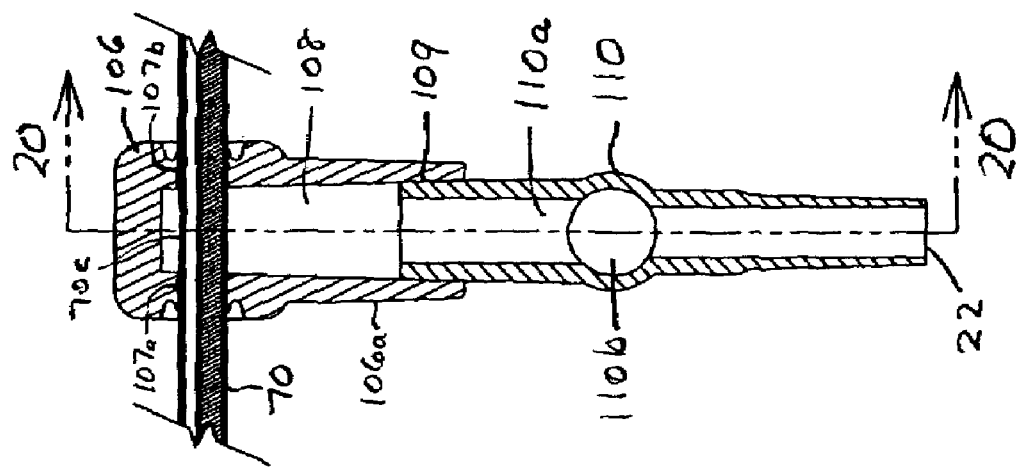
FIG. 19 is a cross-sectional view along lines 19-19 of FIG. 18.

The distal tip 18b of the distal end 16 is provided by a cap 99 having a rounded edge 99a along an annular flange 99b. The cap 98 is sized to be received into opening 88 of the distal housing 18, such that cap edge 99a abuts edge 88c of the distal housing, and a cutout or opening 99c of cap 98 receives end 91a of the grated manifold member 91. A pin 100 extends through two holes 99 in the cap 99 and through a hole 91c in the manifold member 91 at its end 91a, and through two holes 102 at end 88a of the distal housing, to retain the manifold member 91 and the cap 99 at distal end 16. Preferably, the surface 99e of the cap about opening 88 lies continuous with surface 91d of the manifold member 91, such as may be provided by polishing or grinding such surfaces when assembled together. In this manner, the manifold member 91 is only attached to the distal housing at its end 91a. A back stop 104, such as a C-shaped piece of rubber, is located in cap 99 adjacent end 91a of the manifold member 91. The back stop 104 limits the forward extent of the tube blade 86 when fully extended in the distal housing 18, and minimizes dulling of the blade if extended to pin 100. FIG. 16 shows a cross-section of distal end 16 through pin 100.

The particular contour curvature or profile of the tissue engaging surface provided by surface 91e of the manifold member 91 is defined by projections 92 about central opening 95 and longitudinal ledges 98, as shown in FIGS. 16, 17, 17A, 17B and 45, and is selected in accordance with the depth of the tissue to be cut by the instrument. The depth of the cut is also controlled by the size of the cavity 20 with respect to surface 91e. Other dimensions of length, width, and overall shape of the tissue are primarily a function of the size of the cavity 20 and extent of opening 19 in the distal housing 18, but may also be determined by the contour of surface 91e. Thus, different sizes and depths of tissue may be removed by instrument 10 by changing the size of cavity 20 and/or the contour of surface 91c of manifold member 91.

The manifold member 91 is sized smaller than the interior diameter of opening 88, thereby providing a path for travel of the tube blade 86 across cavity 20 over end 91b of the manifold member 91. The distal housing 20 and manifold member 91 may be manufactured using electrical discharge machining (EDM) processes. Manifold member 91 may alternatively be made of porous material, e.g., Porex®, manufactured by Porex Corp. of Fairfax, Ga., which could be injection molded, for transferring suction to properly engage the tissue at the specimen harvest site. Opening 18a is optional and can be used to assist in assembly of components in the distal housing, and is later sealed by shrink tube 73, as will be described below.

Referring to FIGS. 18-22, suction can be communication via port 22 of a vacuum housing 106 coupled to shaft 14 to the distal end 18. The vacuum housing 106 is coupled to rigid tube 70, and has two openings 107a and 107b to a chamber 108 through the rigid tube 70 extends. The diameter of openings 107a and 107b is smaller than the outer diameter of rigid tube 70, such that material about openings 107a and 107b sealingly engages the rigid tube. The vacuum housing 106 also has an extension 106a with a threaded opening 105 to chamber 108 for receiving a valve or stop cock fitting 110. The valve 110 has an opening 110a extending there through from chamber 108 to port 22, and a switch 110b to a valve therein to open and close such valve, as indicated by arrow 114, to control the flow of air (under negative pressure) passing from chamber 108 via opening 110a. A source of suction (or partial vacuum) may be coupled to port 22. Vacuum housing 106 has another extension 106b to an opening 112 to port 29. A luer cap 29a is provided upon port 29 so as to close the port 29 when not needed. A ring 29b may couple the luer cap 29a to port 29.

The rigid tube 70 has two openings 70c along opposite sides of the tube 70 which are in communication with chamber 108, and such openings 70c are aligned with two channels 72d of the needle guide 72 in rigid tube 70. The vacuum housing 106 is rotatable around the rigid tube 70, but is limited in longitudinal movement along shaft 14 by housing 12, and a stop tube 111 disposed over the rigid tube adjacent opening 107b. The stop tube 111 may be composed of heat shrinkable material, such that it is secured in place by application of heat. The vacuum housing 106 and valve 110 may be made of molded polypropylene plastic or other plastic. A cross-section of the shaft 14 through the stop tube 11 is shown in FIG. 7.

After the shaft is assembled as described above with vacuum housing 106 upon the rigid tube 70, a plastic shrink wrap layer or tubing 73 is installed from over the stop tube 111 until opening 19 of the distal housing 18, and then shrunk in response to applied heat onto exposed surfaces of shaft 14. Alternatively, the shrink tubing 73 may be applied upon the rigid tube 70 prior to locating vacuum housing 106, and extend from housing 12 until opening 19, and then the tubing 73 is cut about rigid tube openings 70c, and then the vacuum housing 106 and stop tube 111 placed over tubing 73. The flexible body 76 substantially defines the extent of the flexible section 14b of shaft 14, while the rigid tube 70 substantially defines the extent of the rigid section 14a of the shaft 14 after exiting housing 12.

Figure 21:
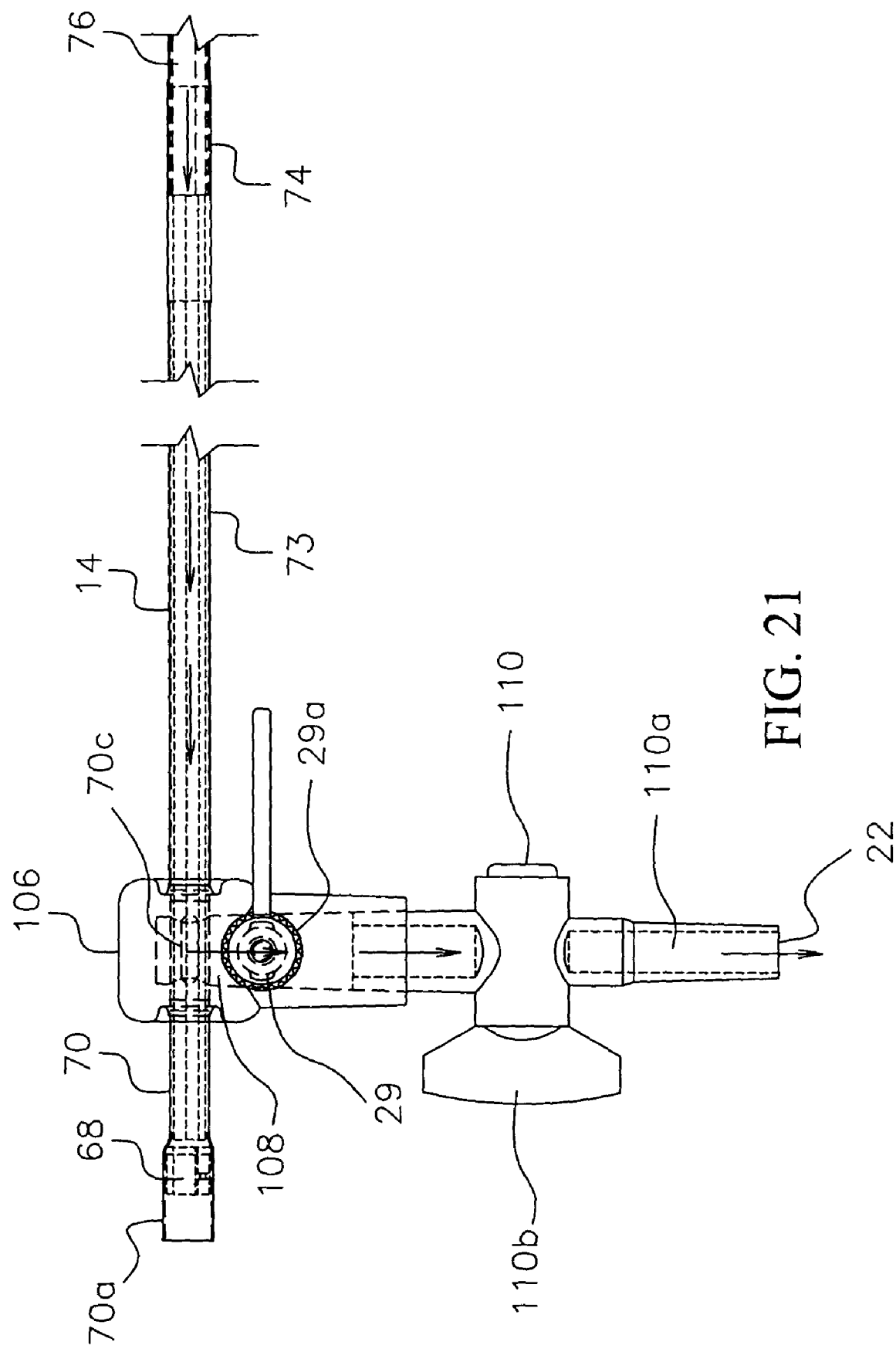
FIGS. 21 and 22 illustrate the operation of the instrument of FIG. 1 to communicate suction to its distal end.
Figure 22:
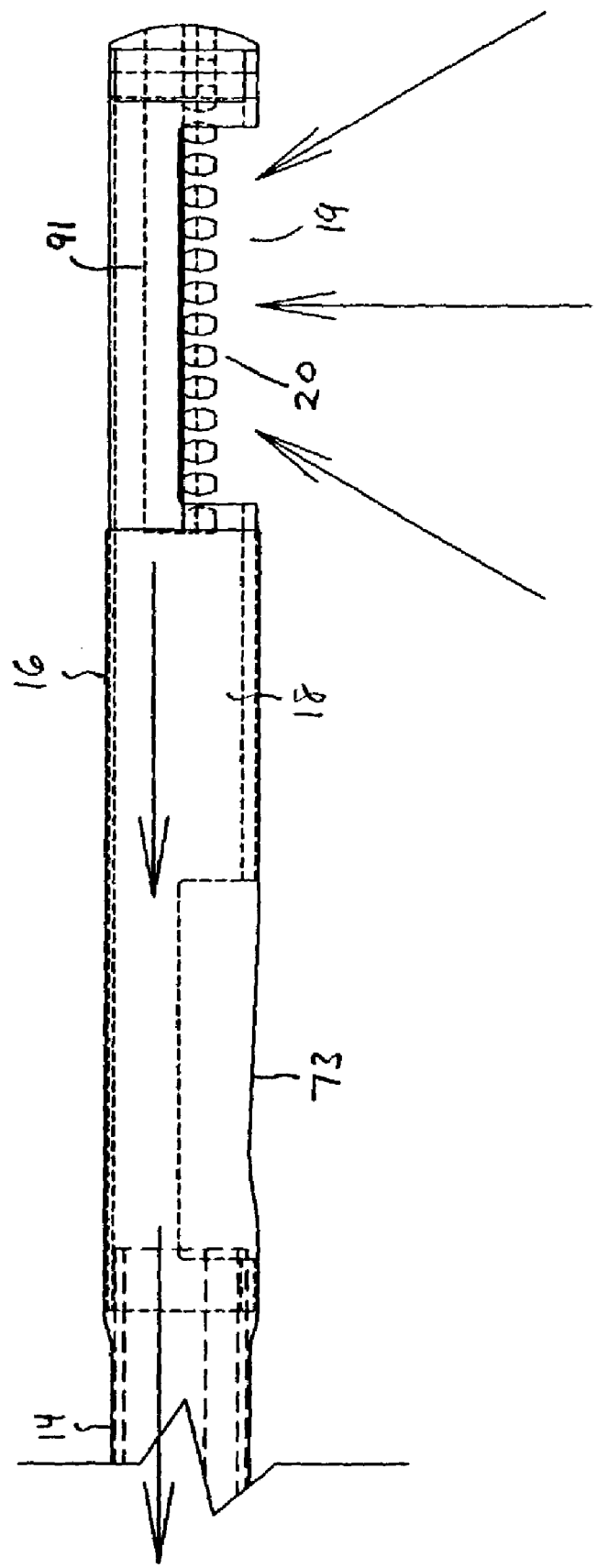

Referring to FIGS. 21 and 22, suction can be communicated via port 22 through chamber 104, through openings 70c and through the rigid tube 70 along needle guide 72, via needle guide channels 72d, and through open spaces or regions about the needle tubes (or needles once exiting such needle tubes) and drive tube 63. After the needle guide 72, suction continues to be communicated along the flexible body 76, including longitudinal channels 76d, and through all open spaces or regions of the flexible body about the needles and flexible tube in channels 76a-76c, to opening 88 of the distal housing and then to cavity 20. In distal end 16, suction is available through all open spaces of cavity 20, such as through the tube blade 86, needle channels 90a and 90b, openings 94 and 95 of manifold member 91, and gaps 124 between the sides of the manifold member 91 and the interior of the distal housing 18. The direction of air flow is represented by arrows in FIGS. 21-22. Port 29 provides for insertion or removal of fluid through the same passages which communication suction along shaft 14 to distal end 16, when suction is not being provided to shaft 14.

Figure 24:
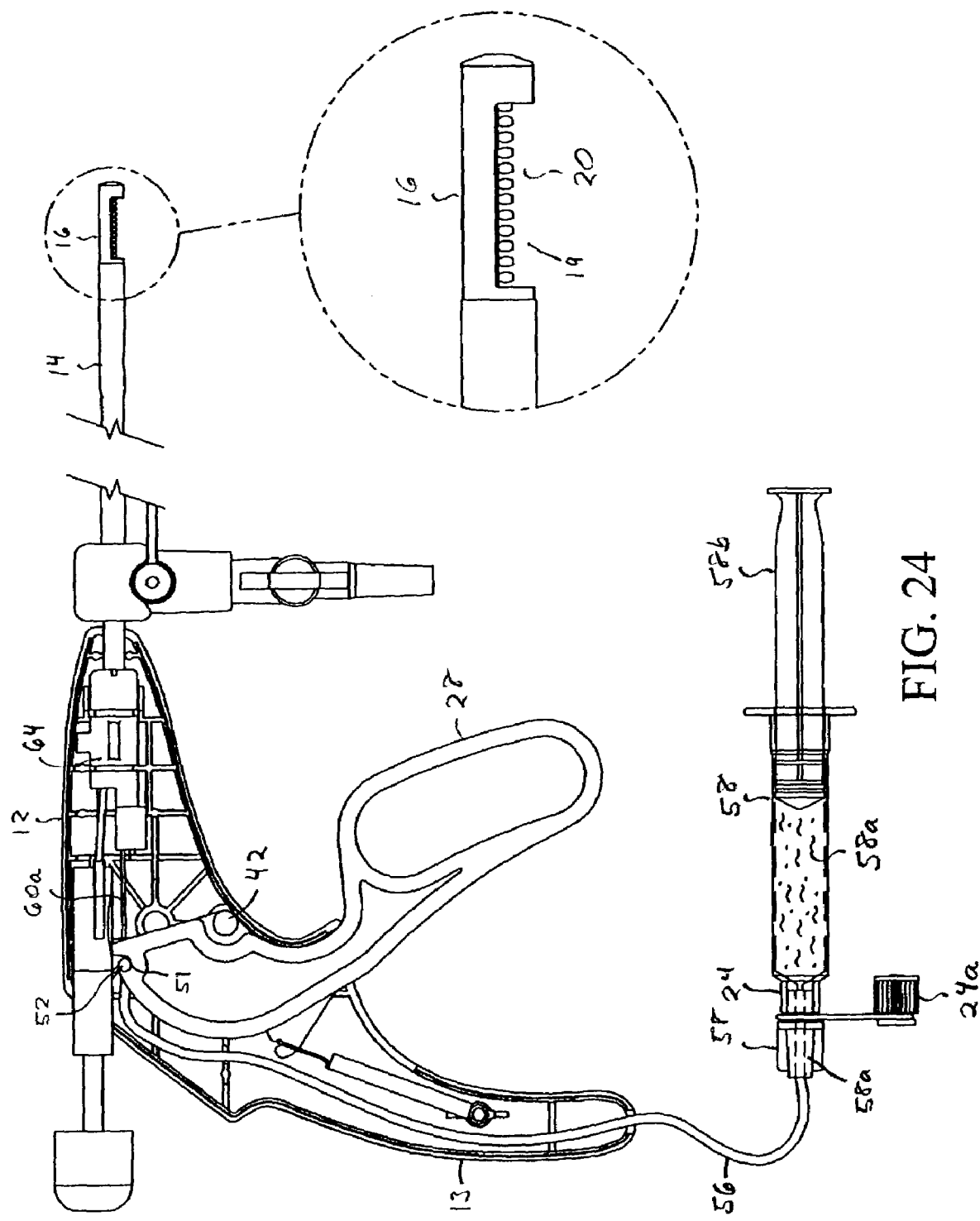
FIGS. 24, 25, and 26 are side views of the instrument of FIG. 1 illustrating the operation of the instrument for infusion fluid at its distal end and the use of needles and to enhance tissue stabilization at the instrument's cavity.
Figure 25:
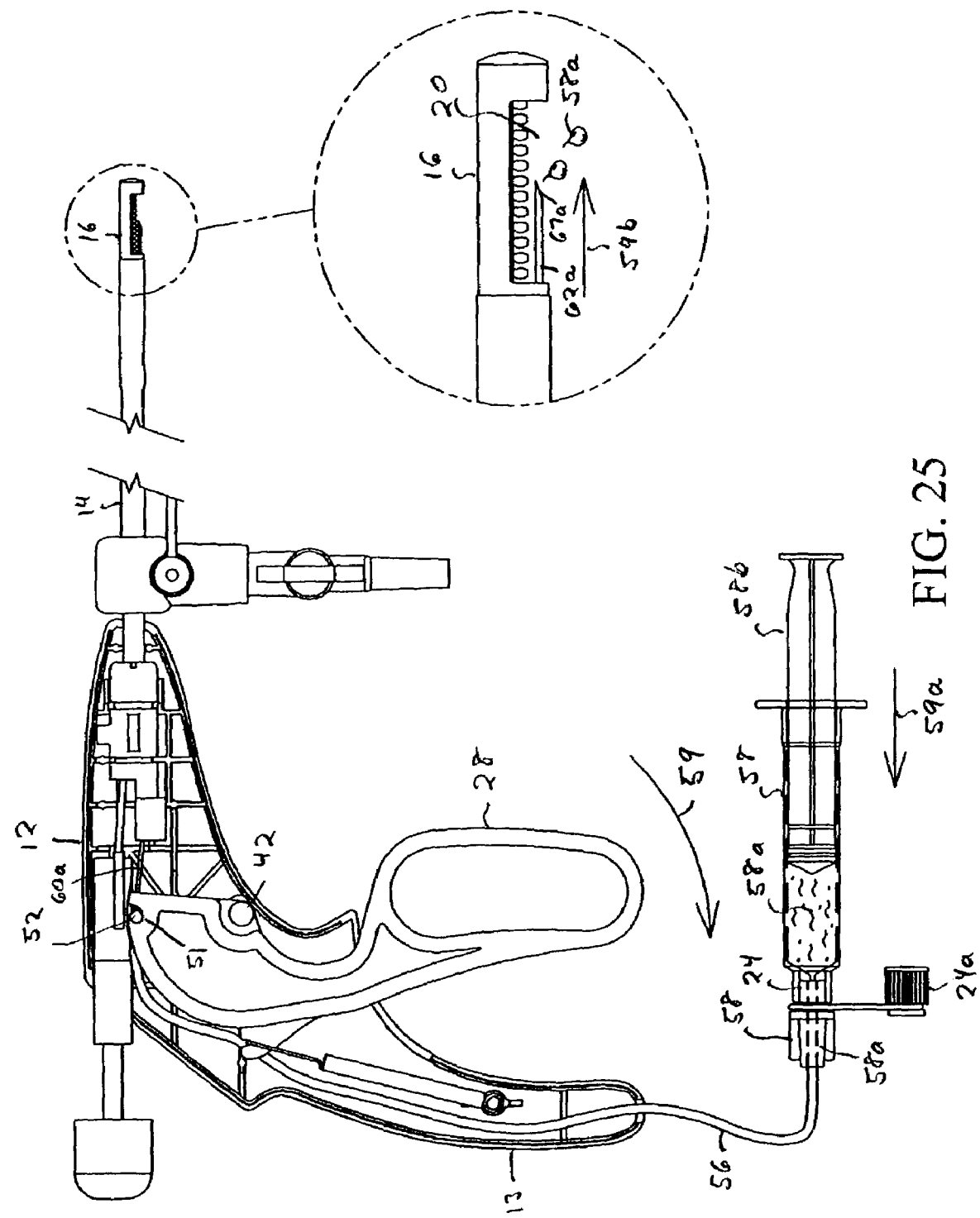
Figure 26:
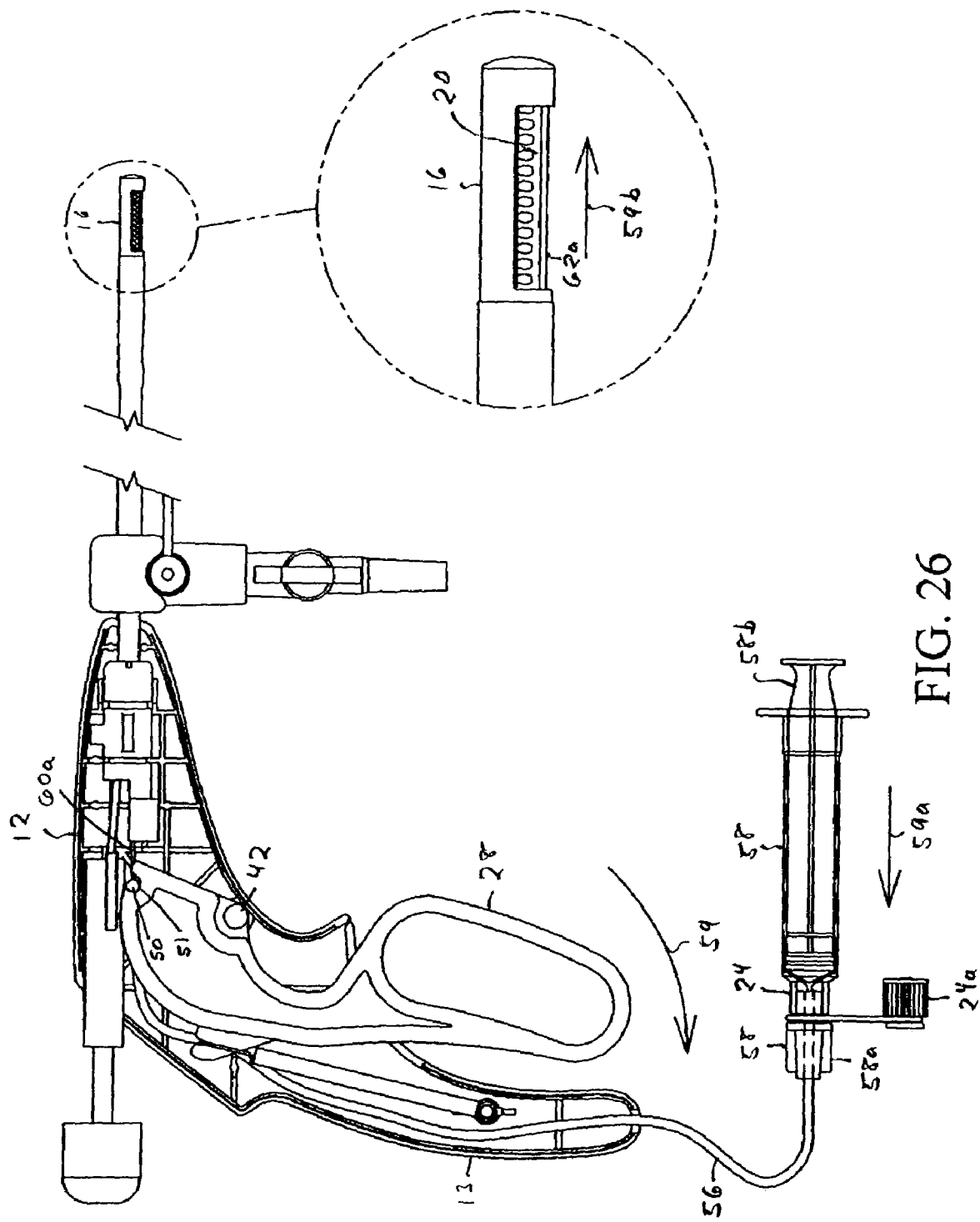

Referring to FIGS. 24-26, the instrument 10 is first shown in FIG. 24 in which a syringe 58 having a fluid 58a is attached to port 24 by removing luer cap 24a from the port. The luer cap 24a may be retained onto port 24 by a ring 29b. Port 24 may be threaded to enable the syringe 58 to screw onto the port. Needles 62a and 62b are driven forward from a retracted position at the distal end 16 by backward pivoting of lever 28 towards handle 13 (as indicated by arrow 59) which drives needle coupler 52 forward and rotates the needle coupler in slot 50, thereby driving the needles forward along their respective paths through the shaft 14, and extending them into cavity 20 (FIG. 25). Next, the plunger 58b of syringe 58 is moved gradually in the direction of arrow 59a forcing fluid 58a from syringe 58 through the fill tube 56, needle coupler 52, via openings 53, into needles 62a and 62b, via opening 53a and 53b, down the needles in the shaft 14 and out needle tips 67a and 67b. The driving or retracting of needles in instrument 10 is independent of fluid insertion. After fluid insertion, needles 62a and 62b may be further extended by pivoting lever 28 towards handle 13 through cavity 20 (FIG. 26). To retract the needles, the lever 28 is pivoted back (in the opposite direction of arrow 59), which drives needle coupler 52 backwards and rotates the needle coupler 52 in the opposite direction in slot 50, thereby retracting the needles 62a and 62b along their respective paths through the shaft 14 and back to their retracted position in the distal end 16.

Figure 56:
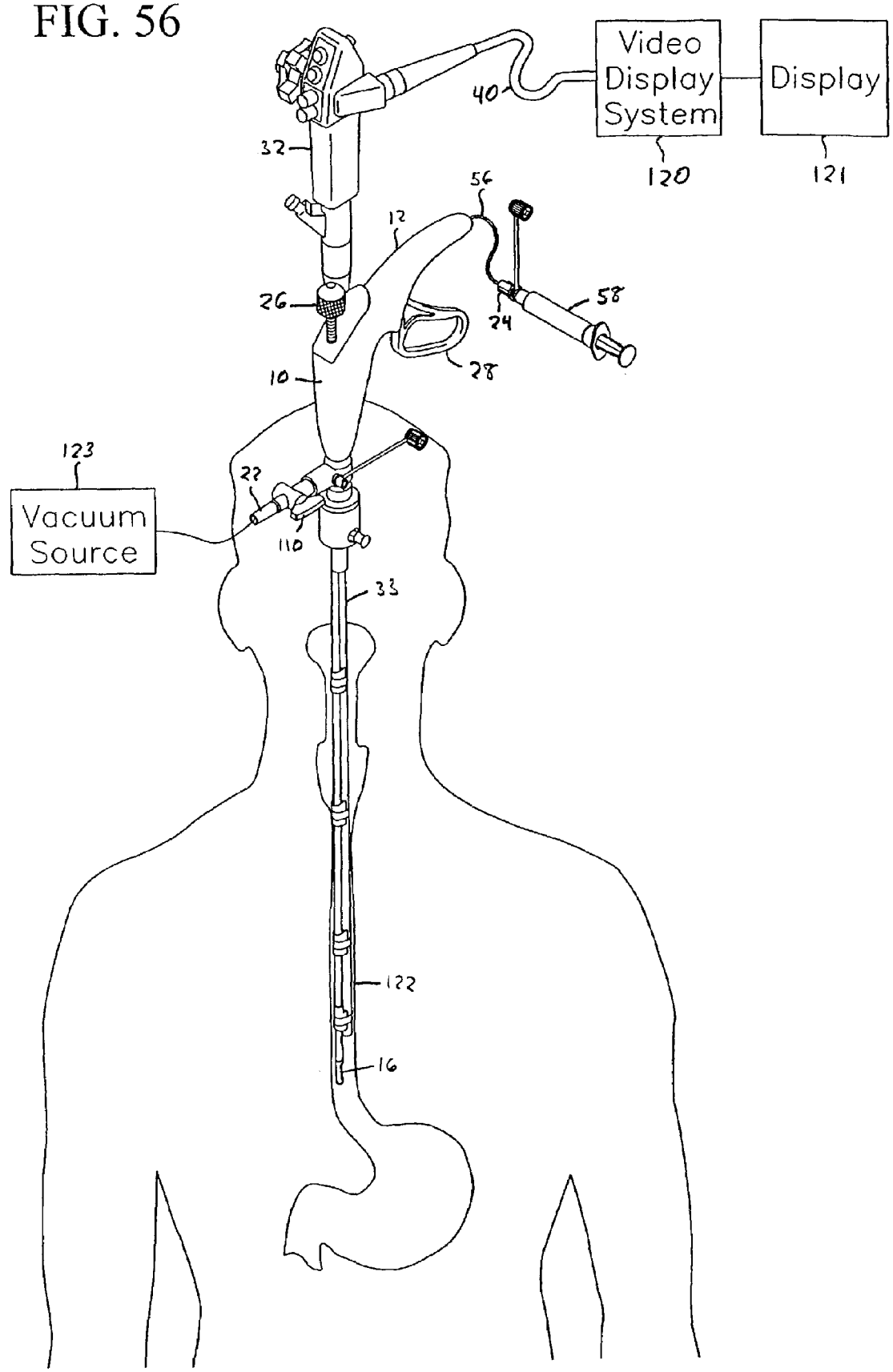
FIG. 56 is an example of the instrument of FIG. 1 positioned in the gastroesophageal tract of a patient using an accessory tube coupled to an endoscope.

Referring to FIGS. 35-45, presented in cross-section, the operation of the instrument 10 at its distal end 16 for engaging and cutting tissue is shown after the instrument is located near the tissue 116 to be removed; the opposite wall 118 is provided to aid in understanding instrument distal end orientation within a tubular tissue structure 115. As stated earlier, the tissue may represent the surface of a tubular structure of a patient body. The distal end 16 may be viewable to the operator on a display through an endoscope, which has optics at its distal end 16, as illustrated in FIGS. 46-55. Such viewing optics may also be directly integrated into instrument 10, as described below in connection with FIGS. 60 and 60A. Such endoscope 32 may represent a gastroscope when located via the mouth into the gastrointestinal tract of a patient as shown for example in FIG. 56, where when the shaft 14 of instrument 10 passes through the accessory tube 30 coupled to the gastroscope, as described earlier in connection with FIGS. 2 and 2A. Endoscope 32 is coupled to a video display system 120, via a cable 40, to allow viewing of tissue from its distal end on a display 121, such as the mucosal layer of tissue lining the esophagus 122. Steering of the endoscope and attached accessory tube 30 is controlled by a cable drive within the end, or by other typical steering means used by endoscopes, so as to locate distal end 16 passed through and out accessory tube 30 near the tissue to be removed. Such steering may also be integrated into instrument 10, as also described below in connection with FIGS. 60 and 60A. Any other endoscope, without accessory tube 30, may also be used which is suitable for application in the particular tubular structure or tissue to be operated upon.

Figure 36:
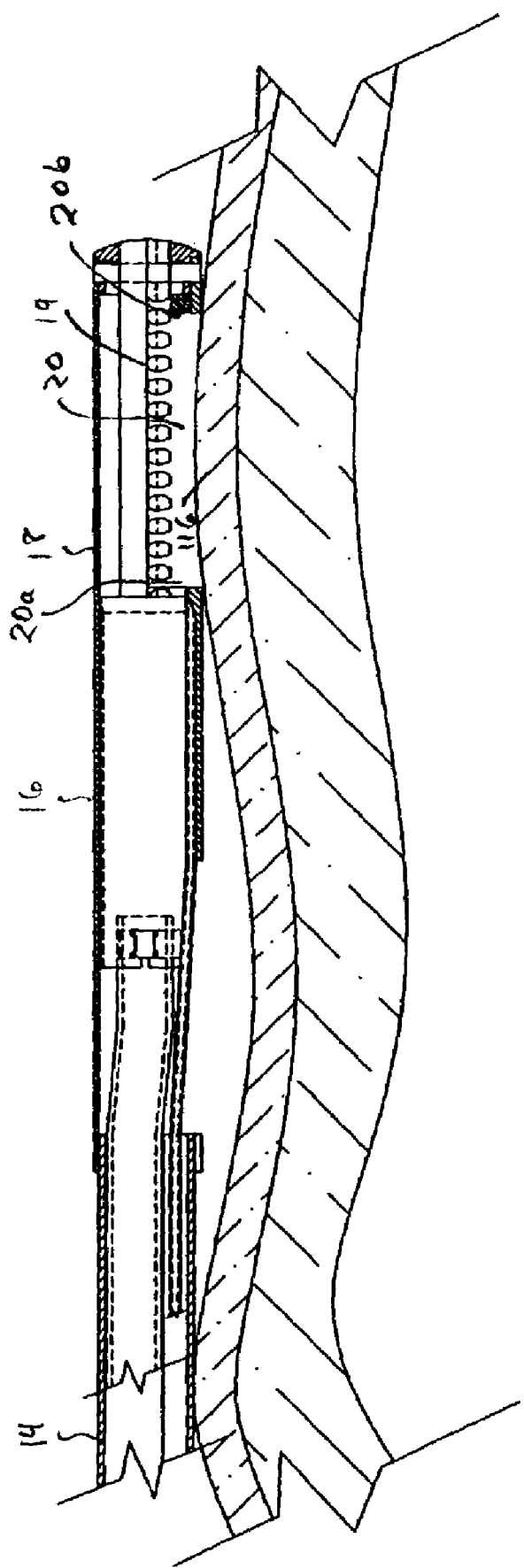
Figure 37:
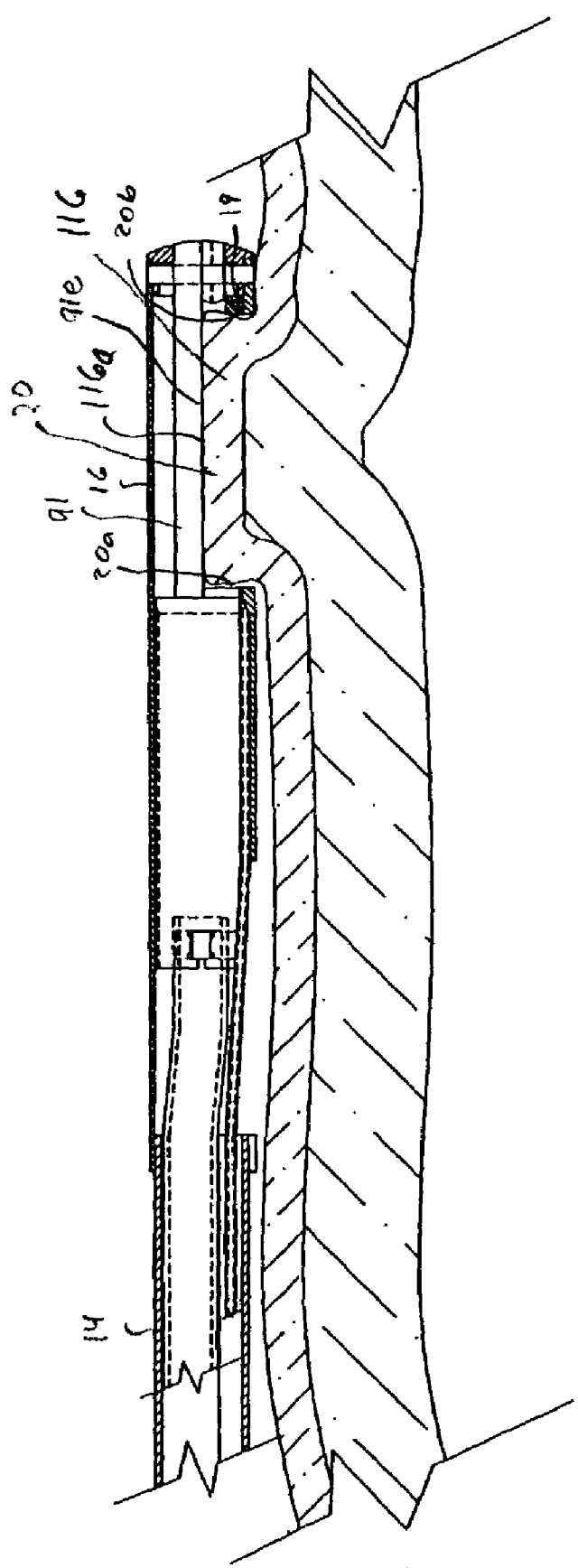
Figures 46, 47, 48:
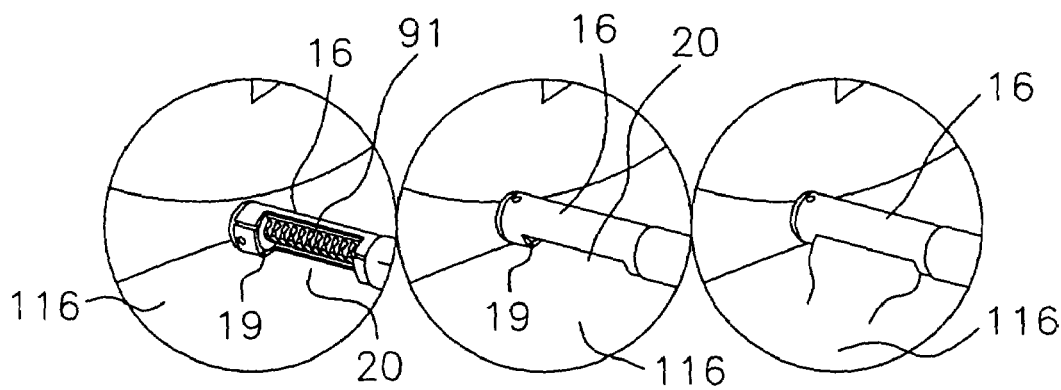
FIGS. 46, 47, 48, 49, 50, 51, 52, 53, 54, and 55 show an example of the views through an endoscope during the operation of the instrument of FIG. 1.

First, with the tube blade 86 and needles 62a and 62b retracted in the distal housing 18 below the cavity 20, and the vacuum valve 110 in the off position, the shaft 14 of instrument 10 is inserted in the tubular structure 115 to locate distal end 16 adjacent the site of the tissue 116 to be cut and removed (FIGS. 35, 36, 46 and 47). For purposes of illustration, the other side 118 of the tubular structure 115 is only shown in FIG. 35. The distal end 16 is then located such that its opening 19 lies adjacent the tissue 116 to be cut in the inner lining of the tubular structure (FIGS. 36 and 47). With a vacuum source 123 coupled to port 22, the vacuum valve 110 is turned to its open position to communicate suction (i.e., negative air pressure) down the shaft 14 to the distal housing 18, as described earlier, pulling the tissue 116 into the cavity 20 via opening 19 (FIGS. 37 and 48). The surface 116a of the tissue 116 is pulled against surface 91e (FIG. 17A) of the manifold member 91 to engage the tissue, such surface being provided by ledges 98 and the projections 92 extending therefrom about openings 94 and 95, such that the tissue surface 116a substantially conforms to surface 91e. As suction is applied to cavity 20, suction will initially be strongest along one side 20a of the cavity 20. This pulls the tissue into the cavity 20 first along its side 20a, causing the suction to be directed into channel 97a via central opening 97 of the manifold member 91 distributing such suction to openings 94 and 95 down the manifold member to end 20b of the cavity 20 near the distal tip 18b. Suction also occurs around the side walls 93 of the manifold member 91 along two gaps 124 (FIG. 17A) between the sides of manifold member 91 and interior of the distal housing 18.

Figure 38:
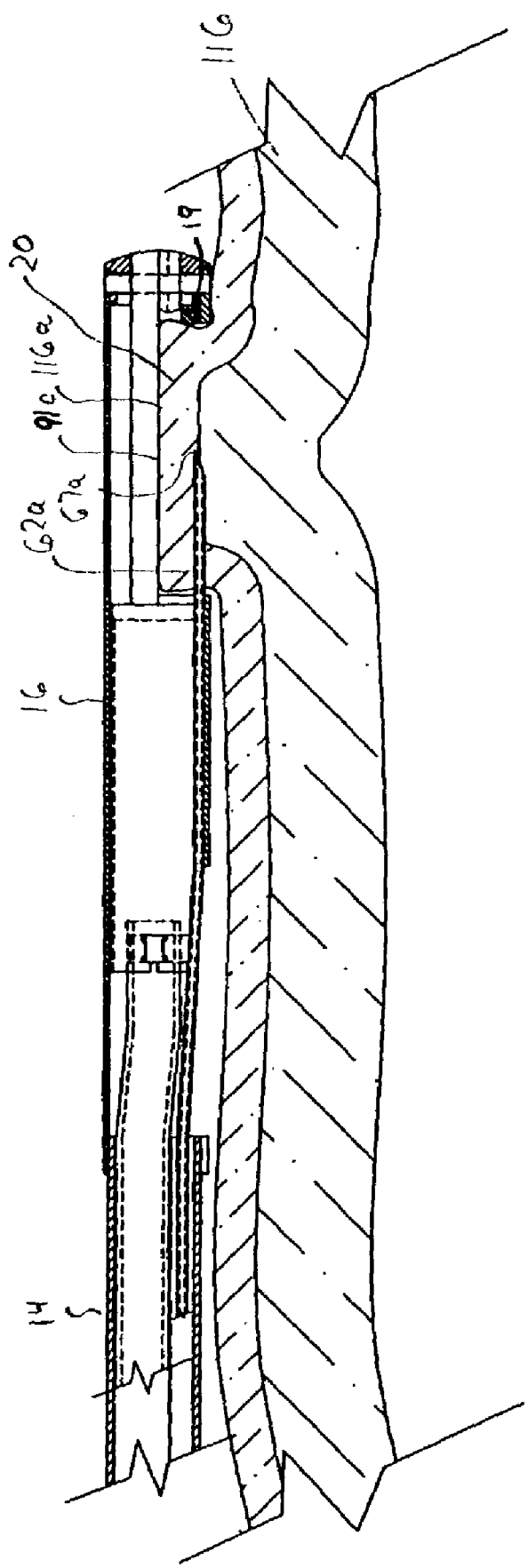
Figure 39:
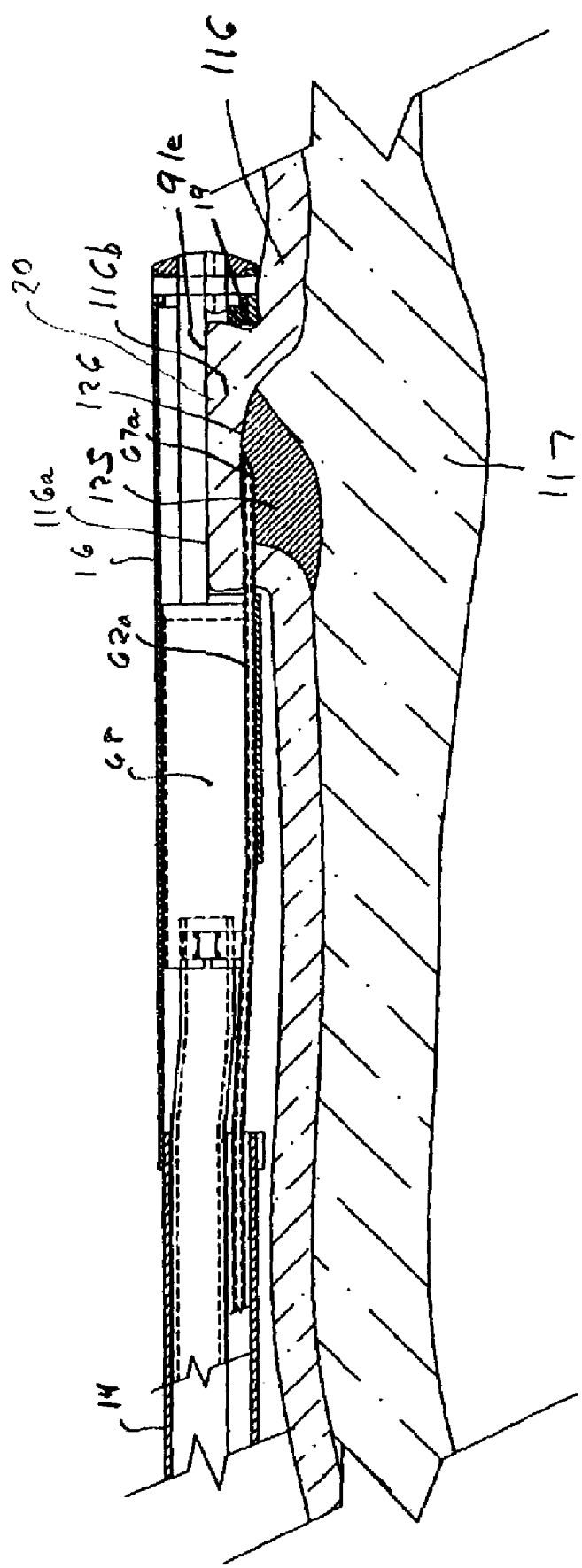
Figure 40:
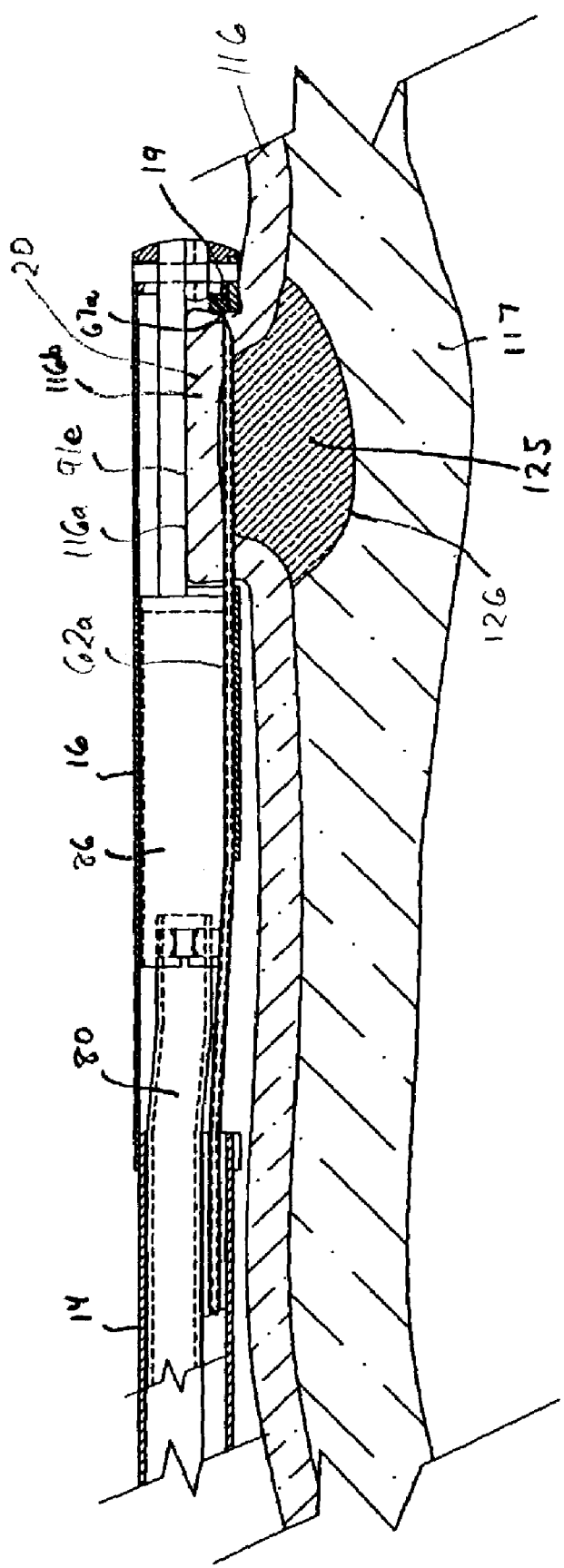
Figures 49, 50, 51:
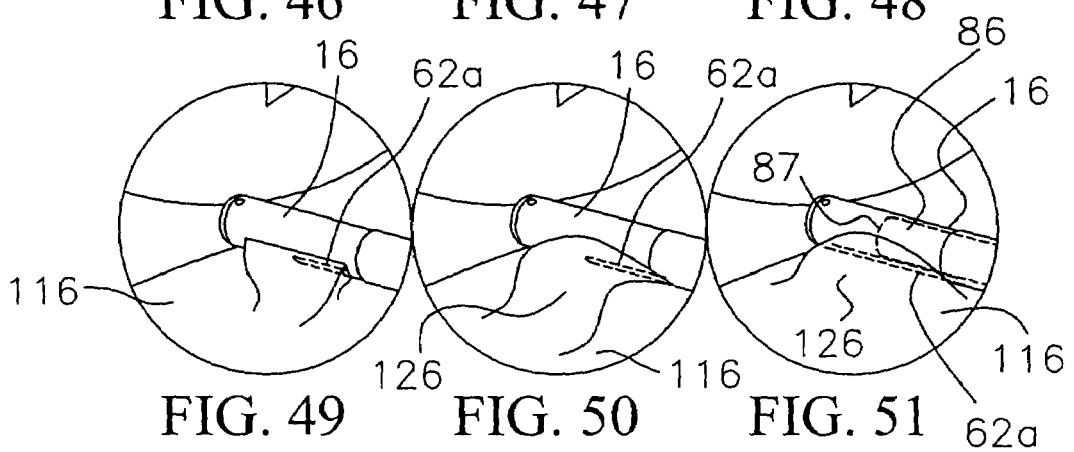

The needles 62a and 62b are then driven forward about halfway into the cavity 20 from their tracks 90a and 90b, respectively, into the tissue engaged in cavity 20 by the operator pulling lever 28 about halfway to handle 13 (FIGS. 38 and 49). Preferably, the needles 62a and 62b are then retracted slightly to assure that holes are left into the tissue 116 to facilitate fluid to be infused (or injected) into the tissue. Fluid 125, such as a saline solution and/or a therapeutic agent, is then inserted via port 24 into the needles 62a and 62b (FIGS. 39 and 50), as described earlier. This forms a welt 126 between the upper tissue layer 116b and the subtissue layer 117 of tissue 116, thereby partially separating layer 116b from layer 117 in the tissue 116 to be cut. The fluid 125 may also contain a hemostatic fluid, such as epinephrine, or other therapeutic agent. During (or after) fluid 125 insertion, the needles 62a and 62b are then further driven forward to fully extend through cavity 20 into their tracks 90a and 90b near distal tip 18b by pulling level 28 to handle 13 (FIGS. 40 and 51). Needles when fully extended may provide additional stability to the tissue 116 in the cavity 20 when the tissue is cut.

Figure 41:
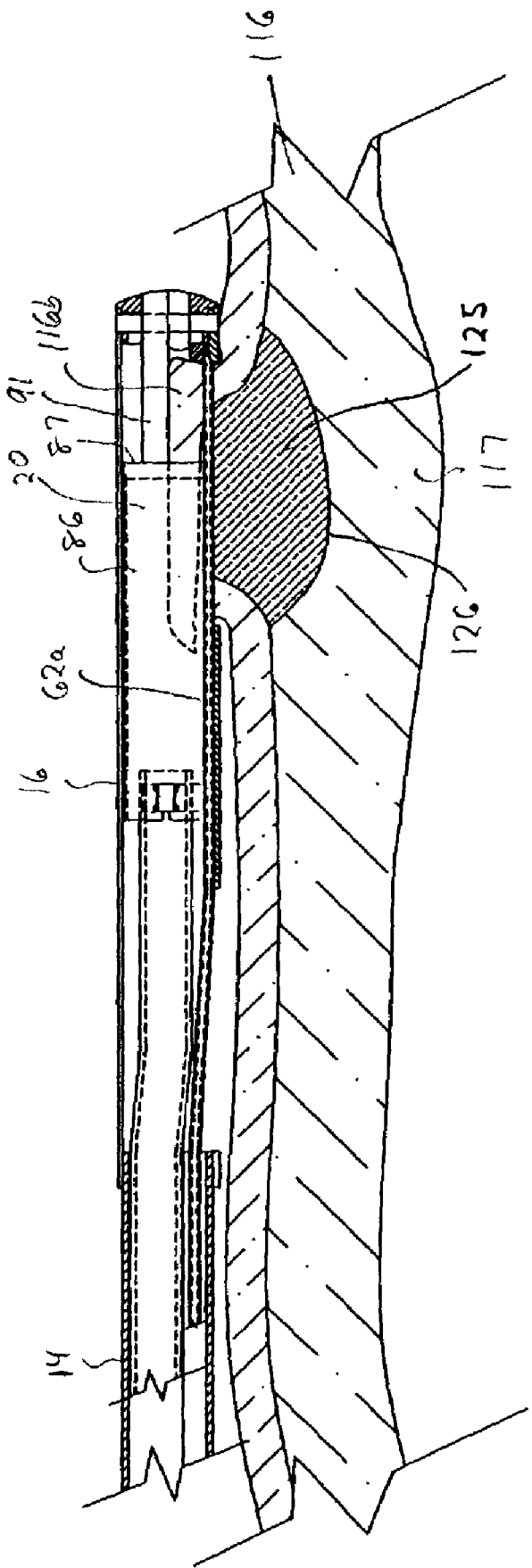
Figure 42:
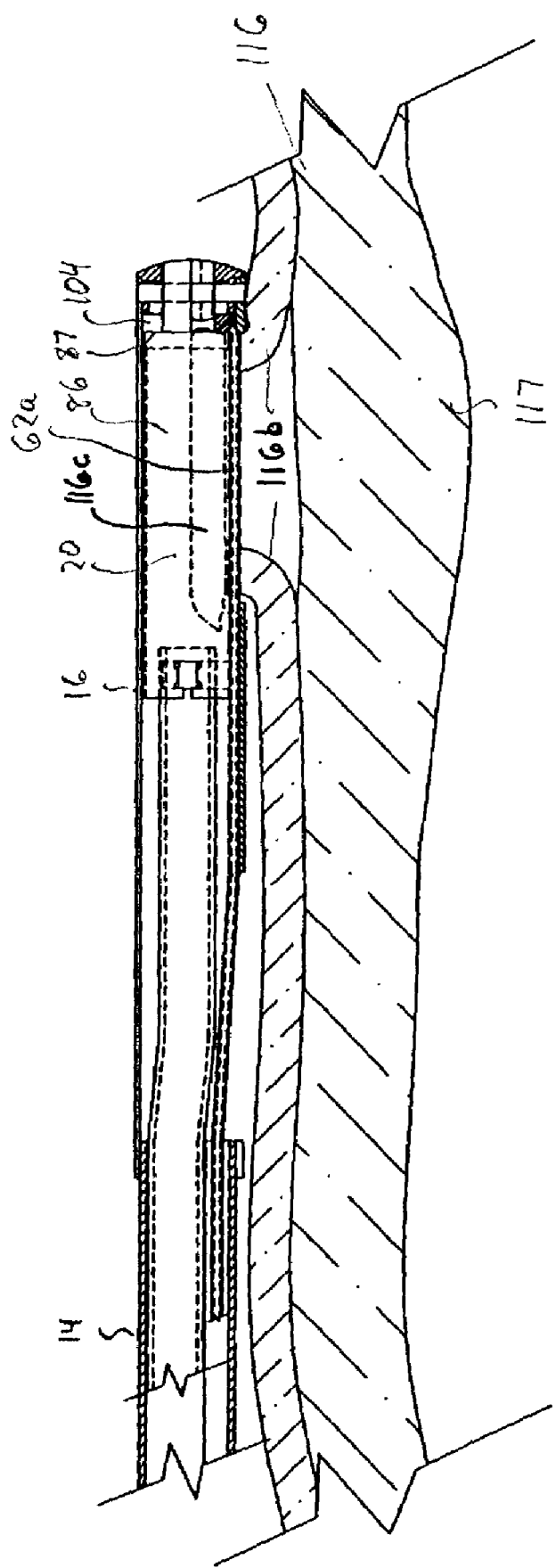
Figure 43:
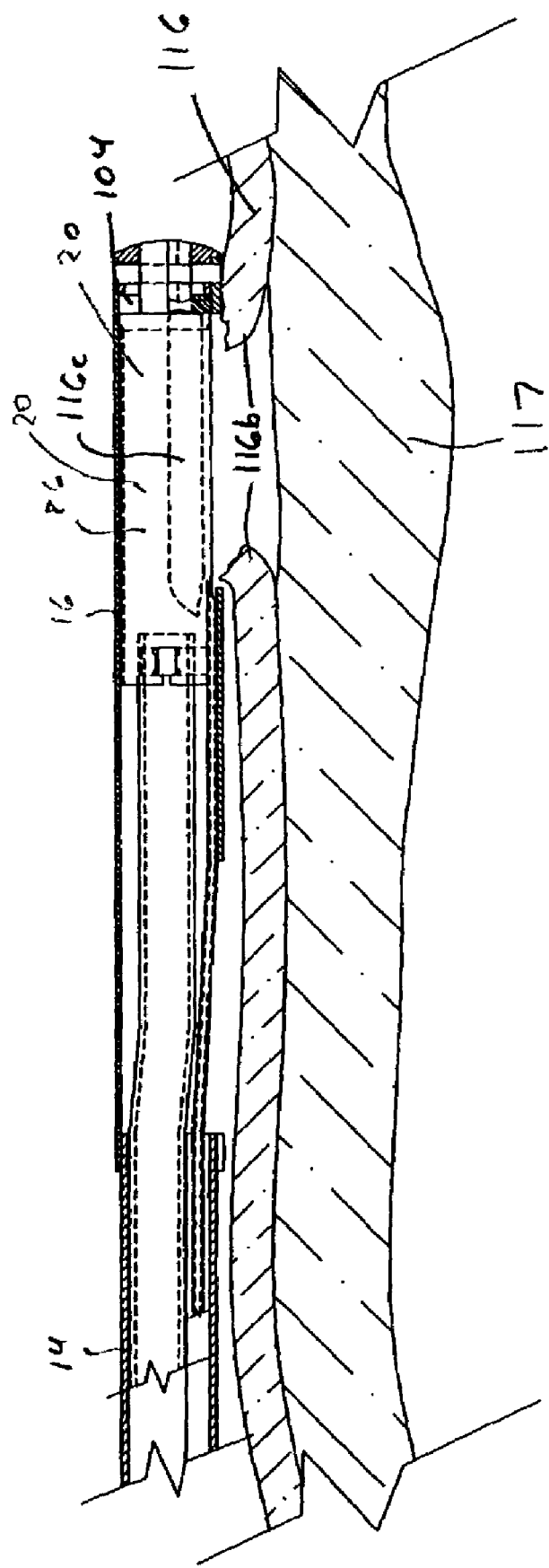
Figure 44:
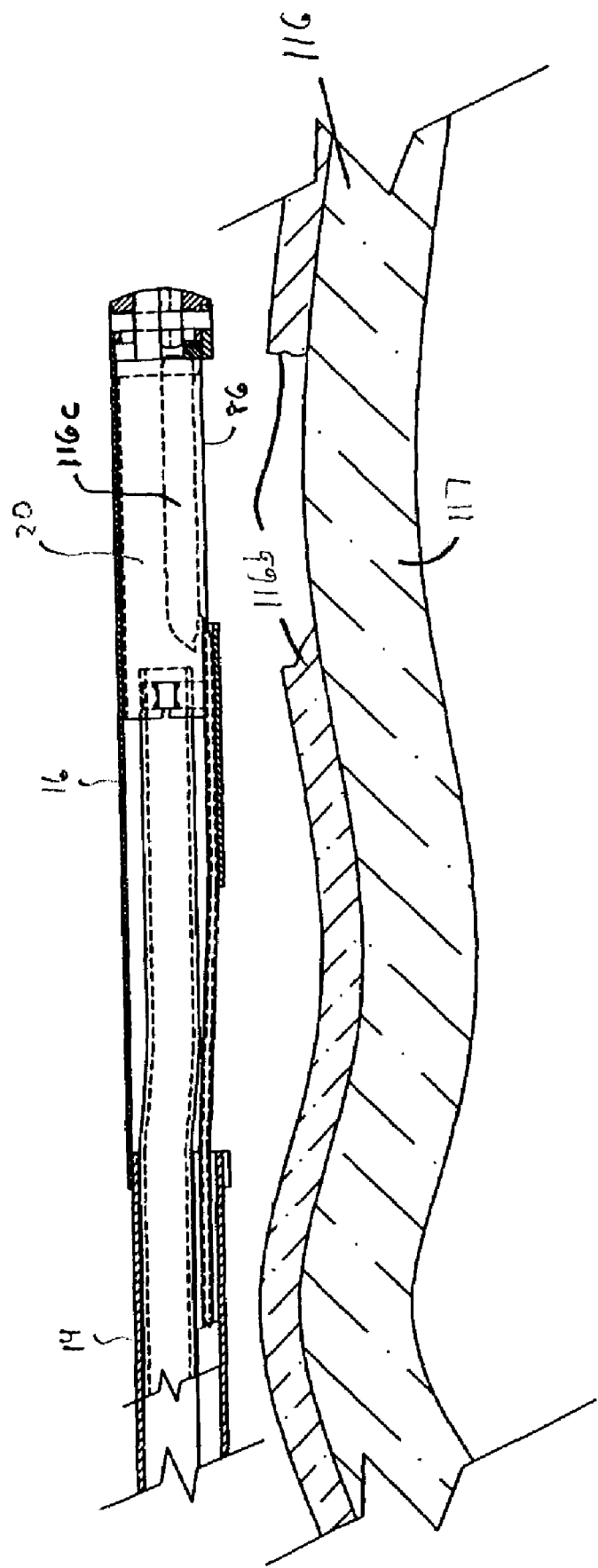
Figures 52, 53, 54:
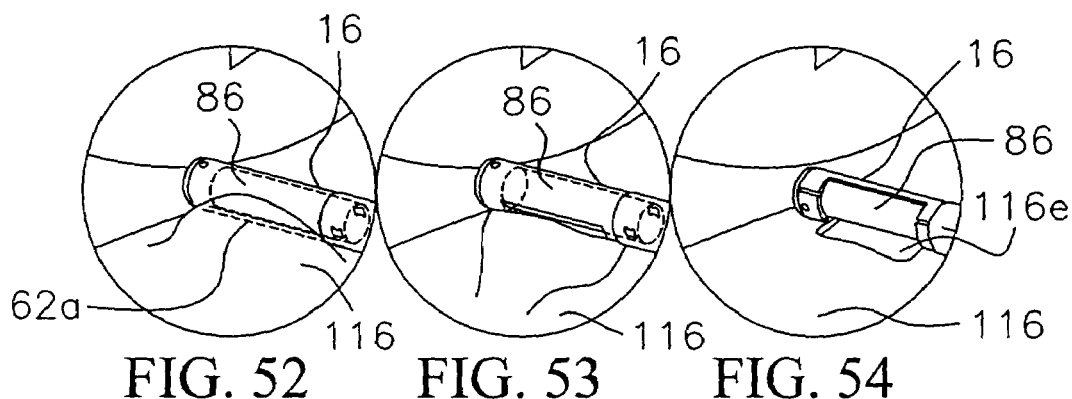
Figure 55:
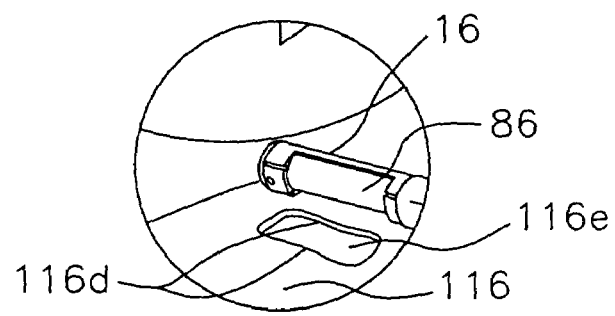

The tube blade 98 is then rotated forward in the cavity 20 by turning turn screw 26 to cut the specified harvested specimen tissue 116c by tube blade edge 87 from the underlying tissue substrate 117 (FIGS. 41 and 51). The tube blade 86 then closes the opening 19 to the cavity 20 and when fully extended, part of tube blade edge 87 abuts against back stop 104 (FIGS. 42 and 52). The harvested tissue specimen 116c so removed remains captured in the cavity 20 as the distal end 16 of the instrument is lifted from the tissue 116 (FIGS. 43-44 and 53-55). The depth of the cut is controlled by the manifold member 91 with respect to tube blade 86 upon extension in cavity 20. In applications for removal of the mucus layer of the esophagus, which may be represented by tissue layer 116b, the depth of the tissue is selected to minimize damage to submucosa and adjacent esophageal muscle, which may be represented by tissue layer 117.

Figure 45:
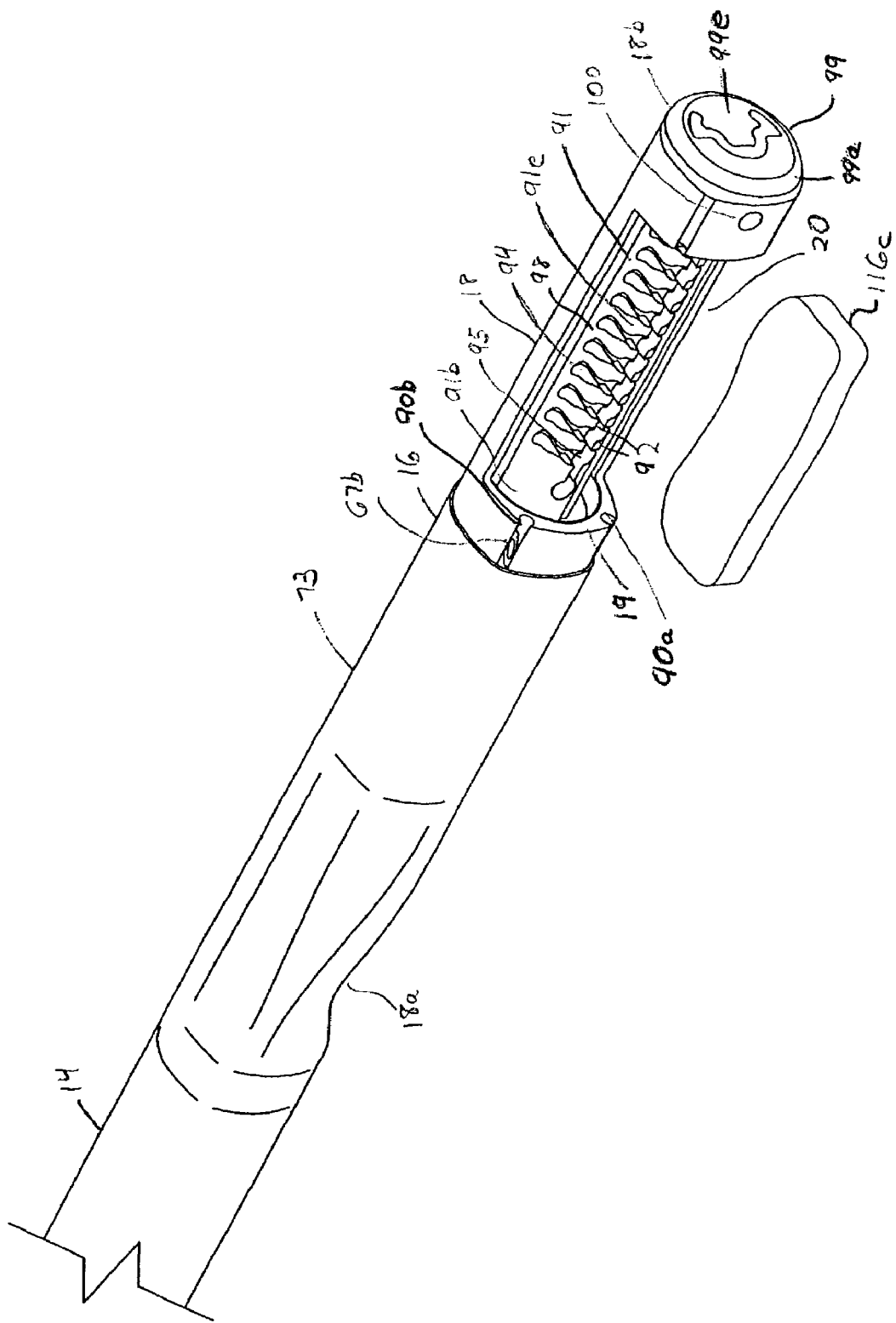
FIG. 45 is a perspective view of the distal end of the instrument after operation of the instrument of FIG. 1 showing removal of the tissue from the distal end.

To enable collection of removed tissue specimen 116c, the entire instrument 10 is removed from the tubular structure 115, and turn screw 26 is rotated in an opposite direction which retracts the tube blade 86 below the cavity 20, the needles 62a and 62b are retracted below cavity 20 by pivoting the lever 28 away from handle 13, and closing suction valve 110, thereby releasing the tissue specimen 116c from the distal housing 18 of instrument 10 (FIG. 45). Such collected removed tissue may represent a biopsy specimen. The biopsy specimen can be permanently marked, such as with ink, to indicate tissue orientation during harvest and subsequently analyzed using a variety of histopathologic techniques. If specimen removal and analysis is not required and multiple precision tissue cuttings are preferred in that patient, the tubular blade and needles can be retracted while the instrument remains in the patient near the harvest tissue site. Flushing the vacuum tract with pressurized irrigant can assist to remove the harvested specimen 116c from the distal end of the instrument. The harvested tissue specimens left near the harvest site could subsequently be passed out of the patient through natural means, such as defecation or micturation. Such flushing may be provided through port 29 to the distal end via the same passages in the shaft which communicate suction. This enables the potential for repeated use of this instrument without requiring removal of the instrument's distal end from the patient.

Port 29 may also be used to clean the site in the tubular structure before or after removal of tissue, or to remove debris in cavity 20 when suction is not being provided down shaft 14 via the same passages in the shaft which communicate suction. Further, although use of fluid to assist in separation of tissue layers is preferred, the instrument can operate to cut tissue by engaging tissue by suction and cutting such tissue without use of the fluid insertion or extension needles. Further, one needle, or any number of needles may be provided in the instrument, or the instrument 10 may be provided without needles.

This instrument overcomes many of the pre-existing challenges associated with the removal of abnormal tissue, such as in the case of Barrett's disease, from the human esophagus. Further the tissue edges on opposite sites 116d (FIG. 55) of the wound 116e left in the tissue after operation of the instrument, are clean, straight and substantially parallel to each other enabling apposition of such edges for closure of the wound, if desired, by suture or other mechanical closure devices. For example, a suturing instrument represents the SEW-RIGHT™ SR•5™ manufactured by LSI SOLUTIONS, Inc. of Victor, N.Y., may be used to apply suture, and free ends of the suture may be closed, such as with a knot placed by a surgeon, or using a suture securing instrument, such as the Ti-KNOT® TK•5® also manufactured by LSI SOLUTIONS, Inc. Also, the suturing and suture securing instruments described in the above-incorporated patent applications may also be used. Such would edge apposition can induce primary healing yielding application or bolstering of a durable wound closure that may be useful in controlling pathologic processes like esophageal reflux disease. The instrument may take a single cut of the tissue or be operated as described above to obtain multiple cuts at multiple locations in a tissue structure. In addition to removing tissue from lining of tubular structures, the instrument may also be used to cut tissue from any tissue surface in a patient's body (e.g., surface of the liver, lining of the peritoneal cavity) or even soft tissue (e.g., from within breast tissue as shown below in FIG. 59A, or brain tissue) which are surgically made accessible.

Figures 57, 57A:
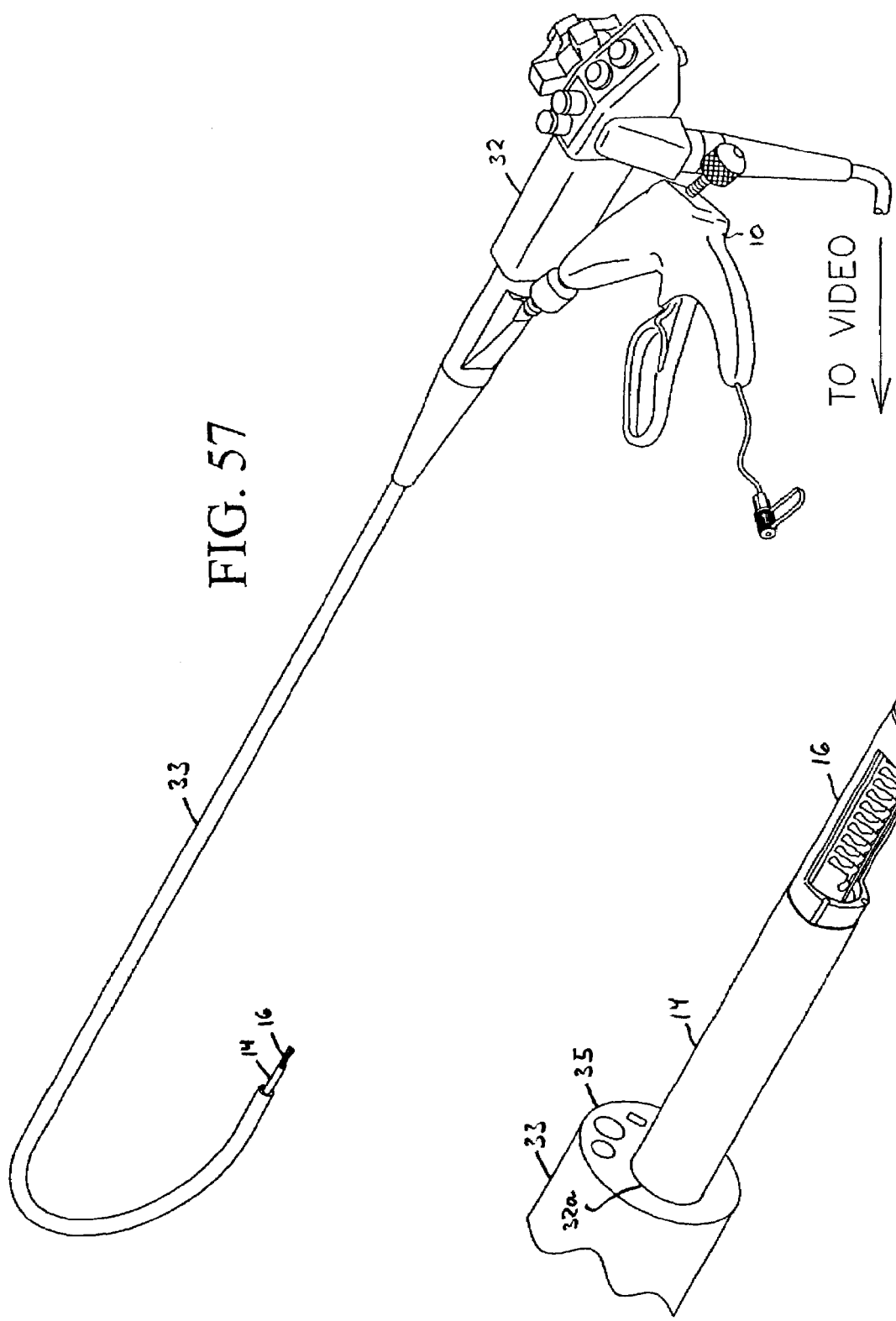
FIG. 57 is a perspective view of the instrument of FIG. 1 passing through the channel of a flexible endoscope.
FIG. 57A is a partial view of the distal end of the instrument of FIG. 57.

Although the operation of the instrument is described through an accessory tube, the instrument 10 may also be insertable through a channel 32a of an endoscope 32, often called the working channel, when such channel has a diameter smaller than the diameter of the shaft 14 and distal end 16, as shown in FIGS. 57 and 57A. If the distal end 16 is of a larger diameter than the channel of the endoscope, but the shaft 14 is of a diameter insertable through such channel, the distal end 16 of the instrument 10 may be assembled on to the shaft 14 after the shaft 14 is passed through the channel of the endoscope, thereby integrating the instrument 10 with an endoscope.

Referring to FIGS. 58 and 58A, instrument 10 is shown having a different distal end 16a with an enlarged distal housing 18 having an opening 19 extending over a wider circumference of the distal housing to enable larger widths of tissue to be cut. For example, in a tubular structure, such as the esophagus, the instrument can make a single cut of about 200 degrees over the interior surface of the esophagus. This is useful in removal of abnormal or suspect tissue from the esophagus since the instrument in a single cut can remove the mucosal lining from over half of a circumferential area of the esophagus. Later, such as two or more weeks to allow for sufficient healing, the instrument can be used to remove the mucosal lining from the other half of a circumferential area adjacent to the location where the first half was removed, thereby removing the mucosal lining over the inner circumference of the esophagus of the length of distal end cavity 20. Optional guide members 34a similar to that of tube guides 34 (FIG. 2) may be attached to the shaft 14 of instrument 10. Such guide member 34a may couple shaft 14 to an endoscope's shaft similar to the manner in which tube guides 34 couple the accessory tube 30 to an endoscope of FIG. 2. Thus, such accessory tube is no longer needed to facilitate use of the instrument 10 with an endoscope.

The instrument 10 of FIGS. 58 and 58A may also have an oscillating blade member 130 to replace tubular blade 86 in the cutting mechanism at the distal end 16. Blade member 130 has a sharp edge 131 capable of cutting tissue, and is held by a pin 132 through a hole 130a journalled in the sides of a coupler member 133, as schematically illustrated in dashed lines in FIG. 58A. One side of the blade 130 is coupled to one end of a spring 135 and the other end of the spring is attached to the distal housing 18 (such as by a pin) so as to bias rotation of the blade about the pin to the left, as shown in FIG. 58B. The coupler member 133 may be a tube similar to earlier described coupler 82 for attachment of flexible tube 80 using tube 84, but does not need keys 82b or protrusions 82a. The blade 130 is rotatable in an oscillating (or reciprocating)

motion about pin 132 against the bias of spring 135, in response to pulling or releasing a cable 136 (e.g., wire) coupling to the other side of blade 130 to a trigger 134 mounted in the handle 13 of the instrument. Holes in the blade 130 are provided for attaching the respective ends of the cable and spring 135 to the blade. Cable 136 extends through shaft 14 via one of the channels (or an additional channel) through the flexible body 80 and needle guide 72 and out an opening in the rigid tube 70 in housing 12 to trigger 134. This opening in rigid tube 70 may have a seal if needed to maintain vacuum when suction is communicated down shaft 14 to the distal end. Pulling trigger 134 rotates the blade 130 to the right against the bias of spring 135 as shown in FIG. 58C, and releasing the trigger 134 rotates the blade 130 back to the left (FIG. 58B), as indicated by arrow 137. This oscillating motion is controlled by the user of the instrument 10 via the trigger 134, and the blade 130 is advanced forward (or backwards) by turn screw 26 in the same manner as advancing tube blade 86 so as to cut tissue when held by suction and stabilized by needles in cavity 20 against the tissue engaging surface. The width of the blade 130 is greater than the width of opening 19, and the blade may be flat or curved. Either oscillating blade 130 or tubular blade 86 may be used in distal housing 18 or 18a of the instrument 10, and such blades, like other components of the instrument 10 interfacing with a patient body, are made of stainless steel or other biocompatible material.

Figure 4:
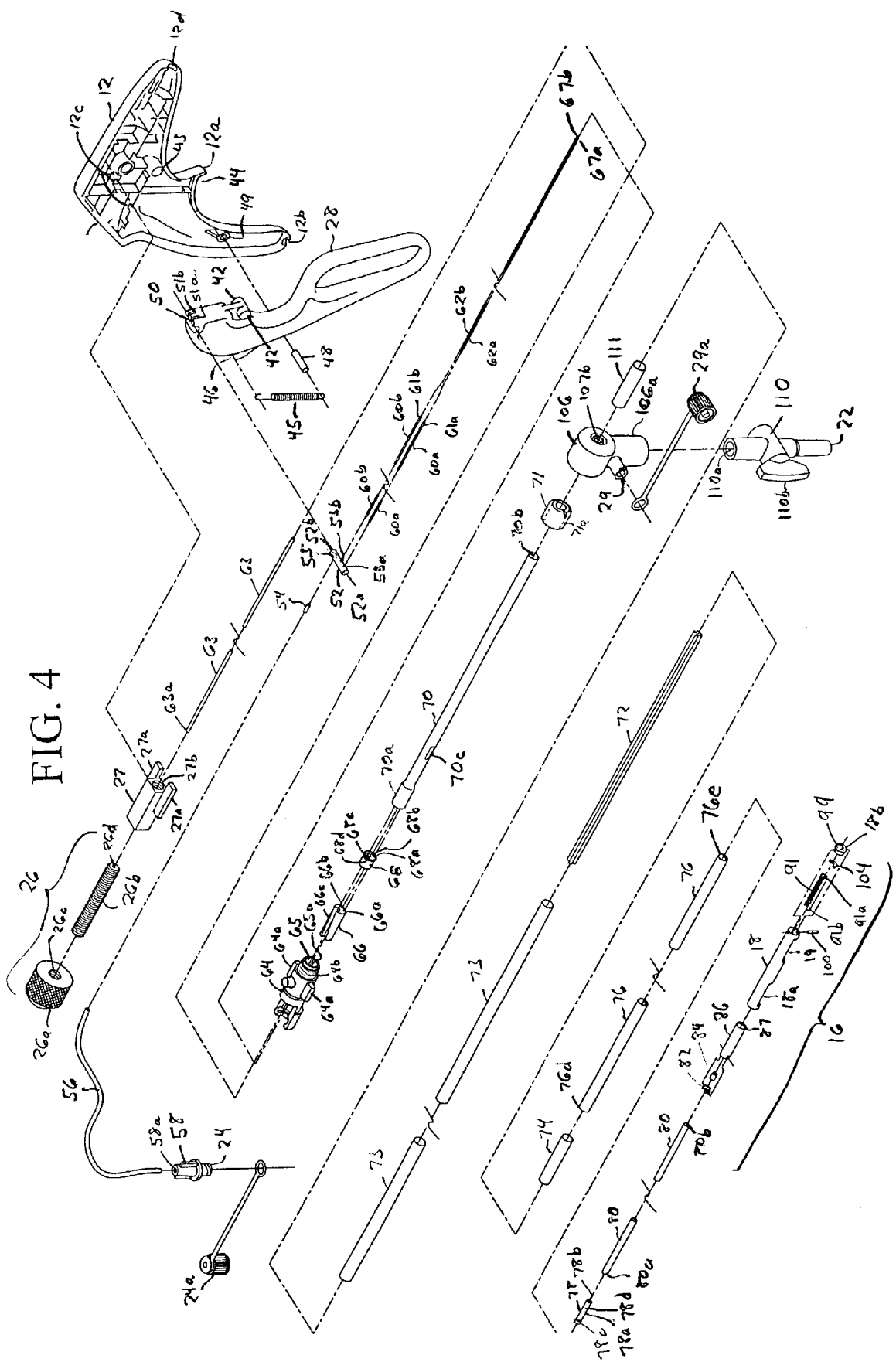
FIG. 4 is an exploded perspective view of the instrument of FIG. 1 in which the right cover of the housing is removed.

Referring to FIGS. 59 and 59A, another embodiment of the instrument 10 is shown for use in obtaining a biopsy from the breast 141 of a patient. Typically, a flexible guide wire 142 is first inserted into the breast to locate abnormal or suspect tissue 140. The flexible guide wire 142 may be drawn through the instrument 10, via an opening in cap 99 at the distal end 18 under or through manifold 91, through the distal housing 18 to one of the channels (or an additional channel) of the flexible body 80 and needle guide 72, and then out an opening in the rigid tube 70 in housing 12 through an opening adjacent to opening 12b (FIG. 4). The opening in rigid tube 70 may have a seal if needed to maintain vacuum when suction is communicated down shaft 14 to the distal end 16. To facilitate passing the guide wire 142 through the instrument 10, a lead wire (not shown) may be use which is loaded along the path over which the flexible guide wire will pass, and then is temporarily attached to the guide wire end not located in breast tissue, such that pulling the lead wire will pass the guide wire 142 through the instrument 10. The path of guide wire 142 is represented by dashed lines through shaft 14 and housing 12 in FIG. 59. The instrument's distal end 16 can thus pass through a surgical opening 140 along the guide wire 142 into the patient's breast 141 near the site of tissue 140. An image transducer 144, such as an ultrasonic or other imaging means, is located in the distal housing 18, to image tissue adjacent the distal end 16 so that all or part of tissue 140 can be suctioned into the instrument and cut to capture a biopsy specimen as described earlier. When the instrument is then removed from the breast 141, the biopsy specimen can be removed from the distal end and evaluated. The image transducer 144 is sufficiently small to be located in the distal housing 18 along the gap 124 (FIG. 17A) sized for the transducer along the manifold 91. The transducer 144 emits and receives signals for imaging through cable(s) extending through the instrument 10 to an image display system 145, similar to that of a typical ultrasonic imager for viewing images on a display. Such cable(s) may extend through shaft 14 through one of channels (or an additional channel) of flexible body 80 and needle guide 72, and then out an opening in the rigid tube 70 in housing 12, to image display system 145. This opening in the rigid tube 70 may have a seal to maintain vacuum when suction is communicated down shaft 14 to the distal end, if needed. The shaft 14 may be flexible or rigid.

Optionally, the instrument 10 may have an imaging system and/or steering mechanism shown in FIGS. 60 and 60A. The distal housing 18 has an opening 146a for an illumination source 148 and another opening 146b for an image detector 149. The image detector 149 may represent the end of a coherent bundle of optical fibers, lens, or an electronic image detector, such as a CCD. The image detector 149 is coupled by cable(s) 151 through the instrument 10 to a video display system 150 for viewing images from the distal end 16 on a display 152. The illumination source 148 may also represent optical fiber(s) 153 coupled to a light source 154 for providing such illumination, but any illumination means may be used which provides sufficient illumination for enabling imaging by detector 149. Cable(s) 151 or fibers(s) 153 may extend through shaft 14 via one of the channels (or additional channel(s)) through the flexible body 80 and needle guide 72 and out an opening in the rigid tube 70 in housing 12, to trigger 134. This opening in rigid tube 70 may have a seal, if needed, to maintain vacuum when suction is communicated down shaft 14 to the distal end. For example, the image system provided by illumination source 148, image detector 149, illumination 148, and video display system 150, may be similar to that used in a typical endoscope. Also, a steering mechanism is provided by multiple wires or cables 152, such as four, which travel from the housing 12 in channels, tubes, or sheaves along outside length of shaft 14 and coupled to the distal end housing 18 and are movable in such channels or sheaves. Optionally, such wires 152 may pass through tubes or sheaves internal in shaft 14. By controlling the length of one or more of the different wires 152 along shaft 14 using a controller or dials 154 mounted in the housing 12, the distal end 16 is steerable. For example, the steering mechanism may be similar to that used by a typical endoscope, such as a gastroscope, for steering its distal end. Advantages of the integrated imaging and steering mechanisms are that an endoscope is no longer needed to assist in operating the instrument as described earlier in connection with FIG. 2, and the interface between the instrument and patient can be further miniaturized.

Referring to FIGS. 61 and 61A-61E, instrument 10 is shown having distal end 16a and guide members 34a of FIG. 58, where a linear blade member 156 replaces oscillating blade member 130 in the cutting mechanism. The linear blade member 156 has a sharp edge 156a, like a scalpel, and an end 156b coupled to a wire 158. Wire 158 extends from the blade member 156 through shaft 14 and housing 12 to a ball or spherical member 160 rotatably mounted in a socket formed at the end of shaft 26b at turnscrew 26 (FIG. 61D). A retainer member may be used to retain the ball in such socket. An attachment of a wire to a turnscrew utilizing such a ball and socket joint is shown, for example, in U.S. patent application Ser. No. 10/095,842, filed on Mar. 12, 2002, which is incorporated by reference. However, other mechanical means may also be used to couple the wire to a turnscrew or rotatable control knob, which when rotated does not couple such rotation to the wire. Wire 158 replaces the drive tube 63, coupler member 78, flexible tube 80, and tube 84 described earlier, and travels along the same path as such through housing 12 and shaft 14 to distal end 16a. Wire 158, for example, may be of stainless steel, and is sufficiently flexible to enable flexure along flexible section 14b of the shaft. Blade member 156, for example, may also be made of stainless steel. The wire 158 may also be provided by two separate wires (or tubes) coupled together, one which is substantially rigid for passage through rigid portion 14a and another which is substantially flexible for passage through flexible section 14b of the shaft 14.

The blade member 156 is disposed in distal housing 18 such that the blade member advances from a retracted position before cavity 20, as shown in FIG. 61D, along a linear path, centrally oriented, through the cavity to cut tissue engaged therein against manifold 91. The length of edge 156a is such that when fully extended through the cavity, it is capable of producing a longitudinal incision across the length of cavity 20. FIGS. 61A, 61B, and 61E show forward blade advancement in which full-extended position is shown in FIGS. 61C and 61F. The path of blade member 158 is provided through channel 97a via opening 97 of manifold member 91 (FIG. 17) such that the blade edge 156a extends upwards through central opening 95 (FIG. 45) as it passes through cavity 20. To allow blade member 156 to enter channel 97a and central opening 95, an opening (or slit) extends through end 91b of manifold member 91 such that the blade member can pass into and through channel 97a and central opening 95. The blade member 156 is advanced by rotating turn screw 26, as indicated by the arrow 162, to translate forward motion to blade 156 via wire 158, as indicated by arrows 163, but avoiding translation of rotation to the wire by use of ball and socket coupling to shaft 26b. The incision made in tissue is of a length defined by the length of cavity 20, and is of a depth from surface 91e of manifold 91 and height of blade edge 156a with respect to this surface. When turn screw 26 is then rotated in the opposite direction, the blade member 156 is translated in the opposite direction to retract the blade member.

One application of instrument 10 of FIG. 61 is to make a controlled incision in tissue at remote locations for purposes of releasing constricted or narrowed tissue passageways. For example, the chronic burning of the distal esophagus in GERD can also cause pathologic scar formation (i.e., stricture) that reduces the luminal passageway of the esophagus and potentially restricts flow of the swallowed food. A common practice in surgical disease states is to longitudinally cut open a narrowed tube and suture it back closed in a transverse orientation to reestablish a wider lumen. This maneuver, sometimes called the Heineke-Mikulicz technique, utilizes redundant tissue length to overcome constricted tissue diameters. For example, a normal adult esophagus usually has an inner diameter of about 20 mm. When disease causes the diameter to narrow to less than 12 mm, swallowed material passage can become inhibited. The distal end 16a with linear blade member 156 may also be used in other tubular structures of the gastrointestinal tract, urinary tract, or vascular structures, and along any tissue surface or within soft tissue structures.

The instrument 10 is sized in accordance with the particular tissue structure into which the instrument will be inserted, and the distal end 16 may be sized in terms of the dimensions of the opening, cavity, and location and contour of manifold member therein for the particular size and depth of the tissue to be cut and removed when such tissue is held by suction and stabilized by the needles upon the tissue engaging surface provided by the manifold. Further, to obtain a longer or shorter shaft 14 with different lengths of the rigid and flexible sections 14a and 14b can be achieved by adjusting the length of the rigid tube 70 and the flexible body 76. For example, in application of the instrument through the mouth into the esophagus of a patient, the shaft 14 of the instrument may be 75 cm in length to distal housing, both with a diameter of 6 mm. Although the apparatus 10 is described herein for use in human patients, it may also be used in animals with proper sizing of the shaft 14 and distal end 16.

From the foregoing description, it will be apparent that an improved instrument and method for surgically cutting tissue is provided to remove tissue from remote sites in the body of a patient. Variations and modifications in the herein described an apparatus and method in accordance with the invention will undoubtedly suggest themselves to those skilled in the art. For example, although the instrument is directed for use in tubular structures, it may be used in other surgical application where remote cutting of tissue is required. Accordingly, the foregoing description should be taken as illustrative and not in a limiting sense.

The invention claimed is:

1. An instrument for cutting tissue comprising:
a proximal end having a housing;
a shaft extending from said housing;
a distal end coupled to said shaft;
said distal end having a cavity and an opening to said cavity;
means for providing suction along said shaft to said distal end;
means for distributing said suction at said distal end through one or more openings of a tissue engaging surface in said cavity to enable tissue adjacent said opening of said distal end to be pulled into said cavity against said tissue engaging surface; and
means for cutting said tissue engaged by said suction against said tissue engaging surface to provide a single tissue specimen in said cavity, in which said cutting means has a blade extendable over said tissue engaging surface to cut tissue extending through said opening and thereby capture said single tissue specimen engaged against said tissue engaging surface, wherein the tissue to be cut is retained in said cavity of said distal end in response to the suction provided through said one or more openings in the tissue engaging surface both before and after extension of said blade over said tissue engaging surface.

2. The instrument according to claim 1 further comprising one or more hollow needles which extend from said housing through said shaft to said distal tip in which said needles are extendable through said cavity and enable injection of fluid passing through said needles to said tissue when located in said cavity.

3. The instrument according to claim 2 further comprising means for actuating said needles in said housing to extend or retract at said distal end.

4. The instrument according to claim 2 wherein said injected fluid is capable of separating layers of said tissue.

5. The instrument according to claim 2 wherein said needles when extended assist in stabilization of tissue suctioned against said tissue engaging surface.

6. The instrument according to claim 2 wherein said fluid represents saline.

7. The instrument according to claim 2 wherein said fluid represents a therapeutic agent.

8. The instrument according to claim 2 wherein said fluid represents a hemostasis agent to minimize bleeding.

9. The instrument according to claim 2 wherein said fluid represents an analgesic.

10. The instrument according to claim 2 wherein said fluid represents one or more of epinephrine and lidocaine.

11. The instrument according to claim 2 wherein said needles are extended through said cavity prior to operation of said cutting means.

12. The instrument according to claim 1 wherein said tissue specimen cut by said cutting means has a depth in accordance with size of said cavity and contour of said tissue engaging surface in said cavity.

13. The instrument according to claim 1 wherein dimensions of said tissue specimen cut by said cutting means is in accordance with at least the size of the cavity and contour of said tissue engaging surface in said cavity.

14. The instrument according to claim 1 wherein said openings along said tissue engaging surface represent a grate capable of distributing said suction to engage the surface of said tissue adjacent said opening when said suctioning means is operated.

15. The instrument according to claim 1 wherein said means for distributing said suction comprises a manifold member having a central channel and two sets of projections each extending upwards from opposite sides of said channel towards each other, and said openings for distributing suction are formed by gaps between said projections and by a gap between said two sets of projections.

16. The instrument according to claim 1 wherein said wound in the tissue provided after operating of said cutting means results in substantially parallel opposing edges which are capable of being apposed.

17. The instrument according to claim 1 wherein said tissue specimen cut represents a tissue specimen biopsy.

18. The instrument according to claim 1 wherein said shaft is locatable along a tissue surface at remote locations in body of a patient.

19. The instrument according to claim 1 wherein said shaft is locatable in a tubular structure of the body of a patient for operating upon tissue along the lining of said tubular structure.

20. The instrument according to claim 19 wherein said tubular structure represents one of gastrointestinal tract or urinary tract.

21. The instrument according to claim 1 wherein said shaft is locatable in a vascular tract of a patient.

22. The instrument according to claim 1 wherein said means for providing suction is controlled at said proximal end.

23. The instrument according to claim 1 wherein said shaft is substantially flexible.

24. The instrument according to claim 1 further comprising means for actuating said blade in said housing to extend or retract at said distal end.

25. The instrument according to claim 1 wherein said blade represents a rotatable blade extendable over said tissue engaging surface to close said opening of said cavity when said blade is fully extended.

26. The instrument according to claim 1 wherein said blade represents an oscillating blade extendable over said tissue engaging surface in said cavity.

27. The instrument according to claim 1 wherein said shaft represents an assembly having a first section and a second section, said first section being rigid and extends from said housing, and said second section being flexible and extends from the first section to the distal end of said instrument.

28. The instrument according to claim 1 wherein said shaft of said instrument is insertable through a channel of an endoscope.

29. The instrument according to claim 1 wherein said shaft of said instrument is insertable through a tube coupled to an endoscope.

30. The instrument according to claim 1 further comprising an endoscope having a shaft with a distal end and a channel through which said shaft of said instrument extends, and said distal end of said instrument extends from said distal end of said endoscope.

31. The instrument according to claim 1 further comprising means for receiving a guide wire through said instrument to assist in locating said instrument in the body of a patient.

32. The instrument according to claim 1 wherein said distal end is locatable in breast or brain tissue of a patient.

33. The instrument according to claim 1 further comprising means for ultrasonically imaging tissue at said distal end.

34. The instrument according to claim 1 further comprising means for steering said distal end.

35. The instrument according to claim 1 further comprising means for optically imaging tissue at said distal end.

36. The instrument according to claim 1 wherein said blade when extended over said tissue engaging surface is extended along said opening of said distal end so as to close said opening to said cavity of said distal end, and thereby capture said single intact tissue specimen engaged against said tissue engaging surface.

37. An instrument for cutting tissue comprising:
a proximal end having a housing;
a shaft extending from said housing;
a distal end coupled to said shaft;
said distal end having a cavity and an opening to said cavity;
means for providing suction along said shaft to said distal end in which said distal end;
means for distributing said suction at said distal end through one or more openings of a tissue engaging surface in said cavity to enable tissue adjacent said opening of said distal end to be pulled into said cavity against said tissue engaging surface; and
means for cutting said tissue engaged against said tissue engaging surface in said cavity, wherein said cutting means utilizes a single linear edged blade oriented along a longitudinal dimension of the cavity to cut a linear slit incision across said cavity of a predetermined length and depth.

38. The instrument according to claim 37 wherein said linear edge blade member is extendible through an opening extending through said tissue engaging surface.

39. An apparatus for remotely removing a tissue specimen comprising:
a shaft coupled to a distal housing;
said distal housing having a cavity into which tissue is receivable and a surface disposed in said cavity;
said shaft having one or more paths for communicating suction to said distal housing to draw tissue against said surface, said surface having one or more openings for communicating suction to tissue; and
a blade disposed in said distal housing for cutting tissue present in said cavity when engaged by said suction against said surface, wherein the tissue is retainable in said cavity of said distal housing after extension of said blade sufficiently across said surface, wherein said distal housing further comprises an opening along one single side of said cavity into which tissue is receivable, and said surface extends in said cavity and faces said opening, and tissue is drawn by suction against said surface via said opening along said side of said cavity.

40. The apparatus according to claim 39 wherein said blade is extendable with respect to said opening of said cavity to cut said tissue and thereby capture said cut tissue in said cavity.

41. The apparatus according to claim 39 wherein the tissue is capable of being held solely by said suction at said distal end against said surface.

42. The apparatus according to claim 39 further comprising one or more needles extending through said shaft which are extendible into said tissue when engaged by said suction against said surface.

43. The apparatus according to claim 42 wherein said one or more needles enable injection of fluid into tissue while suction is being communicated to said tissue.

44. The apparatus according to claim 39 wherein said surface represents a contoured surface with said one or more openings to communicate said suction, and said tissue specimen cut by said blade has a depth in accordance with the size of said cavity and the contour of said surface.

45. The apparatus according to claim 39 wherein said blade is one of a rotatable tubular blade or an oscillating blade member translatable in the distal end to cut the tissue.

46. The apparatus according to claim 39 wherein said blade has an edge for cutting tissue, and said blade when extended across said surface said edge of said blade is shaped to provide a single slice through said tissue engaged against said tissue engaging surface.

47. An apparatus for remotely cutting tissue comprising:
a shaft coupled to a distal housing;
said distal housing having a cavity into which tissue is receivable and a surface extending in said cavity;
said shaft having one or more paths for communicating suction to said distal housing to draw tissue against said surface, said surface having one or more openings for communicating suction to tissue; and
a blade extendible in the distal housing for cutting tissue in said cavity when engaged against said surface to make a linear slit incision through said engaged tissue, wherein said distal housing further comprises an opening along one single side of said cavity into which tissue is receivable, and said surface extends in said cavity and faces said opening, and tissue is drawn by suction against said surface via said opening along said side of said cavity.

48. The apparatus according to claim 47 wherein the tissue is capable of being held solely by said suction at said distal end against said surface.

49. The apparatus according to claim 47 wherein said blade is oriented along a longitudinal dimension of the cavity.

* * * * *